(12) United States Patent
Moss et al.

(10) Patent No.: US 9,757,196 B2
(45) Date of Patent: Sep. 12, 2017

(54) MULTIPLE TREATMENT ZONE ABLATION PROBE

(71) Applicant: AngioDynamics, Inc., Latham, NY (US)

(72) Inventors: Kevin L Moss, Freemont, CA (US); Robert M Pearson, San Jose, CA (US)

(73) Assignee: AngioDynamics, Inc.

( * ) Notice: Subject to any disclaimer, the term of this patent is extended or adjusted under 35 U.S.C. 154(b) by 0 days.

(21) Appl. No.: 14/989,061

(22) Filed: Jan. 6, 2016

(65) Prior Publication Data

US 2016/0113708 A1 Apr. 28, 2016

Related U.S. Application Data

(63) Continuation of application No. 14/733,115, filed on Jun. 8, 2015, now abandoned, which is a (Continued)

(51) Int. Cl.
*A61N 1/00* (2006.01)
*A61B 18/18* (2006.01)
(Continued)

(52) U.S. Cl.
CPC .......... *A61B 18/18* (2013.01); *A61B 18/1477* (2013.01); *A61B 18/1487* (2013.01);
(Continued)

(58) Field of Classification Search
USPC ...................................................... 606/27, 41
See application file for complete search history.

(56) References Cited

U.S. PATENT DOCUMENTS 1,653,819 A 12/1927 Ephraim et al.
3,730,238 A 5/1973 Butler
(Continued)

FOREIGN PATENT DOCUMENTS

AU 7656800 A 4/2001
AU 2002315095 A1 12/2002
(Continued)

OTHER PUBLICATIONS

Cowley, Lifestyle Good news for boomers, Newsweek, Dec. 30, 1996.
(Continued)

*Primary Examiner* — Nicole F Johnson
(74) *Attorney, Agent, or Firm* — Zachary F. Madonna

(57) ABSTRACT

An energy delivery probe and method of using the energy delivery probe to treat a patient is provided herein. The energy delivery probe has at least one probe body having a longitudinal axis and at least a first trocar and a second trocar. Each trocar comprises at least two electrodes that are electrically insulated from each other, and each electrode is independently selectively activatable. An insulative sleeve is positioned in a coaxially surrounding relationship to each of the first trocar and the second trocar. The probe also has a switching means for independently activating at least one electrode. The method involves independently and selectively activating the first and second electrodes to form an ablation zone, then repeating the ablation by delivering energy to a second set of electrodes, producing one or more overlapping ablation zone, and eliminating the need to reposition the ablation probes.

13 Claims, 15 Drawing Sheets

Related U.S. Application Data continuation-in-part of application No. 13/630,135, filed on Sep. 28, 2012, now Pat. No. 9,078,665.

(51) Int. Cl.
  *A61B 18/14* (2006.01)
  *A61B 90/00* (2016.01)
  *A61B 18/00* (2006.01)

(52) U.S. Cl.
  CPC .............. *A61B 18/1815* (2013.01); *A61B 2018/00029* (2013.01); *A61B 2018/00083* (2013.01); *A61B 2018/00273* (2013.01); *A61B 2018/00529* (2013.01); *A61B 2018/00577* (2013.01); *A61B 2018/00589* (2013.01); *A61B 2018/00613* (2013.01); *A61B 2018/1467* (2013.01); *A61B 2018/1475* (2013.01); *A61B 2090/036* (2016.02)

(56) References Cited

U.S. PATENT DOCUMENTS

| | | |
|---|---|---|
| 3,746,004 A | 7/1973 | Jankelson |
| 3,871,359 A | 3/1975 | Pacela |
| 4,016,886 A | 4/1977 | Doss et al. |
| 4,037,341 A | 7/1977 | Odle et al. |
| 4,216,860 A | 8/1980 | Heimann |
| 4,226,246 A | 10/1980 | Fragnet |
| 4,262,672 A | 4/1981 | Kief |
| 4,267,047 A | 5/1981 | Henne et al. |
| 4,278,092 A | 7/1981 | Borsanyi et al. |
| 4,299,217 A | 11/1981 | Sagae et al. |
| 4,311,148 A | 1/1982 | Courtney et al. |
| 4,336,881 A | 6/1982 | Babb et al. |
| 4,344,436 A | 8/1982 | Kubota |
| 4,392,855 A | 7/1983 | Oreopoulos et al. |
| 4,406,827 A | 9/1983 | Carim |
| 4,407,943 A | 10/1983 | Cole et al. |
| 4,416,276 A | 11/1983 | Newton et al. |
| 4,447,235 A | 5/1984 | Clarke |
| 4,469,098 A | 9/1984 | Davi |
| 4,489,535 A | 12/1984 | Veltman |
| 4,512,765 A | 4/1985 | Muto |
| 4,580,572 A | 4/1986 | Granek et al. |
| 4,636,199 A | 1/1987 | Victor |
| 4,672,969 A | 6/1987 | Dew |
| 4,676,258 A | 6/1987 | Inokuchi et al. |
| 4,676,782 A | 6/1987 | Yamamoto et al. |
| 4,687,471 A | 8/1987 | Twardowski et al. |
| 4,716,896 A | 1/1988 | Ackerman |
| 4,723,549 A | 2/1988 | Wholey et al. |
| D294,519 S | 3/1988 | Hardy, Jr. |
| 4,756,838 A | 7/1988 | Veltman |
| 4,772,269 A | 9/1988 | Twardowski et al. |
| 4,798,585 A | 1/1989 | Inoue et al. |
| 4,810,963 A | 3/1989 | Blake-Coleman et al. |
| 4,813,929 A | 3/1989 | Semrad |
| 4,819,637 A | 4/1989 | Dormandy, Jr. et al. |
| 4,822,470 A | 4/1989 | Chang |
| 4,836,204 A | 6/1989 | Landymore et al. |
| 4,840,172 A | 6/1989 | Augustine et al. |
| 4,863,426 A | 9/1989 | Ferragamo et al. |
| 4,885,003 A | 12/1989 | Hillstead |
| 4,886,496 A | 12/1989 | Conoscenti et al. |
| 4,886,502 A | 12/1989 | Poirier et al. |
| 4,889,634 A | 12/1989 | El-Rashidy |
| 4,907,601 A | 3/1990 | Frick |
| 4,919,148 A | 4/1990 | Muccio |
| 4,920,978 A | 5/1990 | Colvin |
| 4,921,484 A | 5/1990 | Hillstead |
| 4,946,793 A | 8/1990 | Marshall, III |
| 4,976,709 A | 12/1990 | Sand |
| 4,981,477 A | 1/1991 | Schon et al. |
| 4,986,810 A | 1/1991 | Semrad |
| 4,987,895 A | 1/1991 | Heimlich |
| 5,019,034 A | 5/1991 | Weaver et al. |
| 5,031,775 A | 7/1991 | Kane |
| 5,052,391 A | 10/1991 | Silberstone et al. |
| 5,053,013 A | 10/1991 | Ensminger et al. |
| 5,058,605 A | 10/1991 | Slovak |
| 5,071,558 A | 12/1991 | Itob |
| 5,098,843 A | 3/1992 | Calvin |
| 5,122,137 A | 6/1992 | Lennox |
| 5,134,070 A | 7/1992 | Casnig |
| 5,137,517 A | 8/1992 | Loney et al. |
| 5,141,499 A | 8/1992 | Zappacosta |
| D329,496 S | 9/1992 | Wotton |
| 5,156,597 A | 10/1992 | Verreet et al. |
| 5,173,158 A | 12/1992 | Schmukler |
| 5,186,715 A | 2/1993 | Phillips et al. |
| 5,186,800 A | 2/1993 | Dower |
| 5,188,592 A | 2/1993 | Hakki |
| 5,190,541 A | 3/1993 | Abele et al. |
| 5,192,312 A | 3/1993 | Orton |
| 5,193,537 A | 3/1993 | Freeman |
| 5,209,723 A | 5/1993 | Twardowski et al. |
| 5,215,530 A | 6/1993 | Hogan |
| 5,222,997 A | 6/1993 | Montgomery |
| 5,224,933 A | 7/1993 | Bromander |
| 5,227,730 A | 7/1993 | King et al. |
| 5,242,415 A | 9/1993 | Kantrowitz et al. |
| 5,273,525 A | 12/1993 | Hofmann |
| D343,687 S | 1/1994 | Houghton et al. |
| 5,277,201 A | 1/1994 | Stern |
| 5,279,564 A | 1/1994 | Taylor |
| 5,281,213 A | 1/1994 | Milder et al. |
| 5,283,194 A | 2/1994 | Schmukler |
| 5,290,263 A | 3/1994 | Wigness et al. |
| 5,308,325 A | 5/1994 | Quinn et al. |
| 5,308,338 A | 5/1994 | Helfrich |
| 5,318,543 A | 6/1994 | Ross et al. |
| 5,318,563 A | 6/1994 | Malis et al. |
| 5,328,451 A | 7/1994 | Davis et al. |
| 5,334,167 A | 8/1994 | Cocanower |
| D351,661 S | 10/1994 | Fischer |
| 5,383,917 A | 1/1995 | Desai et al. |
| 5,389,069 A | 2/1995 | Weaver |
| 5,391,158 A | 2/1995 | Peters |
| 5,403,311 A | 4/1995 | Abele et al. |
| 5,405,320 A | 4/1995 | Twardowski et al. |
| 5,417,687 A | 5/1995 | Nardella et al. |
| 5,425,752 A | 6/1995 | Vu'Nguyen |
| 5,439,440 A | 8/1995 | Hofmann |
| 5,439,444 A | 8/1995 | Andersen et al. |
| 5,458,597 A | 10/1995 | Edwards et al. |
| 5,458,625 A | 10/1995 | Kendall |
| 5,462,521 A | 10/1995 | Brucker et al. |
| 5,484,400 A | 1/1996 | Edwards et al. |
| 5,484,401 A | 1/1996 | Rodriguez et al. |
| 5,533,999 A | 7/1996 | Hood et al. |
| 5,536,240 A | 7/1996 | Edwards et al. |
| 5,536,267 A | 7/1996 | Edwards et al. |
| 5,540,737 A | 7/1996 | Fenn |
| 5,546,940 A | 8/1996 | Panescu et al. |
| 5,562,720 A | 10/1996 | Stern et al. |
| 5,575,811 A | 11/1996 | Reid et al. |
| D376,652 S | 12/1996 | Hunt et al. |
| 5,582,588 A | 12/1996 | Sakurai et al. |
| 5,586,982 A | 12/1996 | Abela |
| 5,588,424 A | 12/1996 | Insler et al. |
| 5,588,960 A | 12/1996 | Edwards et al. |
| 5,599,294 A | 2/1997 | Edwards et al. |
| 5,599,311 A | 2/1997 | Raulerson |
| 5,616,126 A | 4/1997 | Malekmehr et al. |
| 5,620,479 A | 4/1997 | Diederich |
| 5,626,146 A | 5/1997 | Barber et al. |
| 5,630,426 A | 5/1997 | Eggers et al. |
| D380,272 S | 6/1997 | Partika et al. |
| 5,634,899 A | 6/1997 | Shapland et al. |
| 5,643,197 A | 7/1997 | Brucker et al. |
| 5,645,855 A | 7/1997 | Lorenz |
| 5,672,173 A | 9/1997 | Gough et al. |
| 5,672,174 A | 9/1997 | Gough et al. |
| 5,674,267 A | 10/1997 | Mir et al. |

(56) References Cited

U.S. PATENT DOCUMENTS

| | | |
|---|---|---|
| 5,683,384 A | 11/1997 | Gough et al. |
| 5,687,723 A | 11/1997 | Avitall |
| 5,690,620 A | 11/1997 | Knott |
| 5,697,905 A | 12/1997 | d'Ambrosio |
| 5,700,252 A | 12/1997 | Klingenstein |
| 5,702,359 A | 12/1997 | Hofmann et al. |
| 5,707,332 A | 1/1998 | Weinberger |
| 5,718,246 A | 2/1998 | Vona |
| 5,720,921 A | 2/1998 | Meserol |
| 5,728,143 A | 3/1998 | Gough et al. |
| 5,735,847 A | 4/1998 | Gough et al. |
| 5,752,939 A | 5/1998 | Makoto |
| 5,778,894 A | 7/1998 | Dorogi et al. |
| 5,782,827 A | 7/1998 | Gough et al. |
| 5,782,882 A | 7/1998 | Lerman et al. |
| 5,800,378 A | 9/1998 | Edwards et al. |
| 5,800,484 A | 9/1998 | Gough et al. |
| 5,807,272 A | 9/1998 | Kun et al. |
| 5,807,306 A | 9/1998 | Shapland et al. |
| 5,807,395 A | 9/1998 | Mulier et al. |
| 5,810,742 A | 9/1998 | Pearlman |
| 5,810,762 A | 9/1998 | Hofmann |
| 5,810,804 A | 9/1998 | Gough et al. |
| 5,830,184 A | 11/1998 | Basta |
| 5,836,897 A | 11/1998 | Sakurai et al. |
| 5,836,905 A | 11/1998 | Lemelson et al. |
| 5,843,026 A | 12/1998 | Edwards et al. |
| 5,843,182 A | 12/1998 | Goldstein |
| 5,863,290 A | 1/1999 | Gough et al. |
| 5,865,787 A | 2/1999 | Shapland et al. |
| 5,866,756 A | 2/1999 | Giros et al. |
| 5,868,708 A | 2/1999 | Hart et al. |
| 5,873,849 A | 2/1999 | Bernard |
| 5,904,648 A | 5/1999 | Arndt et al. |
| 5,913,855 A | 6/1999 | Gough et al. |
| 5,919,142 A | 7/1999 | Boone et al. |
| 5,919,191 A | 7/1999 | Lennox et al. |
| 5,921,982 A | 7/1999 | Lesh et al. |
| 5,944,710 A | 8/1999 | Dev et al. |
| 5,947,284 A | 9/1999 | Foster |
| 5,947,889 A | 9/1999 | Hehrlein |
| 5,954,745 A | 9/1999 | Gertler et al. |
| 5,957,919 A | 9/1999 | Laufer |
| 5,968,006 A | 10/1999 | Hofmann |
| 5,983,131 A | 11/1999 | Weaver et al. |
| 5,984,896 A | 11/1999 | Boyd |
| 5,991,697 A | 11/1999 | Nelson et al. |
| 5,999,847 A | 12/1999 | Elstrom |
| 6,004,339 A | 12/1999 | Wijay |
| 6,009,347 A | 12/1999 | Hofmann |
| 6,009,877 A | 1/2000 | Edwards |
| 6,010,613 A | 1/2000 | Walters et al. |
| 6,012,885 A | 1/2000 | Taylor et al. |
| 6,016,452 A | 1/2000 | Kasevich |
| 6,029,090 A | 2/2000 | Herbst |
| 6,041,252 A | 3/2000 | Walker et al. |
| 6,043,066 A | 3/2000 | Mangano et al. |
| 6,050,994 A | 4/2000 | Sherman |
| 6,055,453 A | 4/2000 | Hofmann et al. |
| 6,059,780 A | 5/2000 | Gough et al. |
| 6,066,134 A | 5/2000 | Eggers et al. |
| 6,068,121 A | 5/2000 | McGlinch |
| 6,068,650 A | 5/2000 | Hofmann et al. |
| 6,071,281 A | 6/2000 | Burnside et al. |
| 6,074,374 A | 6/2000 | Fulton |
| 6,074,389 A | 6/2000 | Levine et al. |
| 6,085,115 A | 7/2000 | Weaver et al. |
| 6,090,016 A | 7/2000 | Kuo |
| 6,090,105 A | 7/2000 | Zepeda et al. |
| 6,090,106 A | 7/2000 | Goble et al. |
| D430,015 S | 8/2000 | Himbert et al. |
| 6,102,885 A | 8/2000 | Bass |
| 6,106,521 A | 8/2000 | Blewett et al. |
| 6,106,524 A | 8/2000 | Eggers et al. |
| 6,109,270 A | 8/2000 | Mah et al. |
| 6,110,192 A | 8/2000 | Ravenscroft et al. |
| 6,113,593 A | 9/2000 | Tu et al. |
| 6,116,330 A | 9/2000 | Salyer |
| 6,122,599 A | 9/2000 | Mehta |
| 6,123,701 A | 9/2000 | Nezhat |
| 6,132,397 A | 10/2000 | Davis et al. |
| 6,132,419 A | 10/2000 | Hofmann |
| 6,134,460 A | 10/2000 | Chance |
| 6,139,545 A | 10/2000 | Utley et al. |
| 6,150,148 A | 11/2000 | Nanda et al. |
| 6,159,163 A | 12/2000 | Strauss et al. |
| D437,941 S | 2/2001 | Frattini |
| 6,193,715 B1 | 2/2001 | Wrublewski et al. |
| 6,198,970 B1 | 3/2001 | Freed et al. |
| 6,200,314 B1 | 3/2001 | Sherman |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann et al. |
| 6,219,577 B1 | 4/2001 | Brown, III et al. |
| D442,697 S | 5/2001 | Hajianpour |
| 6,233,490 B1 | 5/2001 | Kasevich |
| 6,235,023 B1 | 5/2001 | Lee et al. |
| D443,360 S | 6/2001 | Haberland |
| 6,241,702 B1 | 6/2001 | Lundquist et al. |
| 6,241,725 B1 | 6/2001 | Cosman |
| D445,198 S | 7/2001 | Frattini |
| 6,258,100 B1 | 7/2001 | Alferness et al. |
| 6,261,831 B1 | 7/2001 | Agee |
| 6,277,114 B1 | 8/2001 | Bullivant et al. |
| 6,278,895 B1 | 8/2001 | Bernard |
| 6,280,441 B1 | 8/2001 | Ryan |
| 6,283,988 B1 | 9/2001 | Laufer et al. |
| 6,283,989 B1 | 9/2001 | Laufer et al. |
| 6,284,140 B1 | 9/2001 | Sommermeyer et al. |
| 6,287,293 B1 | 9/2001 | Jones et al. |
| 6,287,304 B1 | 9/2001 | Eggers et al. |
| 6,296,636 B1 | 10/2001 | Cheng et al. |
| 6,298,726 B1 | 10/2001 | Adachi et al. |
| 6,299,633 B1 | 10/2001 | Laufer |
| 6,300,108 B1 | 10/2001 | Rubinsky et al. |
| D450,391 S | 11/2001 | Hunt et al. |
| 6,326,177 B1 | 12/2001 | Schoenbach et al. |
| 6,327,505 B1 | 12/2001 | Medhkour et al. |
| 6,328,689 B1 | 12/2001 | Gonzalez et al. |
| 6,328,735 B1 | 12/2001 | Curley et al. |
| 6,330,478 B1 | 12/2001 | Lee et al. |
| 6,347,247 B1 | 2/2002 | Dev et al. |
| 6,349,233 B1 | 2/2002 | Adams |
| 6,351,674 B2 | 2/2002 | Silverstone |
| 6,387,671 B1 | 5/2002 | Rubinsky et al. |
| 6,403,348 B1 | 6/2002 | Rubinsky et al. |
| 6,405,732 B1 | 6/2002 | Edwards et al. |
| 6,411,852 B1 | 6/2002 | Danek et al. |
| 6,419,674 B1 | 7/2002 | Bowser et al. |
| 6,443,952 B1 | 9/2002 | Mulier et al. |
| 6,463,331 B1 | 10/2002 | Edwards |
| 6,470,211 B1 | 10/2002 | Ideker et al. |
| 6,478,793 B1 | 11/2002 | Cosman et al. |
| 6,482,221 B1 | 11/2002 | Hebert et al. |
| 6,482,619 B1 | 11/2002 | Rubinsky et al. |
| 6,485,487 B1 | 11/2002 | Sherman |
| 6,488,673 B1 | 12/2002 | Laufer et al. |
| 6,488,678 B2 | 12/2002 | Sherman |
| 6,488,680 B1 | 12/2002 | Francischelli et al. |
| 6,491,706 B1 | 12/2002 | Alferness et al. |
| 6,493,589 B1 | 12/2002 | Medhkour et al. |
| 6,493,592 B1 | 12/2002 | Leonard et al. |
| 6,497,704 B2 | 12/2002 | Ein-Gal |
| 6,500,173 B2 | 12/2002 | Underwood et al. |
| 6,503,248 B1 | 1/2003 | Levine |
| 6,506,189 B1 | 1/2003 | Rittman, III et al. |
| 6,514,248 B1 | 2/2003 | Eggers et al. |
| 6,520,183 B2 | 2/2003 | Amar |
| 6,526,320 B2 | 2/2003 | Mitchell |
| D471,640 S | 3/2003 | McMichael et al. |
| D471,641 S | 3/2003 | McMichael et al. |
| 6,530,922 B2 | 3/2003 | Cosman et al. |
| 6,533,784 B2 | 3/2003 | Truckai et al. |

(56) References Cited

U.S. PATENT DOCUMENTS

| | | |
|---|---|---|
| 6,537,976 B1 | 3/2003 | Gupta |
| 6,558,378 B2 | 5/2003 | Sherman et al. |
| 6,562,604 B2 | 5/2003 | Rubinsky et al. |
| 6,575,967 B1 | 6/2003 | Leveen et al. |
| 6,575,969 B1 | 6/2003 | Rittman, III et al. |
| 6,589,161 B2 | 7/2003 | Corcoran |
| 6,589,174 B1 | 7/2003 | Chopra et al. |
| 6,592,594 B2 | 7/2003 | Rimbaugh et al. |
| 6,607,529 B1 | 8/2003 | Jones et al. |
| 6,610,054 B1 | 8/2003 | Edwards et al. |
| 6,611,706 B2 | 8/2003 | Avrahami et al. |
| 6,613,211 B1 | 9/2003 | McCormick et al. |
| 6,616,657 B2 | 9/2003 | Simpson et al. |
| 6,627,421 B1 | 9/2003 | Unger et al. |
| D480,816 S | 10/2003 | McMichael et al. |
| 6,634,363 B1 | 10/2003 | Danek et al. |
| 6,638,253 B2 | 10/2003 | Breznock |
| 6,653,091 B1 | 11/2003 | Dunn et al. |
| 6,666,858 B2 | 12/2003 | Lafontaine |
| 6,669,691 B1 | 12/2003 | Taimisto |
| 6,673,070 B2 | 1/2004 | Edwards et al. |
| 6,678,558 B1 | 1/2004 | Dimmer et al. |
| 6,682,501 B1 | 1/2004 | Nelson et al. |
| 6,689,096 B1 | 2/2004 | Loubens et al. |
| 6,689,127 B1 | 2/2004 | Gough et al. |
| 6,692,493 B2 | 2/2004 | McGovern et al. |
| 6,694,979 B2 | 2/2004 | Deem et al. |
| 6,694,984 B2 | 2/2004 | Habib |
| 6,695,861 B1 | 2/2004 | Rosenberg et al. |
| 6,697,669 B2 | 2/2004 | Dev et al. |
| 6,697,670 B2 | 2/2004 | Chomenky et al. |
| 6,702,808 B1 | 3/2004 | Kreindel |
| 6,712,811 B2 | 3/2004 | Underwood et al. |
| D489,973 S | 5/2004 | Root et al. |
| 6,753,171 B2 | 6/2004 | Karube et al. |
| 6,761,716 B2 | 7/2004 | Kadhiresan et al. |
| 6,770,070 B1 | 8/2004 | Balbierz |
| D495,807 S | 9/2004 | Agbodoe et al. |
| 6,795,728 B2 | 9/2004 | Chornenky et al. |
| 6,801,804 B2 | 10/2004 | Miller et al. |
| 6,812,204 B1 | 11/2004 | McHale et al. |
| 6,837,886 B2 | 1/2005 | Collins et al. |
| 6,847,848 B2 | 1/2005 | Sterzer et al. |
| 6,860,847 B2 | 3/2005 | Alferness et al. |
| 6,865,416 B2 | 3/2005 | Dev et al. |
| 6,869,430 B2 | 3/2005 | Balbierz et al. |
| 6,881,213 B2 | 4/2005 | Ryan et al. |
| 6,892,099 B2 | 5/2005 | Jaafar et al. |
| 6,905,480 B2 | 6/2005 | McGuckin, Jr. et al. |
| 6,912,417 B1 | 6/2005 | Bernard et al. |
| 6,926,713 B2 | 8/2005 | Rioux et al. |
| 6,927,049 B2 | 8/2005 | Rubinsky et al. |
| 6,941,950 B2 | 9/2005 | Wilson et al. |
| 6,942,681 B2 | 9/2005 | Johnson |
| 6,958,062 B1 | 10/2005 | Gough et al. |
| 6,960,189 B2 | 11/2005 | Bates et al. |
| 6,962,587 B2 | 11/2005 | Johnson et al. |
| 6,972,013 B1 | 12/2005 | Zhang et al. |
| 6,972,014 B2 | 12/2005 | Eum et al. |
| 6,989,010 B2 | 1/2006 | Francischelli et al. |
| 6,994,689 B1 | 2/2006 | Zadno-Azizi et al. |
| 6,994,706 B2 | 2/2006 | Chornenky et al. |
| 7,008,421 B2 | 3/2006 | Daniel et al. |
| 7,011,094 B2 | 3/2006 | Rapacki et al. |
| 7,012,061 B1 | 3/2006 | Reiss et al. |
| 7,027,869 B2 | 4/2006 | Danek et al. |
| 7,036,510 B2 | 5/2006 | Zgoda et al. |
| 7,053,063 B2 | 5/2006 | Rubinsky et al. |
| 7,054,685 B2 | 5/2006 | Dimmer et al. |
| 7,063,698 B2 | 6/2006 | Whayne et al. |
| 7,087,040 B2 | 8/2006 | McGuckin, Jr. et al. |
| 7,097,612 B2 | 8/2006 | Bertolero et al. |
| 7,100,616 B2 | 9/2006 | Springmeyer |
| 7,113,821 B1 | 9/2006 | Sun et al. |
| 7,130,697 B2 | 10/2006 | Chornenky et al. |
| 7,162,303 B2 | 1/2007 | Levin et al. |
| 7,169,107 B2 | 1/2007 | Jersey-Willuhn et al. |
| 7,211,083 B2 | 5/2007 | Chornenky et al. |
| 7,232,437 B2 | 6/2007 | Berman et al. |
| 7,250,048 B2 | 7/2007 | Francischelli et al. |
| D549,332 S | 8/2007 | Matsumoto et al. |
| 7,264,002 B2 | 9/2007 | Danek et al. |
| 7,267,676 B2 | 9/2007 | Chornenky et al. |
| 7,273,055 B2 | 9/2007 | Danek et al. |
| 7,291,146 B2 | 11/2007 | Steinke et al. |
| 7,331,940 B2 | 2/2008 | Sommerich |
| 7,331,949 B2 | 2/2008 | Marisi |
| 7,341,558 B2 | 3/2008 | de la Torre et al. |
| 7,344,533 B2 | 3/2008 | Pearson et al. |
| D565,743 S | 4/2008 | Phillips et al. |
| D571,478 S | 6/2008 | Horacek |
| 7,387,626 B2 | 6/2008 | Edwards et al. |
| 7,399,747 B1 | 7/2008 | Clair et al. |
| D575,399 S | 8/2008 | Matsumoto et al. |
| D575,402 S | 8/2008 | Sandor |
| 7,412,977 B2 | 8/2008 | Fields et al. |
| 7,419,487 B2 | 9/2008 | Johnson et al. |
| 7,434,578 B2 | 10/2008 | Dillard et al. |
| 7,437,194 B2 | 10/2008 | Skwarek et al. |
| 7,449,019 B2 | 11/2008 | Uchida et al. |
| 7,451,765 B2 | 11/2008 | Adler |
| 7,455,675 B2 | 11/2008 | Schur et al. |
| 7,476,203 B2 | 1/2009 | DeVore et al. |
| 7,488,292 B2 | 2/2009 | Adachi |
| 7,520,877 B2 | 4/2009 | Lee, Jr. et al. |
| 7,533,671 B2 | 5/2009 | Gonzalez et al. |
| D595,422 S | 6/2009 | Mustapha |
| 7,544,301 B2 | 6/2009 | Shah et al. |
| 7,549,984 B2 | 6/2009 | Mathis |
| 7,553,309 B2 | 6/2009 | Buysse et al. |
| 7,565,208 B2 | 7/2009 | Harris et al. |
| 7,571,729 B2 * | 8/2009 | Saadat ............... A61B 17/0401 128/898 |
| 7,617,005 B2 | 11/2009 | Demarais et al. |
| 7,620,451 B2 | 11/2009 | Demarais et al. |
| 7,620,507 B2 | 11/2009 | Richardson |
| 7,632,291 B2 | 12/2009 | Stephens et al. |
| 7,647,115 B2 | 1/2010 | Levin et al. |
| 7,653,438 B2 | 1/2010 | Deem et al. |
| 7,655,004 B2 | 2/2010 | Long |
| 7,670,333 B2 | 3/2010 | Schatzberger |
| 7,674,249 B2 | 3/2010 | Ivorra et al. |
| 7,680,543 B2 | 3/2010 | Azure |
| D613,418 S | 4/2010 | Ryan et al. |
| 7,699,842 B2 | 4/2010 | Buysse et al. |
| 7,717,948 B2 | 5/2010 | Demarais et al. |
| 7,718,409 B2 | 5/2010 | Rubinsky et al. |
| 7,722,606 B2 | 5/2010 | Azure |
| 7,742,795 B2 | 6/2010 | Stone et al. |
| 7,763,018 B2 | 7/2010 | DeCarlo et al. |
| 7,765,010 B2 | 7/2010 | Chornenky et al. |
| 7,771,401 B2 | 8/2010 | Hekmat et al. |
| 7,776,035 B2 | 8/2010 | Rick et al. |
| 7,815,571 B2 | 10/2010 | Deckman et al. |
| 7,815,662 B2 | 10/2010 | Spivey et al. |
| 7,824,870 B2 | 11/2010 | Kovalcheck et al. |
| RE42,016 E | 12/2010 | Chornenky et al. |
| 7,846,108 B2 | 12/2010 | Turovskiy et al. |
| 7,853,333 B2 | 12/2010 | Demarais |
| D630,321 S | 1/2011 | Hamilton, Jr. |
| D631,154 S | 1/2011 | Hamilton, Jr. |
| 7,874,986 B2 | 1/2011 | Deckman et al. |
| 7,875,025 B2 | 1/2011 | Cockburn et al. |
| 7,879,031 B2 | 2/2011 | Peterson |
| RE42,277 E | 4/2011 | Jaafar et al. |
| 7,918,852 B2 | 4/2011 | Tullis et al. |
| 7,937,143 B2 | 5/2011 | Demarais et al. |
| 7,938,824 B2 | 5/2011 | Chornenky et al. |
| 7,951,582 B2 | 5/2011 | Gazit et al. |
| 7,955,827 B2 | 6/2011 | Rubinsky et al. |
| RE42,835 E | 10/2011 | Chornenky et al. |
| D647,628 S | 10/2011 | Helfteren |
| 8,029,504 B2 | 10/2011 | Long |
| 8,037,591 B2 | 10/2011 | Spivey et al. |

(56) References Cited

U.S. PATENT DOCUMENTS

| | | |
|---|---|---|
| 8,048,067 B2 | 11/2011 | Davalos et al. |
| 8,052,604 B2 | 11/2011 | Lau et al. |
| 8,057,391 B2 | 11/2011 | Lau et al. |
| 8,062,290 B2 | 11/2011 | Buysse et al. |
| RE43,009 E | 12/2011 | Chornenky et al. |
| 8,070,759 B2 | 12/2011 | Stefanchik et al. |
| 8,075,572 B2 | 12/2011 | Stefanchik et al. |
| 8,088,072 B2 | 1/2012 | Munrow et al. |
| 8,100,922 B2 | 1/2012 | Griffith |
| 8,109,926 B2 | 2/2012 | Azure |
| 8,114,070 B2 | 2/2012 | Rubinsky et al. |
| 8,114,072 B2 | 2/2012 | Long et al. |
| 8,114,119 B2 | 2/2012 | Spivey et al. |
| 8,131,371 B2 | 3/2012 | Demarals et al. |
| 8,131,372 B2 | 3/2012 | Levin et al. |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,154,288 B2 | 4/2012 | Deimling |
| 8,157,834 B2 | 4/2012 | Conlon |
| 8,162,918 B2 | 4/2012 | Ivorra et al. |
| 8,172,772 B2 | 5/2012 | Zwolinski et al. |
| 8,174,267 B2 | 5/2012 | Brannan et al. |
| 8,175,711 B2 | 5/2012 | Demarais et al. |
| 8,180,433 B2 | 5/2012 | Brannan et al. |
| 8,181,995 B2 | 5/2012 | DeCarlo |
| 8,182,477 B2 | 5/2012 | Orszulak et al. |
| 8,187,269 B2 | 5/2012 | Shadduck et al. |
| 8,187,270 B2 | 5/2012 | Auth et al. |
| 8,206,300 B2 | 6/2012 | Deckman et al. |
| 8,211,097 B2 | 7/2012 | Leyh |
| 8,211,099 B2 | 7/2012 | Buysse et al. |
| 8,211,125 B2 | 7/2012 | Spivey |
| 8,216,161 B2 | 7/2012 | Darlington et al. |
| 8,221,411 B2 | 7/2012 | Francischelli et al. |
| 8,231,603 B2 | 7/2012 | Hobbs et al. |
| 8,240,468 B2 | 8/2012 | Wilkinson et al. |
| 8,241,204 B2 | 8/2012 | Spivey |
| 8,242,782 B2 | 8/2012 | Brannan et al. |
| 8,246,615 B2 | 8/2012 | Behnke |
| 8,248,075 B2 | 8/2012 | Brannan et al. |
| 8,251,986 B2 | 8/2012 | Chornenky et al. |
| 8,252,057 B2 | 8/2012 | Fox |
| 8,262,563 B2 | 9/2012 | Bakos et al. |
| 8,262,577 B2 | 9/2012 | Munrow et al. |
| 8,262,655 B2 | 9/2012 | Ghabrial et al. |
| 8,262,680 B2 | 9/2012 | Swain et al. |
| 8,267,927 B2 | 9/2012 | Dalal et al. |
| 8,267,936 B2 | 9/2012 | Hushka et al. |
| 8,277,379 B2 | 10/2012 | Lau et al. |
| 8,282,631 B2 | 10/2012 | Davalos et al. |
| 8,287,527 B2 | 10/2012 | Brannan et al. |
| 8,292,880 B2 | 10/2012 | Prakash et al. |
| 8,298,222 B2 | 10/2012 | Rubinsky et al. |
| 8,303,516 B2 | 11/2012 | Schmitz et al. |
| 8,317,806 B2 | 11/2012 | Coe et al. |
| 8,337,394 B2 | 12/2012 | Vakharia |
| 8,343,144 B2 | 1/2013 | Kleyman |
| 8,346,370 B2 | 1/2013 | Haley et al. |
| 8,347,891 B2 | 1/2013 | Demarais et al. |
| 8,348,921 B2 | 1/2013 | Ivorra et al. |
| 8,348,938 B2 | 1/2013 | Blomgren et al. |
| 8,353,487 B2 | 1/2013 | Trusty et al. |
| 8,353,902 B2 | 1/2013 | Prakash |
| 8,361,066 B2 | 1/2013 | Long et al. |
| 8,361,112 B2 | 1/2013 | Carroll, II et al. |
| 8,366,712 B2 | 2/2013 | Bleich et al. |
| 8,377,057 B2 | 2/2013 | Rick et al. |
| 8,380,283 B2 | 2/2013 | Krieg |
| 8,394,092 B2 | 3/2013 | Brannan |
| 8,394,102 B2 | 3/2013 | Garabedian et al. |
| 8,398,626 B2 | 3/2013 | Buysse et al. |
| 8,398,641 B2 | 3/2013 | Wallace et al. |
| 8,403,924 B2 | 3/2013 | Behnke et al. |
| 8,403,926 B2 | 3/2013 | Nobis et al. |
| 8,409,200 B2 | 4/2013 | Holcomb et al. |
| 8,409,206 B2 | 4/2013 | Wallace et al. |
| 8,417,328 B2 | 4/2013 | Sarfaty et al. |
| 8,425,455 B2 | 4/2013 | Nentwick |
| 8,425,505 B2 | 4/2013 | Long |
| 8,433,423 B2 | 4/2013 | Demarais |
| 8,437,845 B2 | 5/2013 | Sarfaty et al. |
| 8,439,907 B2 | 5/2013 | Auth et al. |
| 8,444,640 B2 | 5/2013 | Demarais et al. |
| 8,449,538 B2 | 5/2013 | Long |
| 8,454,594 B2 | 6/2013 | Demarais et al. |
| 8,465,484 B2 | 6/2013 | Davalos et al. |
| 8,469,716 B2 | 6/2013 | Fedotov et al. |
| 8,473,067 B2 | 6/2013 | Hastings et al. |
| 8,480,657 B2 | 7/2013 | Bakos |
| 8,480,665 B2 | 7/2013 | DeCarlo |
| 8,480,666 B2 | 7/2013 | Buysse et al. |
| 8,480,689 B2 | 7/2013 | Spivey et al. |
| 8,489,192 B1 | 7/2013 | Hlavka et al. |
| 8,496,574 B2 | 7/2013 | Trusty et al. |
| 8,506,485 B2 | 8/2013 | Deckman et al. |
| 8,506,564 B2 | 8/2013 | Long et al. |
| 8,511,317 B2 | 8/2013 | Thapliyal et al. |
| 8,512,329 B2 | 8/2013 | Paulus |
| 8,512,330 B2 | 8/2013 | Epstein et al. |
| 8,518,031 B2 | 8/2013 | Boyden et al. |
| 8,529,563 B2 | 9/2013 | Long et al. |
| 8,542,019 B2 | 9/2013 | Brannan et al. |
| 8,546,979 B2 | 10/2013 | Heeren et al. |
| 8,548,600 B2 | 10/2013 | Deem et al. |
| 8,551,069 B2 | 10/2013 | Demarais et al. |
| 8,551,088 B2 | 10/2013 | Falkenstein et al. |
| 8,551,097 B2 | 10/2013 | Schmitz et al. |
| 8,562,588 B2 | 10/2013 | Hobbs et al. |
| 8,562,598 B2 | 10/2013 | Falkenstein et al. |
| 8,562,599 B2 | 10/2013 | Leyh |
| 8,562,602 B2 | 10/2013 | Azure |
| 8,568,401 B2 | 10/2013 | Brannan |
| 8,568,402 B2 | 10/2013 | Buysse et al. |
| 8,568,404 B2 | 10/2013 | Brannan |
| 8,568,410 B2 | 10/2013 | Vakharia et al. |
| 8,568,411 B2 | 10/2013 | Falkenstein et al. |
| 8,579,894 B2 | 11/2013 | Falkenstein et al. |
| 8,579,897 B2 | 11/2013 | Vakharia et al. |
| 8,579,902 B2 | 11/2013 | Bleich et al. |
| 8,585,704 B2 | 11/2013 | Schmitz et al. |
| 8,603,087 B2 | 12/2013 | Rubinsky et al. |
| 8,608,652 B2 | 12/2013 | Voegele et al. |
| 8,608,739 B2 | 12/2013 | Sartor et al. |
| 8,613,745 B2 | 12/2013 | Bleich |
| 8,617,163 B2 | 12/2013 | Bleich |
| 8,620,423 B2 | 12/2013 | Demarais et al. |
| 8,626,300 B2 | 1/2014 | Demarais et al. |
| 8,632,534 B2 | 1/2014 | Pearson et al. |
| 8,634,929 B2 | 1/2014 | Chornenky et al. |
| 8,647,338 B2 | 2/2014 | Chornenky et al. |
| 8,647,346 B2 | 2/2014 | Bleich et al. |
| 8,652,130 B2 | 2/2014 | Kreindel |
| 8,652,138 B2 | 2/2014 | Bleich et al. |
| 8,652,150 B2 | 2/2014 | Swain et al. |
| 8,663,210 B2 | 3/2014 | Tomasello |
| 8,663,228 B2 | 3/2014 | Schmitz et al. |
| 8,668,688 B2 | 3/2014 | Rusin |
| 8,672,937 B2 | 3/2014 | Decarlo et al. |
| 8,679,003 B2 | 3/2014 | Spivey |
| 8,684,998 B2 | 4/2014 | Demarais et al. |
| 8,706,258 B2 | 4/2014 | Nabors, Sr. et al. |
| 8,712,500 B2 | 4/2014 | Schmidt et al. |
| 8,721,637 B2 | 5/2014 | Zarins et al. |
| 8,725,249 B2 | 5/2014 | Bar-Yoseph et al. |
| 8,728,137 B2 | 5/2014 | Zarins et al. |
| 8,728,138 B2 | 5/2014 | Zarins et al. |
| 8,728,139 B2 | 5/2014 | Azure et al. |
| 8,731,672 B2 | 5/2014 | Hlavka et al. |
| 8,740,895 B2 | 6/2014 | Mayse et al. |
| 8,740,896 B2 | 6/2014 | Zarins et al. |
| 8,753,335 B2 | 6/2014 | Moshe et al. |

(56) References Cited

U.S. PATENT DOCUMENTS

| | | |
|---|---|---|
| 8,768,470 B2 | 7/2014 | Deem et al. |
| 8,771,252 B2 | 7/2014 | Gelfand et al. |
| 8,771,260 B2 | 7/2014 | Conlon et al. |
| 8,774,913 B2 | 7/2014 | Demarais et al. |
| 8,774,922 B2 | 7/2014 | Zarins et al. |
| 8,777,943 B2 | 7/2014 | Mayse et al. |
| 8,784,463 B2 | 7/2014 | Zarins et al. |
| 8,797,039 B2 | 8/2014 | Brannan et al. |
| 8,801,626 B2 | 8/2014 | Sun et al. |
| 8,805,545 B2 | 8/2014 | Zarins |
| 8,808,280 B2 | 8/2014 | Mayse et al. |
| 8,814,860 B2 | 8/2014 | Davalos et al. |
| 8,818,514 B2 | 8/2014 | Zarins et al. |
| 8,821,489 B2 | 9/2014 | Mayse et al. |
| 8,828,031 B2 | 9/2014 | Fox et al. |
| 8,835,166 B2 | 9/2014 | Phillips et al. |
| 8,845,559 B2 | 9/2014 | Darlington et al. |
| 8,845,629 B2 | 9/2014 | Demarais et al. |
| 8,845,635 B2 | 9/2014 | Daniel et al. |
| 8,845,639 B2 | 9/2014 | Wallace et al. |
| 8,852,163 B2 | 10/2014 | Deem et al. |
| 8,858,550 B2 | 10/2014 | Busch-Madsen et al. |
| 8,865,076 B2 | 10/2014 | Sarfaty et al. |
| 8,880,185 B2 | 11/2014 | Hastings et al. |
| 8,880,186 B2 | 11/2014 | Levin et al. |
| 8,880,195 B2 | 11/2014 | Azure |
| 8,882,759 B2 | 11/2014 | Manley et al. |
| 8,888,792 B2 | 11/2014 | Harris et al. |
| 8,894,641 B2 | 11/2014 | Brannan |
| 8,903,488 B2 | 12/2014 | Callas et al. |
| 8,906,006 B2 | 12/2014 | Chornenky et al. |
| 8,906,011 B2 | 12/2014 | Gelbart et al. |
| 8,906,035 B2 | 12/2014 | Zwolinski et al. |
| 8,911,439 B2 | 12/2014 | Mayse et al. |
| 8,915,910 B2 | 12/2014 | Falkenstein et al. |
| 8,915,911 B2 | 12/2014 | Azure |
| 8,920,411 B2 | 12/2014 | Gelbart et al. |
| 8,923,970 B2 | 12/2014 | Bar-Yoseph et al. |
| 8,926,606 B2 | 1/2015 | Davalos et al. |
| 8,932,287 B2 | 1/2015 | Gelbart et al. |
| 8,932,289 B2 | 1/2015 | Mayse et al. |
| 8,934,978 B2 | 1/2015 | Deem et al. |
| 8,939,897 B2 | 1/2015 | Nobis |
| 8,939,970 B2 | 1/2015 | Stone et al. |
| 8,945,121 B2 | 2/2015 | Curley |
| 8,948,865 B2 | 2/2015 | Zarins et al. |
| 8,956,350 B2 | 2/2015 | Buysse et al. |
| 8,958,871 B2 | 2/2015 | Demarais et al. |
| 8,958,888 B2 | 2/2015 | Chornenky et al. |
| 8,961,507 B2 | 2/2015 | Mayse et al. |
| 8,961,508 B2 | 2/2015 | Mayse et al. |
| 8,974,451 B2 | 3/2015 | Smith |
| 8,983,595 B2 | 3/2015 | Levin et al. |
| 8,986,294 B2 | 3/2015 | Demarais et al. |
| 8,992,517 B2 | 3/2015 | Davalos et al. |
| 9,005,189 B2 | 4/2015 | Davalos et al. |
| 9,005,195 B2 | 4/2015 | Mayse et al. |
| 9,005,198 B2 | 4/2015 | Long et al. |
| 9,011,431 B2 | 4/2015 | Long et al. |
| 9,017,323 B2 | 4/2015 | Miller et al. |
| 9,017,324 B2 | 4/2015 | Mayse et al. |
| 9,023,034 B2 | 5/2015 | Jenson et al. |
| 9,023,037 B2 | 5/2015 | Zarins et al. |
| 9,028,483 B2 | 5/2015 | Long et al. |
| 9,028,485 B2 | 5/2015 | Edmunds et al. |
| 9,039,702 B2 | 5/2015 | Miller et al. |
| 9,049,987 B2 | 6/2015 | Conlon et al. |
| 9,050,449 B2 | 6/2015 | Darlington et al. |
| 9,060,761 B2 | 6/2015 | Hastings et al. |
| 9,072,518 B2 | 7/2015 | Swanson |
| 9,072,527 B2 | 7/2015 | Deem et al. |
| 9,078,665 B2 | 7/2015 | Moss et al. |
| 9,084,609 B2 | 7/2015 | Smith |
| 9,089,350 B2 | 7/2015 | Willard |
| 9,101,386 B2 | 8/2015 | Wallace et al. |
| 9,108,040 B2 | 8/2015 | Zarins |
| 9,113,888 B2 | 8/2015 | Orszulak et al. |
| 9,119,633 B2 | 9/2015 | Gelbart et al. |
| 9,119,634 B2 | 9/2015 | Gelbart et al. |
| 9,125,643 B2 | 9/2015 | Hlavka et al. |
| 9,125,661 B2 | 9/2015 | Deem et al. |
| 9,125,666 B2 | 9/2015 | Steinke et al. |
| 9,125,667 B2 | 9/2015 | Stone et al. |
| 9,131,978 B2 | 9/2015 | Zarins et al. |
| 9,138,281 B2 | 9/2015 | Zarins et al. |
| 9,138,287 B2 | 9/2015 | Curley et al. |
| 9,138,288 B2 | 9/2015 | Curley |
| 9,149,328 B2 | 10/2015 | Dimmer et al. |
| 9,155,589 B2 | 10/2015 | Jenson |
| 9,173,704 B2 | 11/2015 | Hobbs et al. |
| 9,186,198 B2 | 11/2015 | Demarais et al. |
| 9,186,209 B2 | 11/2015 | Weber et al. |
| 9,186,213 B2 | 11/2015 | Deem et al. |
| 9,192,435 B2 | 11/2015 | Jenson |
| 9,192,715 B2 | 11/2015 | Gelfand et al. |
| 9,192,790 B2 | 11/2015 | Hastings et al. |
| 9,198,733 B2 | 12/2015 | Neal, II et al. |
| 9,220,526 B2 | 12/2015 | Conlon |
| 9,220,558 B2 | 12/2015 | Willard |
| 9,220,561 B2 | 12/2015 | Crow et al. |
| 9,226,772 B2 | 1/2016 | Fox |
| 9,226,790 B2 | 1/2016 | Zemel et al. |
| 9,233,241 B2 | 1/2016 | Long |
| 9,247,952 B2 | 2/2016 | Bleich et al. |
| 9,248,318 B2 | 2/2016 | Darlington et al. |
| 9,254,169 B2 | 2/2016 | Long et al. |
| 9,254,172 B2 | 2/2016 | Behnke, II et al. |
| 9,265,557 B2 | 2/2016 | Sherman et al. |
| 9,265,558 B2 | 2/2016 | Zarins et al. |
| 9,276,367 B2 | 3/2016 | Brannan |
| 9,277,955 B2 | 3/2016 | Herscher et al. |
| 9,277,969 B2 | 3/2016 | Brannan et al. |
| 9,283,051 B2 | 3/2016 | Garcia et al. |
| 9,289,255 B2 | 3/2016 | Deem et al. |
| 9,295,516 B2 | 3/2016 | Pearson et al. |
| 9,307,935 B2 | 4/2016 | Pluta et al. |
| 9,308,039 B2 | 4/2016 | Azure |
| 9,308,043 B2 | 4/2016 | Zarins et al. |
| 9,308,044 B2 | 4/2016 | Zarins et al. |
| 9,314,620 B2 | 4/2016 | Long et al. |
| 9,314,630 B2 | 4/2016 | Levin et al. |
| 9,320,561 B2 | 4/2016 | Zarins et al. |
| 9,320,563 B2 | 4/2016 | Brustad et al. |
| 9,326,751 B2 | 5/2016 | Hastings |
| 9,326,817 B2 | 5/2016 | Zarins et al. |
| 9,327,100 B2 | 5/2016 | Perry et al. |
| 9,327,122 B2 | 5/2016 | Zarins et al. |
| 9,339,618 B2 | 5/2016 | Deem et al. |
| 9,351,790 B2 | 5/2016 | Zemel et al. |
| 2001/0039393 A1 | 11/2001 | Mori et al. |
| 2001/0044596 A1 | 11/2001 | Jaafar |
| 2001/0046706 A1 | 11/2001 | Rubinsky et al. |
| 2001/0047167 A1 | 11/2001 | Heggeness |
| 2001/0051366 A1 | 12/2001 | Rubinsky et al. |
| 2002/0002393 A1 | 1/2002 | Mitchell |
| 2002/0010491 A1 | 1/2002 | Schoenbach et al. |
| 2002/0022864 A1 | 2/2002 | Mahvi et al. |
| 2002/0040204 A1 | 4/2002 | Dev et al. |
| 2002/0049370 A1 | 4/2002 | Laufer et al. |
| 2002/0052601 A1 | 5/2002 | Goldberg et al. |
| 2002/0055731 A1 | 5/2002 | Atala et al. |
| 2002/0065541 A1 | 5/2002 | Fredricks et al. |
| 2002/0072742 A1 | 6/2002 | Schaefer et al. |
| 2002/0077314 A1 | 6/2002 | Falk et al. |
| 2002/0077627 A1 | 6/2002 | Johnson et al. |
| 2002/0077676 A1 | 6/2002 | Schroeppel et al. |
| 2002/0082543 A1 | 6/2002 | Park et al. |
| 2002/0095197 A1 | 7/2002 | Lardo et al. |
| 2002/0099323 A1 | 7/2002 | Dev et al. |
| 2002/0111615 A1 | 8/2002 | Cosman et al. |
| 2002/0112729 A1 | 8/2002 | DeVore et al. |
| 2002/0115208 A1 | 8/2002 | Mitchell et al. |
| 2002/0119437 A1 | 8/2002 | Grooms et al. |
| 2002/0133324 A1 | 9/2002 | Weaver et al. |

(56) References Cited

U.S. PATENT DOCUMENTS

| | | |
|---|---|---|
| 2002/0137121 A1 | 9/2002 | Rubinsky et al. |
| 2002/0138075 A1 | 9/2002 | Edwards et al. |
| 2002/0138117 A1 | 9/2002 | Son |
| 2002/0143365 A1 | 10/2002 | Herbst |
| 2002/0147462 A1 | 10/2002 | Mair et al. |
| 2002/0156472 A1 | 10/2002 | Lee et al. |
| 2002/0161361 A1 | 10/2002 | Sherman et al. |
| 2002/0183684 A1 | 12/2002 | Dev et al. |
| 2002/0183735 A1 | 12/2002 | Edwards et al. |
| 2002/0183740 A1 | 12/2002 | Edwards et al. |
| 2002/0188242 A1 | 12/2002 | Wu |
| 2002/0193784 A1 | 12/2002 | McHale et al. |
| 2002/0193831 A1 | 12/2002 | Smith |
| 2003/0009110 A1 | 1/2003 | Tu et al. |
| 2003/0014047 A1 | 1/2003 | Woloszko et al. |
| 2003/0055220 A1 | 3/2003 | Legrain |
| 2003/0055420 A1 | 3/2003 | Kadhiresan et al. |
| 2003/0059945 A1 | 3/2003 | Dzekunov et al. |
| 2003/0060856 A1 | 3/2003 | Chornenky et al. |
| 2003/0078490 A1 | 4/2003 | Damasco et al. |
| 2003/0088189 A1 | 5/2003 | Tu et al. |
| 2003/0088199 A1 | 5/2003 | Kawaji |
| 2003/0096407 A1 | 5/2003 | Atala et al. |
| 2003/0105454 A1 | 6/2003 | Cucin |
| 2003/0109871 A1 | 6/2003 | Johnson et al. |
| 2003/0127090 A1 | 7/2003 | Gifford et al. |
| 2003/0130711 A1 | 7/2003 | Pearson et al. |
| 2003/0135242 A1 | 7/2003 | Mongeon et al. |
| 2003/0149451 A1 | 8/2003 | Chomenky et al. |
| 2003/0154988 A1 | 8/2003 | DeVore et al. |
| 2003/0159700 A1 | 8/2003 | Laufer et al. |
| 2003/0164168 A1 | 9/2003 | Shaw |
| 2003/0166181 A1 | 9/2003 | Rubinsky et al. |
| 2003/0170898 A1 | 9/2003 | Gundersen et al. |
| 2003/0194808 A1 | 10/2003 | Rubinsky et al. |
| 2003/0195385 A1 | 10/2003 | DeVore |
| 2003/0195406 A1 | 10/2003 | Jenkins et al. |
| 2003/0199050 A1 | 10/2003 | Mangano et al. |
| 2003/0208200 A1 | 11/2003 | Palanker et al. |
| 2003/0212394 A1 | 11/2003 | Pearson et al. |
| 2003/0212412 A1 | 11/2003 | Dillard et al. |
| 2003/0225360 A1 | 12/2003 | Eppstein et al. |
| 2003/0228344 A1 | 12/2003 | Fields et al. |
| 2004/0009459 A1 | 1/2004 | Anderson et al. |
| 2004/0019371 A1 | 1/2004 | Jaafar et al. |
| 2004/0055606 A1 | 3/2004 | Hendricksen et al. |
| 2004/0059328 A1 | 3/2004 | Daniel et al. |
| 2004/0059389 A1 | 3/2004 | Chornenky et al. |
| 2004/0068228 A1 | 4/2004 | Cunningham |
| 2004/0116965 A1 | 6/2004 | Falkenberg |
| 2004/0133194 A1 | 7/2004 | Eum et al. |
| 2004/0138715 A1 | 7/2004 | van Groeningen et al. |
| 2004/0146877 A1 | 7/2004 | Diss et al. |
| 2004/0153057 A1 | 8/2004 | Davison |
| 2004/0167458 A1 | 8/2004 | Draghia-Akli et al. |
| 2004/0172136 A1 | 9/2004 | Ralph et al. |
| 2004/0176855 A1 | 9/2004 | Badylak |
| 2004/0193097 A1 | 9/2004 | Hofmann et al. |
| 2004/0199159 A1 | 10/2004 | Lee et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0230187 A1 | 11/2004 | Lee et al. |
| 2004/0236376 A1 | 11/2004 | Miklavcic et al. |
| 2004/0243107 A1 | 12/2004 | Macoviak et al. |
| 2004/0267189 A1 | 12/2004 | Mavor et al. |
| 2004/0267340 A1 | 12/2004 | Cioanta et al. |
| 2005/0010209 A1 | 1/2005 | Lee, Jr. et al. |
| 2005/0010259 A1 | 1/2005 | Gerber |
| 2005/0013870 A1 | 1/2005 | Freyman et al. |
| 2005/0020965 A1 | 1/2005 | Rioux et al. |
| 2005/0033276 A1 | 2/2005 | Adachi |
| 2005/0043726 A1 | 2/2005 | McHale et al. |
| 2005/0049541 A1 | 3/2005 | Behar et al. |
| 2005/0054978 A1 | 3/2005 | Segal et al. |
| 2005/0061322 A1 | 3/2005 | Freitag |
| 2005/0066974 A1 | 3/2005 | Fields et al. |
| 2005/0096537 A1 | 5/2005 | Parel et al. |
| 2005/0096709 A1 | 5/2005 | Skwarek et al. |
| 2005/0107781 A1 | 5/2005 | Ostrovsky et al. |
| 2005/0143817 A1 | 6/2005 | Hunter et al. |
| 2005/0165393 A1 | 7/2005 | Eppstein |
| 2005/0171522 A1 | 8/2005 | Christopherson |
| 2005/0171523 A1 | 8/2005 | Rubinsky et al. |
| 2005/0171574 A1 | 8/2005 | Rubinsky et al. |
| 2005/0182462 A1 | 8/2005 | Chornenky et al. |
| 2005/0197619 A1 | 9/2005 | Rule et al. |
| 2005/0216047 A1 | 9/2005 | Kumoyama et al. |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0261672 A1 | 11/2005 | Deem et al. |
| 2005/0261707 A1 | 11/2005 | Schatzberger |
| 2005/0267407 A1 | 12/2005 | Goldman |
| 2005/0282284 A1 | 12/2005 | Rubinsky et al. |
| 2005/0288684 A1 | 12/2005 | Aronson et al. |
| 2005/0288702 A1 | 12/2005 | McGurk et al. |
| 2005/0288730 A1 | 12/2005 | Deem et al. |
| 2006/0004356 A1 | 1/2006 | Bilski et al. |
| 2006/0004400 A1 | 1/2006 | McGurk et al. |
| 2006/0009748 A1 | 1/2006 | Mathis |
| 2006/0015147 A1 | 1/2006 | Persson et al. |
| 2006/0020347 A1 | 1/2006 | Barrett et al. |
| 2006/0024359 A1 | 2/2006 | Walker et al. |
| 2006/0025760 A1 | 2/2006 | Podhajsky |
| 2006/0025821 A1 | 2/2006 | Gelfand et al. |
| 2006/0030810 A1 | 2/2006 | Mandrusov et al. |
| 2006/0074413 A1 | 4/2006 | Behzadian |
| 2006/0079838 A1 | 4/2006 | Walker et al. |
| 2006/0079845 A1 | 4/2006 | Howard et al. |
| 2006/0079883 A1 | 4/2006 | Elmouelhi et al. |
| 2006/0089635 A1 | 4/2006 | Young et al. |
| 2006/0106379 A1 | 5/2006 | O'Brien et al. |
| 2006/0121610 A1 | 6/2006 | Rubinsky et al. |
| 2006/0127703 A1 | 6/2006 | Takekuma et al. |
| 2006/0142801 A1 | 6/2006 | Demarais et al. |
| 2006/0149123 A1 | 7/2006 | Vidlund et al. |
| 2006/0173490 A1 | 8/2006 | Lafontaine et al. |
| 2006/0182684 A1 | 8/2006 | Beliveau |
| 2006/0184163 A1 | 8/2006 | Breen et al. |
| 2006/0195146 A1 | 8/2006 | Tracey et al. |
| 2006/0206150 A1 | 9/2006 | Demarais et al. |
| 2006/0212032 A1 | 9/2006 | Daniel et al. |
| 2006/0212076 A1 | 9/2006 | Demarais et al. |
| 2006/0212078 A1 | 9/2006 | Demarais et al. |
| 2006/0217703 A1 | 9/2006 | Chornenky et al. |
| 2006/0217704 A1 | 9/2006 | Cockburn et al. |
| 2006/0224188 A1 | 10/2006 | Libbus et al. |
| 2006/0224192 A1 | 10/2006 | Dimmer et al. |
| 2006/0235474 A1 | 10/2006 | Demarais |
| 2006/0247619 A1 | 11/2006 | Kaplan et al. |
| 2006/0264752 A1 | 11/2006 | Rubinsky et al. |
| 2006/0264807 A1 | 11/2006 | Westersten et al. |
| 2006/0269531 A1 | 11/2006 | Beebe et al. |
| 2006/0271111 A1 | 11/2006 | Demarais et al. |
| 2006/0276710 A1 | 12/2006 | Krishnan |
| 2006/0283462 A1 | 12/2006 | Fields et al. |
| 2006/0293713 A1 | 12/2006 | Rubinsky et al. |
| 2006/0293725 A1 | 12/2006 | Rubinsky et al. |
| 2006/0293730 A1 | 12/2006 | Rubinsky et al. |
| 2006/0293731 A1 | 12/2006 | Rubinsky et al. |
| 2006/0293734 A1 | 12/2006 | Scott et al. |
| 2007/0010805 A1 | 1/2007 | Fedewa et al. |
| 2007/0016183 A1 | 1/2007 | Lee et al. |
| 2007/0016185 A1 | 1/2007 | Tullis et al. |
| 2007/0021803 A1 | 1/2007 | Deem et al. |
| 2007/0025919 A1 | 2/2007 | Deem et al. |
| 2007/0043345 A1 | 2/2007 | Davalos et al. |
| 2007/0055142 A1 | 3/2007 | Webler |
| 2007/0060989 A1 | 3/2007 | Deem et al. |
| 2007/0066957 A1 | 3/2007 | Demarais et al. |
| 2007/0066971 A1 | 3/2007 | Podhajsky |
| 2007/0078391 A1 | 4/2007 | Wortley et al. |
| 2007/0078453 A1 | 4/2007 | Johnson et al. |

(56) References Cited

U.S. PATENT DOCUMENTS

| | | |
|---|---|---|
| 2007/0083239 A1 | 4/2007 | Demarais et al. |
| 2007/0093789 A1 | 4/2007 | Smith |
| 2007/0096048 A1 | 5/2007 | Clerc |
| 2007/0118069 A1 | 5/2007 | Persson et al. |
| 2007/0129711 A1 | 6/2007 | Altshuler et al. |
| 2007/0137567 A1 | 6/2007 | Shimizu et al. |
| 2007/0156129 A1 | 7/2007 | Kovalcheck |
| 2007/0156135 A1 | 7/2007 | Rubinsky et al. |
| 2007/0156136 A1 | 7/2007 | Godara et al. |
| 2007/0173899 A1 | 7/2007 | Levin et al. |
| 2007/0179380 A1 | 8/2007 | Grossman |
| 2007/0191889 A1 | 8/2007 | Lang |
| 2007/0197895 A1 | 8/2007 | Nycz et al. |
| 2007/0203486 A1 | 8/2007 | Young |
| 2007/0203549 A1 | 8/2007 | Demarais et al. |
| 2007/0230757 A1 | 10/2007 | Trachtenberg et al. |
| 2007/0239099 A1 | 10/2007 | Goldfarb et al. |
| 2007/0244521 A1 | 10/2007 | Bornzin et al. |
| 2007/0249939 A1 | 10/2007 | Gerbi et al. |
| 2007/0287950 A1 | 12/2007 | Kjeken et al. |
| 2007/0295336 A1 | 12/2007 | Nelson et al. |
| 2007/0295337 A1 | 12/2007 | Nelson et al. |
| 2008/0015571 A1 | 1/2008 | Rubinsky et al. |
| 2008/0015628 A1 | 1/2008 | Dubrul et al. |
| 2008/0021371 A1 | 1/2008 | Rubinsky et al. |
| 2008/0027314 A1 | 1/2008 | Miyazaki et al. |
| 2008/0027343 A1 | 1/2008 | Fields et al. |
| 2008/0033340 A1 | 2/2008 | Heller et al. |
| 2008/0033417 A1 | 2/2008 | Nields et al. |
| 2008/0045880 A1 | 2/2008 | Kjeken et al. |
| 2008/0052786 A1 | 2/2008 | Lin et al. |
| 2008/0071262 A1 | 3/2008 | Azure |
| 2008/0071264 A1 | 3/2008 | Azure |
| 2008/0071265 A1 | 3/2008 | Azure |
| 2008/0086115 A1 | 4/2008 | Stoklund et al. |
| 2008/0097139 A1 | 4/2008 | Clerc et al. |
| 2008/0097422 A1 | 4/2008 | Edwards et al. |
| 2008/0103529 A1 | 5/2008 | Schoenbach et al. |
| 2008/0121375 A1 | 5/2008 | Richason et al. |
| 2008/0125772 A1 | 5/2008 | Stone et al. |
| 2008/0132826 A1 | 6/2008 | Shadduck et al. |
| 2008/0132884 A1 | 6/2008 | Rubinsky et al. |
| 2008/0132885 A1 | 6/2008 | Rubinsky et al. |
| 2008/0140064 A1 | 6/2008 | Vegesna |
| 2008/0146934 A1 | 6/2008 | Czygan et al. |
| 2008/0154259 A1 | 6/2008 | Gough et al. |
| 2008/0167649 A1 | 7/2008 | Edwards et al. |
| 2008/0171985 A1 | 7/2008 | Karakoca |
| 2008/0190434 A1 | 8/2008 | Tjong Joe Wai |
| 2008/0200911 A1 | 8/2008 | Long |
| 2008/0200912 A1 | 8/2008 | Long |
| 2008/0208052 A1 | 8/2008 | LePivert et al. |
| 2008/0210243 A1 | 9/2008 | Clayton et al. |
| 2008/0213331 A1 | 9/2008 | Gelfand et al. |
| 2008/0214986 A1 | 9/2008 | Ivorra et al. |
| 2008/0236593 A1 | 10/2008 | Nelson et al. |
| 2008/0249503 A1 | 10/2008 | Fields et al. |
| 2008/0255553 A1 | 10/2008 | Young et al. |
| 2008/0269586 A1 | 10/2008 | Rubinsky et al. |
| 2008/0269838 A1 | 10/2008 | Brighton et al. |
| 2008/0275465 A1 | 11/2008 | Paul et al. |
| 2008/0279995 A1 | 11/2008 | Schultheiss et al. |
| 2008/0281319 A1 | 11/2008 | Paul et al. |
| 2008/0283065 A1 | 11/2008 | Chang et al. |
| 2008/0288038 A1 | 11/2008 | Paul et al. |
| 2008/0294155 A1 | 11/2008 | Cronin |
| 2008/0294358 A1 | 11/2008 | Richardson |
| 2008/0300589 A1 | 12/2008 | Paul et al. |
| 2008/0306427 A1 | 12/2008 | Bailey |
| 2008/0312599 A1 | 12/2008 | Rosenberg |
| 2009/0018206 A1 | 1/2009 | Barkan et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024075 A1 | 1/2009 | Schroeppel et al. |
| 2009/0024085 A1 | 1/2009 | To et al. |
| 2009/0029407 A1 | 1/2009 | Gazit et al. |
| 2009/0030336 A1 | 1/2009 | Woo et al. |
| 2009/0036773 A1 | 2/2009 | Lau et al. |
| 2009/0038752 A1 | 2/2009 | Weng et al. |
| 2009/0062788 A1 | 3/2009 | Long et al. |
| 2009/0062792 A1 | 3/2009 | Vakharia et al. |
| 2009/0076496 A1 | 3/2009 | Azure |
| 2009/0076499 A1 | 3/2009 | Azure |
| 2009/0076500 A1 | 3/2009 | Azure |
| 2009/0076502 A1 | 3/2009 | Azure et al. |
| 2009/0081272 A1 | 3/2009 | Clarke et al. |
| 2009/0088636 A1 | 4/2009 | Lau et al. |
| 2009/0099544 A1 | 4/2009 | Munrow et al. |
| 2009/0105703 A1 | 4/2009 | Shadduck |
| 2009/0114226 A1 | 5/2009 | Deem et al. |
| 2009/0118725 A1 | 5/2009 | Auth et al. |
| 2009/0118729 A1 | 5/2009 | Auth et al. |
| 2009/0138014 A1 | 5/2009 | Bonutti |
| 2009/0143705 A1 | 6/2009 | Danek et al. |
| 2009/0157166 A1 | 6/2009 | Singhal et al. |
| 2009/0163904 A1 | 6/2009 | Miller et al. |
| 2009/0171280 A1 | 7/2009 | Samuel et al. |
| 2009/0177111 A1 | 7/2009 | Miller et al. |
| 2009/0186850 A1 | 7/2009 | Kiribayashi et al. |
| 2009/0192508 A1 | 7/2009 | Laufer et al. |
| 2009/0198227 A1 | 8/2009 | Prakash |
| 2009/0198231 A1 | 8/2009 | Esser et al. |
| 2009/0204005 A1 | 8/2009 | Keast et al. |
| 2009/0204112 A1 | 8/2009 | Kleyman |
| 2009/0209955 A1 | 8/2009 | Forster et al. |
| 2009/0216543 A1 | 8/2009 | Pang et al. |
| 2009/0221939 A1 | 9/2009 | Demarais et al. |
| 2009/0228001 A1 | 9/2009 | Pacey |
| 2009/0240247 A1 | 9/2009 | Rioux et al. |
| 2009/0247933 A1 | 10/2009 | Maor et al. |
| 2009/0248012 A1 | 10/2009 | Maor et al. |
| 2009/0269317 A1 | 10/2009 | Davalos |
| 2009/0270756 A1 | 10/2009 | Gamache et al. |
| 2009/0275827 A1 | 11/2009 | Aiken et al. |
| 2009/0281477 A1 | 11/2009 | Mikus et al. |
| 2009/0281540 A1 | 11/2009 | Blomgren et al. |
| 2009/0287081 A1 | 11/2009 | Grossman et al. |
| 2009/0292342 A1 | 11/2009 | Rubinsky et al. |
| 2009/0301480 A1 | 12/2009 | Elsakka et al. |
| 2009/0306544 A1 | 12/2009 | Ng et al. |
| 2009/0306545 A1 | 12/2009 | Elsakka et al. |
| 2009/0318849 A1 | 12/2009 | Hobbs et al. |
| 2009/0318905 A1 | 12/2009 | Bhargav et al. |
| 2009/0326366 A1 | 12/2009 | Krieg |
| 2009/0326436 A1 | 12/2009 | Rubinsky et al. |
| 2009/0326561 A1 | 12/2009 | Carroll et al. |
| 2009/0326570 A1 | 12/2009 | Brown |
| 2010/0004623 A1 | 1/2010 | Hamilton, Jr. et al. |
| 2010/0016783 A1 | 1/2010 | Bourke, Jr. et al. |
| 2010/0023004 A1 | 1/2010 | Francischelli et al. |
| 2010/0030211 A1 | 2/2010 | Davalos et al. |
| 2010/0036291 A1 | 2/2010 | Darlington et al. |
| 2010/0049190 A1 | 2/2010 | Long et al. |
| 2010/0056926 A1 | 3/2010 | Deckman et al. |
| 2010/0057074 A1 | 3/2010 | Roman et al. |
| 2010/0057076 A1 | 3/2010 | Behnke et al. |
| 2010/0069921 A1 | 3/2010 | Miller et al. |
| 2010/0079215 A1 | 4/2010 | Brannan et al. |
| 2010/0082022 A1 | 4/2010 | Haley et al. |
| 2010/0082023 A1 | 4/2010 | Brannan et al. |
| 2010/0082024 A1 | 4/2010 | Brannan et al. |
| 2010/0082025 A1 | 4/2010 | Brannan et al. |
| 2010/0082083 A1 | 4/2010 | Brannan et al. |
| 2010/0082084 A1 | 4/2010 | Brannan et al. |
| 2010/0087813 A1 | 4/2010 | Long |
| 2010/0090696 A1 | 4/2010 | Deimling |
| 2010/0100093 A1 | 4/2010 | Azure |
| 2010/0106025 A1 | 4/2010 | Sarfaty et al. |
| 2010/0106047 A1 | 4/2010 | Sarfaty et al. |
| 2010/0121173 A1 | 5/2010 | Sarfaty et al. |
| 2010/0130975 A1 | 5/2010 | Long |
| 2010/0152725 A1 | 6/2010 | Pearson et al. |
| 2010/0160850 A1 | 6/2010 | Ivorra et al. |

(56) References Cited

U.S. PATENT DOCUMENTS

| | | |
|---|---|---|
| 2010/0168735 A1 | 7/2010 | Deno et al. |
| 2010/0174282 A1 | 7/2010 | Demarais et al. |
| 2010/0179436 A1 | 7/2010 | Sarfaty et al. |
| 2010/0179530 A1 | 7/2010 | Long et al. |
| 2010/0191112 A1 | 7/2010 | Demarais et al. |
| 2010/0191235 A1 | 7/2010 | Moshe et al. |
| 2010/0196984 A1 | 8/2010 | Rubinsky et al. |
| 2010/0204560 A1 | 8/2010 | Salahieh et al. |
| 2010/0204638 A1* | 8/2010 | Hobbs ............... A61B 18/148 604/20 |
| 2010/0211061 A1 | 8/2010 | Leyh |
| 2010/0222677 A1 | 9/2010 | Placek et al. |
| 2010/0228247 A1 | 9/2010 | Paul et al. |
| 2010/0241117 A1 | 9/2010 | Paul et al. |
| 2010/0249771 A1 | 9/2010 | Pearson et al. |
| 2010/0250209 A1 | 9/2010 | Pearson et al. |
| 2010/0255795 A1 | 10/2010 | Rubinsky et al. |
| 2010/0256624 A1 | 10/2010 | Brannan et al. |
| 2010/0256628 A1 | 10/2010 | Pearson et al. |
| 2010/0256630 A1 | 10/2010 | Hamilton, Jr. et al. |
| 2010/0261994 A1 | 10/2010 | Davalos et al. |
| 2010/0262067 A1 | 10/2010 | Chornenky et al. |
| 2010/0268223 A1 | 10/2010 | Coe et al. |
| 2010/0268225 A1 | 10/2010 | Coe et al. |
| 2010/0286690 A1 | 11/2010 | Paul et al. |
| 2010/0292686 A1 | 11/2010 | Rick et al. |
| 2010/0298822 A1 | 11/2010 | Behnke |
| 2010/0298823 A1 | 11/2010 | Cao et al. |
| 2010/0298825 A1 | 11/2010 | Slizynski et al. |
| 2010/0331758 A1 | 12/2010 | Davalos et al. |
| 2010/0331911 A1 | 12/2010 | Kovalcheck et al. |
| 2011/0009860 A1 | 1/2011 | Chornenky et al. |
| 2011/0015630 A1 | 1/2011 | Azure |
| 2011/0017207 A1 | 1/2011 | Hendricksen et al. |
| 2011/0021970 A1 | 1/2011 | Vo-Dinh et al. |
| 2011/0034209 A1 | 2/2011 | Rubinsky et al. |
| 2011/0054458 A1 | 3/2011 | Behnke |
| 2011/0064671 A1 | 3/2011 | Bynoe |
| 2011/0082362 A1 | 4/2011 | Schmidt et al. |
| 2011/0082414 A1 | 4/2011 | Wallace |
| 2011/0098695 A1 | 4/2011 | Brannan |
| 2011/0105823 A1 | 5/2011 | Single, Jr. et al. |
| 2011/0106221 A1 | 5/2011 | Neal et al. |
| 2011/0112434 A1 | 5/2011 | Ghabrial et al. |
| 2011/0112531 A1 | 5/2011 | Landis et al. |
| 2011/0118721 A1 | 5/2011 | Brannan |
| 2011/0118727 A1 | 5/2011 | Fish et al. |
| 2011/0118729 A1 | 5/2011 | Heeren et al. |
| 2011/0118732 A1 | 5/2011 | Rubinsky et al. |
| 2011/0118734 A1 | 5/2011 | Auld et al. |
| 2011/0130834 A1 | 6/2011 | Wilson et al. |
| 2011/0135626 A1 | 6/2011 | Kovalcheck |
| 2011/0144524 A1 | 6/2011 | Fish et al. |
| 2011/0144562 A1 | 6/2011 | Heeren et al. |
| 2011/0144635 A1 | 6/2011 | Harper et al. |
| 2011/0144638 A1 | 6/2011 | Heeren et al. |
| 2011/0144641 A1 | 6/2011 | Dimalanta, Jr. et al. |
| 2011/0144657 A1 | 6/2011 | Fish et al. |
| 2011/0152678 A1 | 6/2011 | Aljuri et al. |
| 2011/0152906 A1 | 6/2011 | Escudero et al. |
| 2011/0152907 A1 | 6/2011 | Escudero et al. |
| 2011/0160514 A1 | 6/2011 | Long et al. |
| 2011/0172659 A1 | 7/2011 | Brannan |
| 2011/0178570 A1 | 7/2011 | Demarais |
| 2011/0202052 A1 | 8/2011 | Gelbart et al. |
| 2011/0202053 A1 | 8/2011 | Moss et al. |
| 2011/0207758 A1 | 8/2011 | Sobotka et al. |
| 2011/0208096 A1 | 8/2011 | Demarais et al. |
| 2011/0208180 A1 | 8/2011 | Brannan |
| 2011/0217730 A1 | 9/2011 | Gazit et al. |
| 2011/0230874 A1 | 9/2011 | Epstein et al. |
| 2011/0245756 A1 | 10/2011 | Arora et al. |
| 2011/0251607 A1 | 10/2011 | Kruecker et al. |
| 2011/0282354 A1 | 11/2011 | Schulte et al. |
| 2011/0288545 A1 | 11/2011 | Beebe et al. |
| 2011/0306971 A1 | 12/2011 | Long |
| 2012/0034131 A1 | 2/2012 | Rubinsky et al. |
| 2012/0046658 A1 | 2/2012 | Kreindel |
| 2012/0059255 A1 | 3/2012 | Paul et al. |
| 2012/0071872 A1 | 3/2012 | Rubinsky et al. |
| 2012/0071874 A1 | 3/2012 | Davalos et al. |
| 2012/0085649 A1 | 4/2012 | Sano et al. |
| 2012/0089009 A1 | 4/2012 | Omary et al. |
| 2012/0090646 A1 | 4/2012 | Tanaka et al. |
| 2012/0095459 A1 | 4/2012 | Callas et al. |
| 2012/0109122 A1 | 5/2012 | Arena et al. |
| 2012/0130289 A1 | 5/2012 | Demarais et al. |
| 2012/0150172 A1 | 6/2012 | Ortiz et al. |
| 2012/0165813 A1 | 6/2012 | Lee et al. |
| 2012/0179091 A1 | 7/2012 | Ivorra et al. |
| 2012/0220999 A1 | 8/2012 | Long |
| 2012/0226218 A1 | 9/2012 | Phillips et al. |
| 2012/0226271 A1 | 9/2012 | Callas et al. |
| 2012/0265186 A1 | 10/2012 | Burger et al. |
| 2012/0277741 A1 | 11/2012 | Davalos et al. |
| 2012/0303012 A1 | 11/2012 | Leyh |
| 2012/0303020 A1 | 11/2012 | Chornenky et al. |
| 2012/0310236 A1 | 12/2012 | Placek et al. |
| 2012/0310237 A1 | 12/2012 | Swanson |
| 2013/0035921 A1 | 2/2013 | Rodriguez-Ponce et al. |
| 2013/0041436 A1 | 2/2013 | Ruse et al. |
| 2013/0072858 A1 | 3/2013 | Watson et al. |
| 2013/0090646 A1 | 4/2013 | Moss et al. |
| 2013/0184702 A1 | 7/2013 | Neal et al. |
| 2013/0196441 A1 | 8/2013 | Rubinsky et al. |
| 2013/0230895 A1 | 9/2013 | Koblizek et al. |
| 2013/0238062 A1 | 9/2013 | Ron Edoute et al. |
| 2013/0253415 A1 | 9/2013 | Sano et al. |
| 2013/0261389 A1 | 10/2013 | Long |
| 2013/0281968 A1 | 10/2013 | Davalos et al. |
| 2013/0345697 A1 | 12/2013 | Garcia et al. |
| 2014/0039489 A1 | 2/2014 | Davalos et al. |
| 2014/0081255 A1 | 3/2014 | Johnson et al. |
| 2014/0088578 A1 | 3/2014 | Rubinsky et al. |
| 2014/0107643 A1 | 4/2014 | Chornenky et al. |
| 2014/0121663 A1 | 5/2014 | Pearson et al. |
| 2014/0163551 A1 | 6/2014 | Maor et al. |
| 2014/0296844 A1 | 10/2014 | Kevin et al. |
| 2014/0309579 A1 | 10/2014 | Rubinsky et al. |
| 2014/0378964 A1 | 12/2014 | Pearson |
| 2015/0032105 A1 | 1/2015 | Azure |
| 2015/0066013 A1 | 3/2015 | Salahieh et al. |
| 2015/0066020 A1 | 3/2015 | Epstein et al. |
| 2015/0088120 A1 | 3/2015 | Garcia et al. |
| 2015/0088220 A1 | 3/2015 | Callas et al. |
| 2015/0112333 A1 | 4/2015 | Chorenky et al. |
| 2015/0126922 A1 | 5/2015 | Willis |
| 2015/0141984 A1 | 5/2015 | Loomas et al. |
| 2015/0164584 A1 | 6/2015 | Davalos et al. |
| 2015/0173824 A1 | 6/2015 | Davalos et al. |
| 2015/0196351 A1 | 7/2015 | Stone et al. |
| 2015/0201996 A1 | 7/2015 | Rubinsky et al. |
| 2015/0265349 A1 | 9/2015 | Moss et al. |
| 2015/0320488 A1 | 11/2015 | Moshe et al. |
| 2015/0327944 A1 | 11/2015 | Neal et al. |
| 2016/0022957 A1 | 1/2016 | Hobbs et al. |
| 2016/0066977 A1 | 3/2016 | Neal et al. |
| 2016/0074114 A1 | 3/2016 | Pearson et al. |
| 2016/0143698 A1 | 5/2016 | Garcia et al. |

FOREIGN PATENT DOCUMENTS

| | | |
|---|---|---|
| AU | 2003227960 A1 | 12/2003 |
| AU | 2005271471 A2 | 2/2006 |
| AU | 2006321570 A1 | 6/2007 |
| AU | 2006321574 A1 | 6/2007 |
| AU | 2006321918 A1 | 6/2007 |
| AU | 2012255070 A1 | 1/2014 |
| CA | 2297846 A1 | 2/1999 |
| CA | 2378110 A1 | 2/2001 |
| CA | 2445392 A1 | 11/2002 |
| CA | 2458676 A1 | 3/2003 |
| CA | 2487284 A1 | 12/2003 |
| CA | 2575792 A1 | 2/2006 |

(56) References Cited

FOREIGN PATENT DOCUMENTS

| | | |
|---|---|---|
| CA | 2631940 A1 | 6/2007 |
| CA | 2631946 A1 | 6/2007 |
| CA | 2632604 A1 | 6/2007 |
| CA | 2751462 A1 | 11/2010 |
| CN | 1525839 A | 9/2004 |
| CN | 101534736 A | 9/2009 |
| CN | 102238921 A | 11/2011 |
| CN | 102421386 A | 4/2012 |
| DE | 4000893 A1 | 7/1991 |
| DE | 60038026 T2 | 2/2009 |
| EP | 0218275 A1 | 4/1987 |
| EP | 0339501 A2 | 11/1989 |
| EP | 0378132 A2 | 7/1990 |
| EP | 0528891 A1 | 3/1993 |
| EP | 0533511 A1 | 3/1993 |
| EP | 0935482 A1 | 8/1999 |
| EP | 0998235 A1 | 5/2000 |
| EP | 1011495 A1 | 6/2000 |
| EP | 1061983 A1 | 12/2000 |
| EP | 1196550 A2 | 4/2002 |
| EP | 1207797 A1 | 5/2002 |
| EP | 1406685 A1 | 4/2004 |
| EP | 1424970 A2 | 6/2004 |
| EP | 1439792 A1 | 7/2004 |
| EP | 1442765 A1 | 8/2004 |
| EP | 1462065 A2 | 9/2004 |
| EP | 1493397 A1 | 1/2005 |
| EP | 1506039 A1 | 2/2005 |
| EP | 1791485 A2 | 6/2007 |
| EP | 1962708 A2 | 9/2008 |
| EP | 1962710 A2 | 9/2008 |
| EP | 1962945 A1 | 9/2008 |
| EP | 2373241 A1 | 10/2011 |
| EP | 2381829 A1 | 11/2011 |
| EP | 2413833 A1 | 2/2012 |
| EP | 2429435 A1 | 3/2012 |

OTHER PUBLICATIONS

Sharma, et al, Poloxamer 188 decrease susceptibility of artificial lipid membranes to electroporation, Biophysical Journal, 1996, vol. 71, pp. 3229-3241.
Blad, Baldetorp, Impedance spectra of tumour tissue in comparison with normal tissue; a possible clinical application for electrical impedance tomography, Physiol. Meas., 1996, 17, pp. A105-A115.
Ho, Mittal, Electroporation of cell membranes: a review, Critical Reviews in Biotechnology, 1996, 16(4), pp. 349-362.
Gilbert, et al, Rapid report novel electrode designs for electrochemotherapy, Biochimica et Biophysica Acta, Feb 11, 1997, 1134, pp. 9-14.
Zlotta, et al, Possible mechanisms fo action of transsurethral needle ablation of the prostate on benign prostatic hyperplasia systems: A neurohistochemical study, Journal of Urology, Mar 1997, vol. 157, No. 3, pp. 894-899.
Duraiswami et al, Solution of electrical impedance tomography equations using boundary element methods, Boundary Element Technology XII, Apr. 1997, pp. 227-237.
Fox, Nicholls, Sampling conductivity images via MCMC, Auckland University, Auckland, New Zealand.
Naslund, Transurethral needle ablation of the prostate, Urology, Aug 1997, vol. 50, No. 2, pp. 167-172.
Boone, et al, Review imaging with electricity: Report of the European concerted action on impedance tomography, Journal of Medical Engineering & Technology, Nov. 1997, vol. 21, No. 6, pp. 201-232.
Lurquin, Review: Gene transfer by electroporation, Molecular Biotechnology, 1997, vol. 7, pp. 5-31.
Hapala, Breaking the barrier: methods for reversible permeabilization of cellular membranes, Critical Reviews in Biotechnology, 1997, 17(2), pp. 105-122.

Duraiswami, et al, Boundary element techniques for efficient 2-D and 3-D electrical impedance tomography, Chemical Engineering Science, 1997, vol. 52, No. 13, pp. 2185-2196.
Pinero, et al, Apoptotic and necrotic cell death are both induced by electroporation in HL60 human promyeloid leukaemia cells, Apoptosis, 1997, 2, pp. 330-336.
Miklavcic, et al, The importance of electric field distribution for effective in vivo electroporation of tissues, Biophysical Journal, May 1998, vol. 74, pp. 2152-2158.
Issa, et al, Recent Reports: The TUNA procedure for BPH: Review of the technology, Infections in Urology, Jul. 1998.
Lundqvist, et al, Altering the biochemical state of individual cultured cells and organelles with ultramicroelectrodes, Proc. Natl. Acad. Sci. USA, Sep. 1998, Vo. 95, pp. 10356-10360.
Issa, et al, Specialty Surgery: The TUNA procedure for BPH: Basic procedure and clinical results, Infections in Urology, Sep. 1998.
Dev, et al, Sustained local delivery of heparin to the rabbit arterial wall with an electroporation catheter, Catheterization and Cardiovascular Diagnosis, 1998, 45, pp. 337-345.
Duraiswami, et al, Efficient 2D and3D electrical impedance tomography using dual reciprocity boundary element techniques, Engineering Analysis with Boundary Elements, 1998, 22, pp. 13-31.
Mir, et al, Effective treatment of cutaneous and subcutaneous malignant tumors by electrochemotherapy, 1998, British Journal of Cancer, 77 (12), pp. 2336-2342.
Sersa, et al, Tumor blood flow modifying effect of electrochemotherapy with Bleomycin, Anticancer Research, 1999, 19, pp. 4017-4022.
Thompson, et al, To determine whether the temperature of 2% lignocaine gel affects the initial discomfort which may be associated with its instillation into the male urethra, BJU International, 1999, 84, pp. 1035-1037.
Gumerov, et al, The dipole approximation method and its coupling with the regular boundar yelement method for efficient electrical impedance tomography, BETECH 99.
Yang, et al, Dielectric properties of human luekocyte subpopulations determined by electrorotation as a cell separation criterion, Jun. 1999, vol. 76, pp. 3307-3014.
Huang, Rubinsky, Micro-electroporation: improving the efficiency and understanding of electrical permeabilization of cells, Biomedical Microdevices, 1999, 2:2, pp. 145-150.
Mir, Orlowski, Mechanisms of electrochemotherapy, Advanced Drug Delivery Reviews, 1999, 35, pp. 107-118.
Jaroszeski, et al, In vivo gene delivery by electroporationi, Advanced Drug Delivery Reviews, 1999, 35, pp. 131-137.
Gehl, et al, In vivo electroporation of skeletal muscle: threshold, efficacy and relation to electric field distribution, Biochimica et Biophysica Acta, 1999, 1428, pp. 233-240.
Heller, et al, Clinical applications of electrochemotherapy, Advanced Drug Delivery Reviews, 1999, 35, 119-129.
Holder, et al, Low-Frequency System, Assessment and calibration of a low-frequency impedance tomography (EIT), optimized for use in imaging brain function in ambulant human subjects, Annals New York Academy Sciences, pp. 512-519.
Dev, et al, Medical applications of electroporation, IEEE Transactions on Plasma Science, Feb. 2000, vol. 28, No. 1, pp. 206-222.
Ivanusa, et al, MRI macromolecular contrast agents as indicators of changed tumor blood flow, Radiol Oncol, 2001, 35, 2, pp. 139-147.
Ermolina, et al, Study of normal and malignant white blood cells by time domain dielectric spectroscopy, IEEE Transactions on Dielectrics and Electrical Insulation, Apr. 2001, vol. 8, No. 2, pp. 253-261.
Carson, et al, Improving patient satisfaction, BPH management strategies, Supplement to Urology Times, May 2001, Vo. 29, Suppl. 1, pp. 1-22.
Beebe, et al, Nanosecond pulsed electric field (nsPEF) effects on cells and tissues: Apoptosis induction and tumor growth inhibition, IEEE, 2002, pp. 211-215.
N/a, When patient satisfaction is your goal, Precision Office TUNA System, VidaMed, Inc.
Chandrasekar, et al, Transurethral needle ablation of the prostate (TUNA)—A prospective study, six year follow up, pp. 1210.

(56) References Cited

OTHER PUBLICATIONS

N/a, Highlights from worldwide clinical studies, Transurethral needle ablation (TUNA), Vidamed's Office TUNA System, VidaMed, Inc., pp. 1-4.
Schoenbach, et al, Intracellular effect of ultrashort electrical pulses, Bioelectromagnetics, 2001, 22, pp. 440-448.
Cemazar et al, Electroporation of human microvascular endothelial cells: evidence for an anti-vascular mechanism of electrochemotherapy, British Journal of Cancer, 2001, 84, 4, pp. 565-570.
Kotnik, et al, Cell membrane electropermeabilization by symmetrical biopolar rectangular pulses, Part I. Increased efficiency of permeabilization, Bioelectrochemistry, 2001, 54, pp. 83-90.
Kotnik, et al, Cell membrane electropermeabilization by symmetrical biopolar rectangular pulses, Part II. Reduced electrolytic contamination, Bioelectrochemistry, 2001, 54, pp. 91-95.
Lebar, Miklavcic, Cell electropermeabilization to small molecules in vitro: control by pulse parameters, Radiol Oncol, 2001, 35, 3, pp. 193-202.
Naslund, Cost-effectiveness of minimally invasive treatments and transurethral resection (TURP) in benign prostatic hyperplasia (BPH), Unveristy of Maryland School of Medicine, 2001, pp. 1213.
Davalos, et al, A feasibility study for electrical impedance tomography as a means to montior tissue electroporatioin for molecular medicien, IEEE Transactions on Biomedical Engineering, Apr. 2002, vol. 49, No. 4, pp. 400-403.
Jossinet, et al, Electrical impedance end-tomography: Imaging tissue from inside, IEEE Transactions on Medical Imaging, Jun. 2002, vol. 21, No. 6, pp. 560-565.
Lebar, et al, Inter-pulse interval between rectangular voltage pulses affects electroporation threshold of artifice lipid bilayers, IEEE Transactions on Nanobioscience, Sep. 2002, vol. 1, No. 3, pp. 116-120.
Sersa, et al, Reduced blood flow and oxygenation in SA-I tumors after electrochemotherapy with cisplatin, 2003, 87, pp. 1047-1054.
Davalos, Real-time imaging for molecular medicine through electrical impedance tomography of electroporation, Dissertation, University of California, Berkeley.
Szot, et al, 3D in vitro bioengineered tumors based on collagen I hydrogels, Biomaterials, Nov. 2011, 32(31), pp. 7905-7912.
Bastista, et al, The use of whole organ decellularization for the generation of a vascularized liver organoid, Hepatology, 2011, vol. 53, No. 2, pp. 604-617.
Sano, et al, Modeling and development fo a low frequency contactless dielectrophoresis (cDEP) platform to sort cancer cells from dilute whole blood samples, Biosensors and Bioelectronics, 2011, pp. 1-8.
Charpentier, et al, Irreversible electroporation of the liver an dliver hilum in swine, HBP, 2011, 13, pp. 168-173.
Sankaranarayanan, et al, Effect of irreversible electroporation on cell proliferation in fibroblasts, Proc. ESA Annual Meeting on Electrostatics, 2011, pp. 1-8.
Sano, et al, Contactless dielectrophoretic spectroscopy: Examination of the dielectric properties of cells found in blood, Electrophoresis, 2011, 32, pp. 3164-3171.
Chen, et al, Classification of cell types using a microfluidic device for mechanical and electrical measurements on single cells, Lab Chip, 2011, 11 , pp. 3174-3181.
Rebersek, Miklavcic, Advantages and disadvantages of different concepts of electroporation pulse generation, Automatika, 2011, 52, 1, pp. 12-19.
Ben-David, et al, Characterization of irreversible electroporaiton ablation in in vivo porcine liver, AJR, Jan. 2012, 198, pp. W62-W68.
Appelbaum, et al, US findings after irreversible electroporation ablation: Radiologic-pathologic correlation, Radiology, Jan. 2012, vol. 262, No. 1, pp. 117-125.
Salmanzadeh, et al, Dielectrophoretic differentiation of mouse ovarian surface epithelial cells, macrophages, and fibroblasts using contactless dielectrophoresis, Biomicrofluidics, Apr. 3, 2012, 6, 024104, pp. 1-13.
Neal, et al, Experimental characterization and numerical modeling of tissue electrical conductivity during pulsed electric fields for irreversible electroporation treatment planning, IEEE Transactions on Biomedical Engineering, Apr. 2012, vol. 59, No. 4, pp. 1076-1085.
Du Pre, et al, Minimal coronary artery damage by myocardial electroporation ablation, European Society of Cardiology, Europace, May 31, 2012, pp. 1-6.
Wittkampf, et al, Myocradial lesion depth with circular electroporation ablation, Circ Arrhythm Electrophysiol, 2012, 5, pp. 581-586.
Arena, et al, Phase change electrodes for reducing joule heating during irreversible electroporation, Proceedings of the ASME 2012 Summer Bioengineering Conference, Jun. 20, 2012, pp. 1-2.
Garcia, et al, Towards a predictive model of electroporation-based therapies using pre-pulse electrical measurements, 34th Annual International Conference of the IEEE EMBS, Aug. 28, 2012, pp. 2575-2578.
Hjouj, et al, MRI study on reversible and irreversible electroporation induced blood brain barrier disruption, Aug. 10, 2012, PLOS One, vol. 7, 8, e42817, pp. 1-9.
Martin, et al, Irreversible electroporation therapy in the management of locally advanced pancreatic adenocarcinoma, American College of Surgeons, Sep. 2012, vol. 215, No. 3, pp. 361-369.
Weaver, et al, A brief overview of electroporation pulse strength-duration space: A region where additional intracellular effects are expected, Bioelectrochemistry, Oct. 2012, 87, pp. 236-243.
Arena, et al, A three-dimensional in vitro tumor platform for modeling therapeutic irreversible electroporation, Biophysical Journal, Nov. 2012, vol. 103, pp. 2033-2042.
Garcia, et al, 7.0-T magnetic resonance imaging characterization of acute blood-brain-barrier disruption achieved with intracranial irreversible electroporation, PLOS One, vol. 7, 11, pp. 1- 8.
Arena, et al, Towards the development of latent heat storage electrodes for electroporation-based therapies, Applied Physics Letters, 2012, 101, 083902, pp. 1-4.
Cannon, et al, Safety and early efficacy of irreversible electroporation for hepatic tumors in proximity to vital structures, Journal of Surgical Oncology, 2012, pp. 1-6.
Bagla, Papadouris, Percutaneous irreversible electroporation of surgically unresectable pancreatic cancer: A case report, J Vasc Intery Radiol, 2012, 23, pp. 142-145.
Phillips, et al, Irreversible electroporation on the small intestine, British Journal of Cancer, 2012, pp. 1-6.
Mahnic-Kalamiza, et al, Educational application for visualization and analysis of electric field strength in multiple electrode electroporation, BMC Medical Education, 2012, 12, 102, pp. 1-13.
Kingham, et al, Ablation of perivascular hepatic malignant tumors with irreversible electroporation, J Am Coll Surg, 2012, 215, pp. 379-387.
Salmanzadeh, et al, Investigating dielectric properties of different stages of syngeneic murine ovarian cancer cells, Biomicrofluidics, Jan. 23, 2013, 7, 011809, pp. 1-12.
Faroja, et al, Irreversible electroporation ablation: Is all the damage non-thermal?, Radiology, Feb. 2013, vol. 266, No. 2, pp. 462-470.
Fong, et al, Modeling ewing sarcoma tumors in vitro with 3D scaffolds, PNAS, Apr. 16, 2013, vol. 110, No. 15, pp. 6500-6505.
Garcia, et al, Position paper concerning the use of Angiodynamics' nanoknife system for treatment of brain gliomas, Virgina Tech—Wake Forest University, May 22, 2013, pp. 1-46.
Salmanzadeh, et al, Sphingolipid metabolites modulate dielectric characteristics of cells in a mouse ovarian cancer progression model, Integr Biol, Jun. 2013, 5, 6, pp. 843-852.
Polak, et al, On the electroporation thresholds of lipid bilayers: Molecular dynamics simulation investigations, J Membrane Biol, Jun. 13, 2013, 246, pp. 843-850.
Jiang, et al, Membrane-targeting approaches for enhanced cancer cell destruction with irreversible electroporation, Annuals of Biomedical Engineering, Aug. 15, 2013.

(56) References Cited

OTHER PUBLICATIONS

Bayazitoglu, et al, An overview of nanoparticle assisted laser therapy, International Journal of Heat and Mass Transfer, Sep. 11, 2013, 67, pp. 469-486.
Rossmeisl, Jr., et al, Pathology of non-thermal irreversible electroporation (N-TIRE)-induced ablation of the canine brain, Journal of Veterinary Science, 2013, 14, 4, pp. 433-440.
Lu, et al, Irreversible electroporation: Ready for prime time?, Techniques in Vascular and Interventional Radiology, 2013, 16, pp. 277-286.
Dunki-Jacobs, et al, Evaluation of resistance as a measure of successful tumor ablation during irreversible electroporation of the pancreas, American College of Surgeons, Feb. 2014, vol. 218, No. 2, pp. 179-187.
Son, et al, Basic features of a cell electroporation model: illustrative behavior for tw overy different pulses, J Membrane Biol, Jul. 22, 2014, 247, pp. 1209-1228.
Neal, et al, An "Off-the-Shelf" system for intraprocedural electrical current evaluation and monitoring of irreversible electroporation therapy, Cardiovasc Intervent Radiol, Feb. 27, 2014.
Sano, et al, In-vtro bipolar nano- and microsecond electro-pulse bursts for irreversible electroporation therapies, Bioelectrochemistry, Aug. 4, 2014, 100, pp. 69-79.
Rossmeisl, New treatment modalities for brain tumors in dogs and cats, Vet Clin Small Anim, 2014, 44, pp. 1013-1038.
Chen, et al, Preclinical study of locoregional therapy of hepatocellular carcinoma by bioelectric ablation with microsecond pulsed electric fields (usPEFs), Scientific Reports, Apr. 2015, 5, 9851, pp. 1-10.
Trimmer, et al, Minimally invasive percutaneous treatment of small renal tumors with irreversible electroporation: a single-center experience, J Vasc Intery Radiol, 2015, 26: pp. 1465-1471.
Eppich, et al, Pulsed electric fields for seletion of hematopoietic cells and depletion of tumor cell contaminants, Nature America, Aug. 2000, vol. 18, pp. 882-887.
Mir, Therapeutic perspectives of in vivo cell electropermeabilization, Bioelectrochemistry, 2000, 53, pp. 1-10.
Al-Khadra, et al, The role of electroporation in defibrillation, Circulation Research, Oct. 27, 2000, 87, pp. 797-804.
Miklavcic, et al, A validated model of in vivo electric field distribution in tissues for electrochemotherapy and for DNA electrotransfer for gene therapy, Biochimica et Biophysica Acta, 2000, 1523, pp. 73-83.
Rubinsky, Cryosurgery, Annu. Rev. Biomed. Eng. 2000, 2, pp. 157-187.
Jaroszeski, et al, In vivo gene delivery by electroporation, Advanced Drug Delivery Reviews, 1999, 35, pp. 131-137.
Coates, et al, The electric discharge of the electric eel, Electrophorus electricus (Linnaeus), Zoologica: New York Zoological Society, pp. 1-32.
Lynn, et al, A new method for the generation and use of focused ultrasound in experimental biology, pp. 179-193.
Clark, et al, The Electrical Properties of Resting and Secreting Pancreas, pp. 247-260.
Neumann, Rosenheck, Permeability changes induced by electric impulses in vesicular membranes, J. Membrane Biol., 1972, 10, pp. 279-290.
Crowley, Electrical breakdown of bimolecular lipid membranes as an electromechanical instability, Biophysical Journal, 1973, vol. 13, 711-724.
Zimmermann, et al, Dielectric breakdown of cell membranes, Biophysical Journal, 1974, vol. 14, pp. 881-899.
Organ, Electrophysiologic principles of radiofrequency lesion making, Appl. Neurophysiol., 1976, 39, pp. 69-76.
Kinosita, Jr., Tsong, Hemodialysis of human erythrocytes by a transient electric field, Biochemistry, 1977, vol. 74, No. 5, pp. 1923-1927.
Kinsoita, Jr., Tsong, Formation and resealing of pores of controlled sizes in human erythrocyte membrane, Aug. 1977, vol. 268, pp. 438-441.
Kinosita, Jr., Tsong, Voltage-induced pore formation and hemolysis of human erythrocytes, Biochimica et Biophysica Acta, 1977, pp. 227-242.
Baker, Knight, Calcium-dependent exocytosis in bovine adrenal medullary cells with leaky plasma membranes, Nature, Dec. 1978, vol. 276, pp. 620-622.
Gauger, Bentrup, A study of dielectric membrane breakdown in the Fucus egg, J. Membrane Biol., 1979, 48, pp. 249-264.
Erez, Shitzer, Controlled destruction and temperature distributions in biological tissues subjected to monactive electrocoagulation, Transactions of theASME, Feb. 1980, vol. 102, pp. 42-49.
Neumann, et al, Gene transfer into mouse lyoma cells by electroporation in high electric fields, The EMBO Journal, 1982, vol. 1, No. 7, pp. 841-845.
Seibert, et al, Clonal variation of MCF-7 breast cancer cells in vitro and in athymic nude mice, Cancer Research, May 1983, 43, pp. 2223-2239.
Brown, Phototherapy of tumors, World J. Surg., 1983, 7, 700-709.
Onik, et al, Ultraonic characteristics of frozen liver, Cryobiology, 1984, 21, pp. 321-328.
Gilbert, et al, The use of ultrsound imaging for monitoring cryosurgery, IEEE Frontiers of Engineering and computing in Health Care, 1984, pp. 107-111.
Onik, et al, Sonographic monitoring of hepatic cryosurgery in an experimental animal model, AJR, May 1985, 144, pp. 1043-1047.
Griffiths, The importance of phase measurement in e lectrical impedance tomography, Phys. Med. Biol., Nov. 1987, vol. 32, No. 11, pp. 1435-1444.
Okino, Mohri, Effects of high-voltage electrical impulse and an anticancer drug on in vivo growing tumors, Jpn. J. Cancer Res., Dec. 1987, 78, pp. 1319-1321.
Kinosita, Jr. et al, Electroporation of cell membrane visualized under a pulsed-laser fluorescence microscope, Biophys. J., Jun. 1988, vol. 53, pp. 1015-1019.
Amasha, et al, Quantitative assessment of impedance tomography for temperature measurements in microwave hyperthermia, Clin. Phys. Physiol. Meas., 1988, vol. 9, Suppl. A, pp. 49-53.
Asmai, et al, Dielectric properties of mouse lymphocytes and erythrocytes, Biochimica et Biophysica Acta, 1989, 1010, pp. 49-55.
Griffiths, Zhang, A dual-frequency electrical impedance tomography system, Phys. Med. Biol., 1989, vol. 34, No. 10, pp. 1465-1476.
Rowland, et al, Transvenous ablation of atrioventricular conduction with a low energy power source, Br Heart J, 1989, 62, pp. 361-366.
Marsazalek, et al, Schwan equation and transmembrane potential induced by alternating electric field, Biophysical Journal, Oct. 1990, vol. 58, pp. 1053-1058.
Tekle, et al, Electroporation by using bipolar oscillating electric field: An improved method for DNA transfection of NIH 3T3 cells, Biochemistry, May 1991, vol. 88, pp. 4230-4234.
Mir, et al, Electrochemotherapy potentiation of antitumour effect of bleomycin by local electric pulses, Eur. J. Cancer, 1991, vol. 27, No. 1, pp. 68-72.
Mir, et al, Electrochemotherapy, a novel antitumor treatment: first clinical trial, Cancerology, 1991, 313, pp. 613-618.
Narayan, Dahiya, Establishment and characterization of a human primay prostatic adenocarcinoma cell line (ND-1_, The Journal of Urology, Nov. 1992, vol. 148, pp. 1600-1604.
Griffiths, et al, Measurement of pharyngeal transit time by electrical impedance tomography, Clin. Phys. Physiol. Meas., 1993, vol. 13, Suppl. A, pp. 197-200.
Rols, et al, Highly efficient transfection of mammalian cells by electric field pulses application to large volumes of cell culture by using a flow system, Eur. J. Biochem., 1992, 205, pp. 115-121.
Brown, et al, Blood flow imaging using electrical impedance tomography, Clin. Phys. Physiol. Meas., 1992, vol. 13, Suppl. A, pp. 175-179.
Foster, et al, Production of prostatic lesions in canines usign transrectally administered high-intensity focused ultrasound, Eur Urol, 1993, pp. 330-336.
Shiina, et al, Percutaneous ethanol injection therapy for hepatocellular carcinoma: Results in 146 patients, AJR, May 1993, 160, pp. 1023-1028.

(56) References Cited

OTHER PUBLICATIONS

Salford, et al, A new brain tumour therapy combining bleomycin with in vivo electropermeabilization, Biochemical and Biohysical Research Communications, Jul. 30, 1993, vol. 194, No. pp. 938-943.
Glidewell, NG, The use of magnetic resonance imaging data and the inclusion of anisotropic regions in electrical impedance tomography, ISA, 1993, pp. 251-257.
Gascoyne, et al, Membrane changes accompanying the induced differentiation of Friend murine erythroleukemia cells studied by dielectrophoresis, Biochimca et Biophysica Acta, 1993, 1149, pp. 119-126.
Foster, et al, High-intensity focused ultrsound in the treatment of prostatic disease, Eur Urol, 1993, 23(suppl1), pp. 29-33.
Andreason, Electroporation as a technique for the ransfer of macromolecules into mamalian cell lines, J. Tiss. Cult. Meth., 1993, 15, pp. 56-62.
Weaver, Electroporation: A general phenomenon for manipulating cells and tissues, Journal of Cellular Biochemistry, 1993, 51, pp. 426-435.
Barber, Electrical impedance tomography applied potential tomography, Advances in Biomedical Engineering, 1993, IOS Press, pp. 165-173.
Cook, et al, ACT3: a high-speed, high-precision electrical impedance tomograph, IEEE Transactions on Biomedical Engineering, 1994, vol. 41, No. 8, pp. 713-722.
Alberts, et al, Molecular biology of the Cell, Biocchemical education, 1994, 22(3), pp. 164.
Hughes, et al, An analysis of studies comparing electrical impedance tomography with x-ray videofluoroscopy in the assessment of swallowing, Physiol. Meas. 1994, 15, pp. A199-A209.
Griffiths, Tissue spectroscopy with electrical impedance tomography: Computer simulations, IEEE Transactions on Biomedical Engineering, Saep 1995, vol. 42, No. 9, pp. 948-954.
Gencer, et al, Electrical impedance tomography: Induced-currentimaging achieved with a multiple coil system, IEEE Transactions on Biomedical Engineering, Feb. 1996, vol. 43, No. 2, pp. 139-149.
Weaver, Chizmadzhev, Review Theory of electroporation: a review, Biolectrochemistry and Bioenergetics, 1996, 41, pp. 135-160.
Gimsa, et al, Dielectric spectroscopy of single human erythrocytes at physiological ionic strength: Dispersion of the cytoplasm, Biophysical Journal, Jul. 1996, vol. 71, pp. 495-506.
International Search Report for PCT/US2010/029243 WOSA dated Jul. 30, 2010.
International Search Report for PCT/US2010/022011 ISR dated Aug. 30, 2010.
International Search Report for PCT/US2010/022011 WOSA dated Aug. 30, 2010.
International Search Report for PCT/US2006/016045 IPRP dated Oct. 30, 2007.
International Search Report for PCT-US-10-053077 ISR dated Aug. 2, 2011.
International Search Report for PCT-US-10-053077 WOSA dated Aug. 2, 2011.
International Search Report for PCT/US2009/042100 IPRP IPRP dated Nov. 2, 2010.
International Search Report for EP 09739678 SESR dated May 3, 2012.
International Search Report for PCT/US2010/029243 IPRP dated Oct. 4, 2011.
International Search Report for PCT/US2009/048270 IPRP dated Jan. 5, 2011.
International Search Report for PCT/US2007/000084 IPRP dated Jul. 8, 2008.
International Search Report for PCT/US2009/042100 ISR dated Jul. 9, 2009.
International Search Report for PCT/US2009/042100 WOSA dated Jul. 9, 2009.
International Search Report for PCT/US2009/048270 ISR dated Feb. 11, 2010.
International Search Report for PCT/US2009/048270 WOSA dated Feb. 11, 2010.
International Search Report PCT/US2009042100 ESO dated May 11, 2012.
International Search Report PCT/US2009/038661 ISR dated Jun. 12, 2009.
International Search Report 12002108.4 ESO dated Jun. 12, 2013.
International Search Report PCT/US07/00084 WOSA dated Dec. 14, 2007.
International Search Report for PCT/US2011/056177 IPRP dated Apr. 16, 2013.
International Search Report for 06751655 SESR dated Oct. 9, 2016.
International Search Report for PCT/US2010/053077 ISR IPRP dated Apr. 17, 2012.
International Search Report for 11833421 SESR dated Mar. 18, 2014.
International Search Report for PCT/US2011/024909 ISR dated Oct. 18, 2011.
International Search Report for PCT/US2011/024909 WOSA dated Oct. 18, 2011.
International Search Report for 07716249 SESR dated Jan. 19, 2009.
International Search Report for PCT/US2009/062806 IPRP dated Jan. 4, 2012.
International Search Report for PCT/US2009/062806 ISR dated Jan. 19, 2010.
International Search Report for PCT/US2009/062806 WOSA dated Jan. 19, 2010.
International Search Report for 10824248.8 ESO dated Jan. 20, 2014.
International Search Report for PCT/US2009/047969 ISR dated Jan. 21, 2010.
International Search Report for PCT/US2009/047969 WOSA dated Jan. 21, 2010.
International Search Report for PCT/US2011/024909 IPRP dated Aug. 21, 2012.
International Search Report for PCT/US2011/025003 IPRP dated Aug. 21, 2012.
International Search Report for PCT/US2009/047969 IPRP dated Dec. 21, 2010.
International Search Report for PCT/US2010/036734 ISR dated Dec. 23, 2010.
International Search Report for PCT/US2010/036734 WOSA dated Dec. 23, 2010.
International Search Report for PCT/US2011/025003 ISR dated Oct. 24, 2011.
International Search Report for PCT/US2011/025003 WOSA dated Oct. 24, 2011.
International Search Report for PCT/US2011/062067 ISR dated Jul. 25, 2012.
International Search Report for PCT/US2011/062067 WOSA dated Jul. 25, 2012.
International Search Report for PCT/US06/16045 ISR dated Sep. 25, 2007.
International Search Report for PCT/US2010/022011 IPRP dated Jul. 26, 2011.
International Search Reprot for PCT/US2011056177 ESO dated Mar. 28, 2014.
International Search Report for PCT/US2011/062067 IPRP dated May 28, 2013.
International Search Report for PCT/US2009/038661 IPRP dated Sep. 28, 2010.
International Search Report for 06751655.9 ESO dated Oct. 29, 2009.
International Search Report for PCT/US2010/036734 IPRP dated Nov. 29, 2011.
International Search Report for 12002108 EPS dated May 30, 2012.
International Search Report for PCT/US2011/056177 ISR dated May 30, 2012.
International Search Report for PCT/US2011/056177 WOSA dated May 30, 2012.

(56) References Cited

OTHER PUBLICATIONS

International Search Report for PCT/US10/29243 ISR dated Jul. 30, 2010.
Wright, On a relationship betweene the arrhenius parameters from thermal damage studies, Technical Brief, Journal of Biomechanical Engineering, Transactions of the ASME, Apr. 2003, vol. 125, pp. 300-304.
Heczynska, et al, Hypoxia promotes a dedifferentiated phenotype in ductal breast carcinoma in situ, Cancer Research, Apr. 1, 2003, 63, pp. 1441-1444.
Ivorra, Bioimpedance monitoring for physicians: an overview, Biomedical Applications Group, Centre Nacional de Microelectronica, Jul. 2003, pp. 1-35.
Weaver, Electroporation of biological membranes from multicellular to nano scales, IEEE Transactions on Dielectrics and Electrical Insulation, Oct. 2003, vol. 10, No. 5, pp. 754-768.
Dev, et al, Electric field of a six-needle array electrode used in drug and DNA delivery in vivo: Analytical versus numerical solution, IEEE Transactions on Biomedical Engineering, Nov. 2003, vol. 50, No. 11, pp. 1296-1300.
Rajagopal, Rockson, Coronary restenosis: A review of mechanisms and management, The American Journal of Medicine, Nov. 2003, vol. 115, pp. 547-553.
Sersa, et al, Tumor blood flow modifying effects of electrochemotherapy: a potential vascular targeted mechanism, Radiol Oncol, 2003, 37, 1, pp. 43-48.
Davalos, et al, Theoretical analysis of the thermal effects during in vivo tissue electroporation, Bioelectrochemistry, 2003, 61, pp. 99-107.
Gothelf, et al, Electrochemotherapy: results of cancer treatment using enhanced delivery of bleomycin by electroporation, Cancer Treatment Reviews, 2003, 39, pp. 371-387.
Bancroft, et al, Design of a flow perfusion bioreactor system for bone tissue-engineering applications, Tissue Engineering, 2003, vol. 9, No. 3, pp. 549-554.
Malpica, et al, Grading ovarian serous carcinoma using a two-tier system, Am J Surg Pathol, Apr. 2004, vol. 28, No. 4, pp. 496-504.
Davalos, et al, Electrical impedance tomography for imaging tissue electroporation, IEEE Transactions on Biomedical Engineering, May 2004, vol. 51, No. 5, pp. 761-767.
Albright, et al, Performance and complicatioins associated with the Synchromed 10-ml infusion pump for intrathecal baclofen administration in children, J Neurosurg (Pediatrics 2), Aug. 2004, vol. 101, pp. 64-68.
Diederich, et al, Catheter-based ultrasound applicators for selective thermal ablation: progress towards MRI-guided applications in prostate, Int. J. Hyperthermia, Nov. 2004, vol. 20, No. 7, pp. 739-756.
Radeva, et al, Induction of apoptosis and necrosis in cancer cells by electric fields, electromagnetic fields, and photodynamically active quinoids, Electromagnetic Biology and Medicine, 2003, 23, pp. 185-200.
Davalos, et al, Tissue ablation with irreversible electroporation, Annals of Biomedical Engineering, Feb. 2005, vol. 33, No. 2, pp. 223-231.
Sel, et al, Sequential finite element model of tissue electropermeabilization, IEEE Transactions on Biomedical Engineering, May 2005, vol. 52, No. 5, pp. 816-827.
Dean, Nonviral gene transfer to skeletal, smooth, and cardiac muscle in living animals, Am J Physiol cell Physiol, Aug. 2005, 289, pp. C233-C245.
Pavselj, et al, The course of tissue permeabilization studied on a mathematical model of a subcutaenous tumor in small animals, IEEE Transactions on Biomedical Engineering, Aug. 2005, vol. 52, No. 8, pp. 1373-1381.
Paszek, et al, Tensional homeostasis and the malignant phenotype, Cancer Cell, Sep. 2005, vol. 8, pp. 241-254.
Saur, et al, CXCR4 expression increases liver and lung metastasis in a mouse model of pancreatic cancer, Basic-Liver, pancreas, and biliary tract, Gastroenterology, Oct. 2004, 129, pp. 1237-1250.
Knight, et al, Direct imaging of transvenous radiofrequency cardiac ablation using a steerable fiberoptic infrared endoscope, Heart Rhythm Society, Oct. 2005, vol. 2, No. 10, pp. 1116-1121.
Miller, et al, Cancer cells ablation with irreversible electroporation, Technology in Cancer Research and Treatment, Dec. 2005, vol. 4, No. 6, pp. 699-705.
Mir, et al, Electric pulse-mediated gene delviery to various animal tissues, Advances in Genetics, 2005, vol. 54, pp. 84-114.
Nikolski, Efimov, Electroporation of the heart, Europace, 2005, 7, pp. S146-S154.
Machado-Aranda, et al, Gene transfer of the NA+, K+K -ATPase B1 subunit using electroporation increases lung liquid clearance, American Journal of Respiratory and Critical Care Medicine, 2004, vol. 171, pp. 204-211.
Kotnik, Miklavcic, Theoretical evaluation of voltage inducement on internal membranes of biological cells exposed to electric fields, Biophysical Journal, Jan. 2006, vol. 90, pp. 480-491.
Labeed, et al, Differences in the biophysical properties of membrane and cytoplasm of apoptotic cells revealed using dielectrophoresis, Biochimica et Biophysica Acta, Feb. 23, 2006, 1760, pp. 922-929.
Pucihar, et al, Numerical determination of transmembrane voltage indcued on irregularly shaped cells, Annals of Biomedical Engineering, Mar. 18, 2006, vol. 34, No. 4, pp. 642-652.
Gilbert, et al, Decellularization of tissues and organs, Biomaterials, Mar. 7, 2006, 27, pp. 3675-3683.
Edd, et al, In vivo results of a new focal tissue ablation technique: Irreversible electroporation, IEEE Transactions on Biomedical Engineering, Jun. 2006, vol. 53, No. 5, pp. 1409-1415.
Ivorra, Rubinsky, Impedance analyzer for in vivo electroporation studies, Proceedings of the 28th IEEE EMBS Annual International Conference, IEEE, Aug. 30, 2006, pp. 5056-5059.
Carpenter, et al, CellProfiler: image analysis software for identifying and quantifying cell phenotypes, Genome Biology, Oct. 31, 2006, vol. 7, Iss. 10, R100, pp. 1-11.
Kanduser, et al, Cell membrane fluidity related to electroporation and resealing, Eur Biophys J, Oct. 8, 2006, 35, pp. 196-204.
Bolland, et al, Development and characterisation of a full-thickness acellular porcine bladder matrix for tissue engineering, Biomaterials, Nov. 7, 2006, 28, pp. 1061-1070.
Cukjati, et al, Real time electroporation control for accurate and safe in vivo non-viral gene therapy, Bioelectrochemistry, Nov. 10, 2006, 70, pp. 501-507.
Tijink, et al, How we do it: Chemo-electroporation in the head and neck for otherwise untreatable patients, Correspondence, Clinical Otolaryngology, 2006, 31, pp. 447-451.
Marty, et al, Electrochemotherapy—An easy, highly effective and safe treatment of cutaneous and subcutaneous metastases: Results of ESOPE (European Standard Operating Procedures of Electrochemotherapy) study, EJC Supplements, 2006, 4, pp. 3-13.
Soden, et al, Successful application of targeted electrochemotherapy using novel flexible electrodes and low dose bleomycin to solid tumors, Cancer Letters, 2006, 232 pp. 300-310.
Demirbas, Thermal energy storage and phase change materials: An overview, Energy Sources, Part B, 2006, 1, pp. 85-95.
Rubinsky, et al, Irreversible electroporation: A new ablation modality—Clinical implications, Technology in Cancer Research and Treatment, Feb. 2007, vol. 6, No. 1, pp. 1-12.
Zhou, et al, Electroporation-mediated transfer of plasmids to the lung results in reduced TLR9 signaling and inflammation, Gene Therapy, Mar. 8, 2007, 14, pp. 775-780.
Lavee, et al, A novel nonthermal energy source for surgical epicardial atrial ablation: Irreversible electroporation, The Heart Forum, Mar. 2007, 10, 2, pp. 96-101.
Hall, et al, Nanosecond pulsed electric fields induce apoptosis in p53-wildtype and p53-null HCT116 colon carcinoma cells, Apoptosis, May 23, 2007, 12, pp. 1721-1731.
Sel, et al, Feasibility of employing model-based optimization of pulse amplitude and electrode distance for effective tumor electropereabilization, IEEE Transactions on Biomedical Engineering, May 2007, vol. 54, No. 5, pp. 773-781.
Kirson, et al, Alternating electric fields arrest cell proliferation in animal tumor models and human brain tumor, PNAS, Jun. 12, 2007, vol. 104, No. 24, pp. 10152-10157.

(56) References Cited

OTHER PUBLICATIONS

Talele, Gaynor, Non-linear time domain model of electropermeabilizationi: Response of a single cell to an arbitary applied electric field, Journal of Electrostatics, Jul. 16, 2007, 65, pp. 775-784.
Esser, et al, Towards solid tumor treatment by irreversible electroporation: Intrinsic redistribution of fields and currents in tissue, Technology in Cancer Research and Treatment, Aug. 2007, vol. 6, No. 4, pp. 261-273.
Maor, et al, The effect of irreversible electroporation on blood vessels, Technology in Cancer Research and Treatment, Aug. 2007, vol. 6, No. 4, pp. 307-312.
Edd, Davalos, Mathematical modeling of irreversible electroporation for treatment planning, Technology in Cancer Research and Treatment, Aug. 2007, vol. 6, No. 4, pp. 275-286.
Rubinsky, Irreversible electroporation in medicine, Technology in Cancer Research and Treatment, Aug. 2007, vol. 6, No. 4, pp. 255-259.
Onik, et al, Irreversible electroporation: Implications for prostate ablation, Technology in Cancer Research and Treatment, Aug. 2007, vol. 6, No. 4, pp. 295-300.
Lee, et al, Imaging guided percutaneous irreversible electroporation: Ultrasound and immunohistological correlation, Technology in Cancer Research and Treatment, Aug. 2007, vol. 6, No. 4, pp. 287-293.
Bertacchini, et al, Design of an irreversible electroporation system for clinical use, Technology in Cancer Research and Treatment, Aug. 2007, vol. 6, No. 4, pp. 313-320.
Al-Sakere, et al, A study of the immunological response to tumor ablation with irreversible electroporation, Technology in Cancer Research and Treatment, Aug. 2007, vol. 6, No. 4, pp. 301-305.
Fischbach, et al, Engineering tumors with 3D scaffolds, Nature Methods, Sep. 2, 2007, vol. 4, No. 10, pp. 855-860.
Ivorra, Rubinsky, In vivo electrical impedance measurements during and after electroporation of rat liver, Bioelectrochemistry, Oct. 21, 2007, 70, pp. 287-295.
Yao, et al, Study of transmembrane potentials of inner and outer membranes induced by pulsed-electric-field model and simulation, IEEE Transactions on Plasma Science, Oct. 2007, vol. 35, No. 5, pp. 1541-1549.
Corovic, et al, Analytical and numerical quantification and comparison of the local electric field in the tissue for different electrode configurations, BioMedical Engineering Online, Oct. 15, 2007, 6, 37, pp. 1-14.
Schoenbach, et al, Bioelectric effects of intense nanosecond pulses, IEEE Transactions on Dielectric and Electrical Insulation, 2007, vol. 14, Iss. 5, pp. 1088-1109.
Al-Sakere, et al, Tumor ablation with irreversible electroporation, PLOS One, Nov. 7, 2007, Iss. 11, e1135, pp. 1-8.
Hall, et al, Nanosecond pulsed electric fields have differential effects on cells in the S-phase, DNA and Cell Biology, 2007, vol. 26, No. 3, pp. 160-171.
He, et al, Nonlinear current response of micro electroporation and resealing dynamics for human cancer cells, Bioelectrochemistry, Jan. 29, 2008, 72, pp. 161-168.
Ott, et al, Perfusion-decellarized matrix: using nature's platform to engineer a bioartificial heart, Nature Medicine, Jan. 13, 2008, vol. 14, No. 2, pp. 213-221.
Ron, et al, Cell-based screening for membranal and cytoplasmic markers using dielectric spectroscopy, Biophysical Chemistry, Mar. 29, 2008, 135, pp. 59-68.
Garcia, et al, Irreversible electroporation (IRE) to treat brain tumors, Proceedings of the ASME 2008 Summer Bioengineering Conference (SBC2008), Jun. 25, 2008, pp. 6-7.
Davalos, Rubinsky, Temperature considerations during irreversible electroporation, International Journal of Heat and Mass Transfer, Jun. 14, 2008, 51, pp. 5617-5622.
Dahl, et al, Nuclear shape, mechanics and mechanotransduction, Circulation Research, Jun. 6, 2008, 102, pp. 1307-1318.
Seidler, et al, A Cre-IoxP-based mouse model for conditional somatic gene expression and knockdown in vivo by using avian retroviral vectors, PNAS, Jul. 22, 2008, vol. 105, No. 29, pp. 10137-10142.
Maor, et al, Intravascular irreversible electroporation: Theoretical and experimental feasibility study, 30th Annual International IEEE EMBS Conference, IEEE, Aug. 20, 2008, pp. 2051-2054.
Maor, et al, Irreversible electroporation attenuates neointimal formation after angioplasty, IEEE Transactions on Biomedical Engineering, Sep. 2008, vol. 55, No. 9, pp. 2268-2274.
Jensen, et al, Tumor volume in subcutaneous mouse xenografts measured by microCT is more accurate and reproducible than determined by 18F-FDG-microPET or external caliper, BMC Medical Imaging, Oct. 16, 2008, 8, 16,m pp. 1-9.
Rubinsky, et al, Optimal parameters for the destruction of prostate cancer using irreversible electroporation, The Journal of Urology, Dec. 2008, vol. 180, pp. 2668-2674.
Daud, et al, Phase I trial of Interleukin-12 plasmid electroporation in patients with metastatic melanoma, Journal of Clinical Oncology, Dec. 20, 2008, vol. 26, No. 36, pp. 5896-5903.
Flanagan, et al, Unique dielectric properties distinguish stem cells and their differentiated progency, Stem Cells, 2008, 26, pp. 656-665.
Mali, et al, The effect of electroporation pulses on functioning of the heart, Med Biol Eng Comput, 2008.
Kuthi, Gundersen, Nanosecond uplse generator with scalable pulse amplitude, IEEE, 2008, pp. 65-68.
Craiu, Scadden, Chapter 22 flow electroporation with pulsed electric fields for purging tumor cells, Electroporation Protocols: Preclinical and Clinical Gene Medicine, Methods in Molecular Biology, vol. 423, pp. 301-310.
Mir, Chapter 1 application of electroporation gene therapy: Past, current and future, Electroporation Protocols: Preclinical and Clinical Gene Medicine, Methods in Molecular Biology, vol. 423, pp. 3-17.
Lin, Lee, An optically induced cell lysis device using dielectrophoresis, Applied Physics Letters, Jan. 20, 2009, 94, 033901, pp. 1-3.
Kroeger, et al, Curvature-driven pore growth in charged membranes during charge-pulse and voltage-clamp experiments, Biophysical Journal, Feb. 2009, 96, 3, pp. 907-916.
Maor, et al, Non thermal irreversible electroporation: Novel technology for vascular smooth muscle cells abation, PLOS One, Mar. 9, 2009, vol. 4757-, Iss. 3, e4757, pp. 1-9.
Shafiee, et al, A preliminary study to delineate irreversible electroporation from thermal damage using the Arrhenius equation, Journal of Biomedical Engineering, Jul. 2009, vol. 131, 074509, pp. 1-5.
Granot, et al, in vivo imaging of irreversible electroporation by means of electrical impedance tomography, Phys. Med. Biol., Jul. 30, 2009, 54, pp. 4927-4943.
Daniels, Rubinsky, Electrical field and temperature model of nonthermal irreversible electroporation in heterogeneous tissues, Journal of Biomedical Engineering, Jul. 2009, vol. 131, 071006, pp. 1-12.
Esser, et al, Towards solid tumor treatment by nanosecond pulsed electric fields, Technology in Cancer Research and Treatment, Aug. 2009, vol. 8, No. 4, pp. 289-306.
Ivorra, et al, In vivo electrical conductivity measurements during and after tumor electroporation: conductivity changes reflect the treatment,Phys. Med. Biol., Sep. 17, 2009, 54, pp. 5949-5963.
Garcia, et al, Pilot study of irreversible electroporation for intracranial surgery, 31st Annual International Conference of the IEEE EMBS, IEEE, Sep. 2, 2009, pp. 6513-6516.
Hong, et al, Cardiac ablation via electroporation, 31st Annual International Conference of the IEEE EMBS, IEEE, Sep. 2, 2009, pp. 3381-3384.
Neal, Davalos, The feasibility of irreversible electroporation for the treatment of breast cancer and other heterogeneous systems, Annals of Biomedical Engineering, Dec. 2009, vol. 37, No. 12, pp. 2615-2625.
Sharma, et al, Review on thermal energy storage with phase change materials and applications, Renewable and Sustainable Energy Reviews, 2009, 13, pp. 318-345.

(56) References Cited

OTHER PUBLICATIONS

Ibey, et al, Selective cytotoxicity of intense nanosecond-duration electric pulses in mammalian cells, Biochim Biophys Acta, Nov. 2010, 1800, 11, pp. 1210-1219.
Tsivian, Polascik, Recent advances in focal therapy of prostate and kidney cancer, Medicine Reports, Jan. 18, 2010, 2, 1, pp. 1-3.
adEYANJU, et al, The improvement of irreversible electroporation therapy using saline-irrigated electrodes: A theoretical study, Technology in Cancer Research and Treatment, Aug. 2011, vol. 10, No. 4, pp. 347-360.
Maor, Rubinsky, Endovascular nonthermal irreversible electroporation: A finite element analysis, Journal of Biomedical Engineering, Feb. 7, 2010, vol. 132, 031008, pp. 1-7.
Choi, et al, Preclinical analysis of irreversible electroporation on rat liver tissues using a microfabricated electroporator, Tissue Engineering Part C, 2010, vol. 16, No. 6, pp. 1245-1253.
Verbridge, et al, Oxygen-controlled three-dimensional cultures to analyze tumor angiogenesis, Tissue Engineering, Part A, Apr. 9, 2010, vol. 16, No. 7, pp. 2133-2141.
Lee, et al, Advanced hepatic ablation technique for creating complete cell death: Irreversible electroporation, 2010, Radiology, vol. 255, No. 2, pp. 426-433.
Ball, et al, Irreversible electroporation: A new challenge in "out of the operating theater" anesthesia, Anesth Analg, May 2010, 110, pp. 1305-1309.
Laufer, et al, Electrical impedance characterization of normal and cancerous human hepatic tissue, Physiol Meas, 2010, 31, pp. 995-1009.
Sabuncu, et al, Dielectrophoretic separation of mouse melanoma clones, Biomicrofluidics, Jun. 16, 2010, 4, 021101, pp. 1-7.
Garcia, et al, Intracranial nonthermal irreversible electroporation: In vivo analysis, J Membrane Biol, Jul. 29, 2010, 236, pp. 127-136.
Neal, et al, Treatment of breast cancer through the application of irreversible electroporation using a novel minimally invasive single needle electrode, Breat Cancer Res Treat, Aug. 27, 2010, 123, 1, pp. 295-301.
Zhang, et al, MR imaging to assess immediate response to irreversible electroporation for targeted ablation of liver tissues: Preclinical feasibility studies in a rodent model, Radiology, Aug. 2010, vol. 256, No. 2, pp. 424-32.
Neal, et al, A study using irreversible electroporation to treat large, irregular tumors in a canine patient, 32nd Annual International Conference of the IEEE EMBS, IEEE, Aug. 2010, pp. 2747-2750.
Garcia, et al, Non-thermal irreversible electroporation for deep intracranial disorders, 32nd Annual International Conferenece of the IEEE EMBS, IEEE, Aug. 2010, pp. 2747463-.
Phillips, et al, Nonthermal irreversible electroporation for tissue decellularization, Journal of Biomedical Engineering, Aug. 16, 2010, vol. 132, 091003, pp. 1-8.
Pech, et al, Irreversible electroporation of renal cell carcinoma: A first-in-man phase I clinical study, Cardiovasc Intervent Radiol, Aug. 15, 2010.
Lee, et al, Irreversible electroporation: A novel image-guided cancer therapy, Gut and Liver, Sep. 2010, vol. 4, Supp. 1, pp. S99-104.
Hong, et al, Cardiac ablation via electroporation, 31st Annual International Conference of the IEEE EMBS, IEEE, Sep. 2, 2010, pp. 3381-3384.
Dupuy, et al, Irreversible electroporation in a swine lung model, Cardiovasc Intervent Radiol, Dec. 30, 2010, 34, pp. 391-395.
Arena, et al, Theoretical considerations of tissue electropration with high frequency biopolar pulses, IEEEE, pp. 1-7.
Deodhar, et al, Renal tissue ablation with irreversible electroporation: Preliminary results in a porcine model, Technology and Engineering, Urology, 2010, 1-7.
Mccarley, Soulen, Percutaneous ablation of hepatic tumors, Seminars in Interventional Radiology, 2010, vol. 27, No. 3, pp. 255-260.
Neu, Neu, Mechanism of irreversible electroporation in cells: Insight from the models, Irreversible Electroporation: BIOMED, pp. 85-122.
Charpentier, et al, Irreversible electroporation of the pancreas in swine: A pilot study, HPB, 2010, 12, pp. 348-351.
Tracy, et al, Irreversible electroporation (IRE): A novel method for renal tissue ablation, BJU International, 107, pp. 1982-1987.
Onik, Rubinsky, Irreversible electroporation: First patient experience focal therapy of prostate cancer, Irreversible Electroporation, BIOMED, pp. 235-247.
Mcwilliams, et al, Image-guided tumor ablation: Emerging technologies and future directions, Seminars in Interventional Radiology, 2010, vol. 27, No. 3, pp. 302-313.
Kurup, Callstrom, Image-guided percutaneous ablation of bone and soft tissue tumors, Seminars in Interventional Radiology, 2010, vol. 27, No. 3, pp. 276-284.
Thomson, Human experience with irreversible electroporation, Irreversible Electroporation, BIOMED, 2010, pp. 249-354.
Saldanha, et al, Current tumor ablation technologies: Basic science and device review, Seminars in Interventional Radiology, 2010, vol. 27, No. 3, pp. 247-254.
Dupuy, Shulman, Current status of thermal ablation treatments for lung malignancies, Seminars in Interventional Radiology, 2010, vol. 27, No. 3, pp. 268-275.
Carmi, Georgiades, Combination percutaneous and intraarterial therapy for the treatment of hepatocellular carcinoma: A review, Seminars in Interventional Radiology, 2010, vol. 27, No. 3, pp. 296-301.
Jarm, et al, Antivascular effects of electrochemotherapy: implicatoins in treatment of bleeding metastases, Expert Rev. Anticancer Ther., 2010, 10, 5, pp. 729-746.
Maybody, An overview of image-guided percutaneous ablation of renal tumors, Seminars in Interventional Radiology, 2010, vol. 27, No. 3, pp. 261-267.
Goldberg, Rubinsky, A statistical model for multidimensional irreversible electroporation cell death in tissue, Biomedical Engineering Online, 2010, 9:13, pp. 1-13.
Sano, et al, Towards the creation of decellularized organ constructs using irreversible electroporation and active mechanical perfusion, Biomedical Engineering Online, 2010, 9, 83, pp. 1-16.
Mahmood, Gehl, Optimizing clinical performance and geometrical robustness of a new electrode device for intracranial tumor electroporation, Bioelectrochemistry, Jan. 6, 2011, 81, pp. 10-16.
Garcia, et al, Non-thermal irreversible electroporation (N-TIRE) and adjuvant fractionated radiotherapeutic multimodal therapy for intracranial malignant glioma in a canine patient, Feb. 2011, vol. 10, No. 1, pp. 73-83.
Guo, et al, Irreversible electroporation in the liver: Contrast-enhanced inversion-recovery MR imaging approaches to differentiate reversibly electroporated penumbra from irreversibly electroporated ablation zones, Radiology, Feb. 2011, vol. 258, No. 2, pp. 461-468.
Bower, et al, Irreversible electroporation of the pancreas: Definitive local therapy without systemic effects, Journal of Surgical Oncology, Feb. 28, 2011, 104, pp. 22-28.
Ellis, et al, Nonthermal irreversible electroporation for intracranial surgical applications, J Neurosurg, Mar. 2011, 114, pp. 681-688.
Nesin, et al, Manipulation of cell volume and membrane pore comparision following single cell permeabilization with 60- and 600-ns. electric pulses, Biochim Biophys Acta, Mar. 2011, 1808(3), pp. 792-801.
Mccall, Nanoknife, liposomal doxorubicin show efficacy against liver cancer, European Congress of Radiology, Mar. 7, 2011, pp. 1-2.
Mahmood, et al, Diffusion-weighted MRI for verification of electroporation-based treatments, J Membrane Biol, Mar. 6, 2011, 240, pp. 131-138.
Deodhar, et al, Irreversible electroporation near the heart: Ventricular arrhythmias can be prevented with ECG synchronization, AJR, Mar. 2011, 196, pp. W330-W335.
Garcia, et al, A parametric study delineating irreversible electroporation from thermal damage based on a minimally invasive intracranial procedure, Biomedical Engineering Online, 2011, 10: 34, pp. 1-21.
Li, et al, The effects of irreversible electroporation (IRE) on nerves, PLOS One, Apr. 14, 2011, vol. 6, Iss. 4, e18831, pp. 1-7.

(56) References Cited

OTHER PUBLICATIONS

Neal, et al, Successful treatment of a large soft tissue sarcoma with irreversible electroporaiton, Journal of Clinical Oncology, May 1, 2011, vol. 29, No. 13, pp. e372-e377.

Thomson, et al, Investigation of the safety of irreversible electroporation in humans, J Vasc Intery Radiol, May 2011, 22, pp. 611-621.

Rossmeisl, Jr., et al, Successful treatment of a large soft tissue sarcoma with irreversible electroporation, Journal of Clinical Oncology, May 1, 2011, vol. 29, No. 13, pp. e372-e377.

Daniels, Rubinsky, Temperature modulation of electric fields in biological matter, PLOS One, vol. 6, Iss. 6, e20877, pp. 1-9.

Lion, et al, Poly(I:C) enhances the susceptibility of leukemic cells to NK cell cytotoxicity and phagocytosis by DC, PLOS One, vol. 6, Iss. 6, e20952, pp. 1-10.

Agerholm-Larsen, et al, Preclinical validation of electrochemotherapy as an effective treatment for brain tumors, Cancer Res, Jun. 1, 2011, 71, 11, pp. 3753-3762.

Mulhall, et al, Cancer, pre-cancer and normal oral cells distinguished by dielectrophoresis, Anal Bioanal chem, Aug. 30, 2011, 401, pp. 2455-2463.

Troszak, Rubinsky, Self-powered electroporation using a singularity-induced nano-electroporation configuration, Biochemical and Biophysical Research Communications, Sep. 28, 2011, 414, pp. 419-424.

Arena, et al, High-frequency irreversible electroporation (H-FIRE) for non-thermal ablation without muscle contraction, BioMedical Engineering Online, Nov. 21, 2011, 10: 102, pp. 1-20.

Hjouj, et al, Electroporationo-induced BBB disruption and tissue damage depicted by MRI, Neuro-Oncology, Abstracts from the 16th Annual Scientific Meeting, Nov. 17, 2011, vol. 13, Supp 3, ET-32, p. iii114.

Mir, Orlowski, Introduction: Electropermeabilization as a new drug delivery approach, Methods in Molecular Medicine, 2000, vol. 37, pp. 99-117.

O'Brien, et al, Investigation of the Alamar Blue (resarzurin) fluorescent dye for the assessment of mammalian cell cytotoxicity, Eur J Biochem, 2000, 267, pp. 5421-5426.

\* cited by examiner

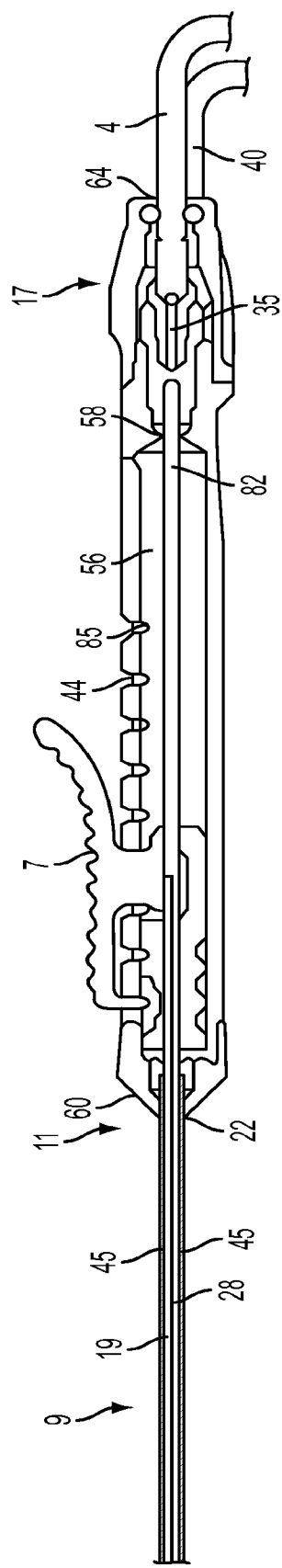
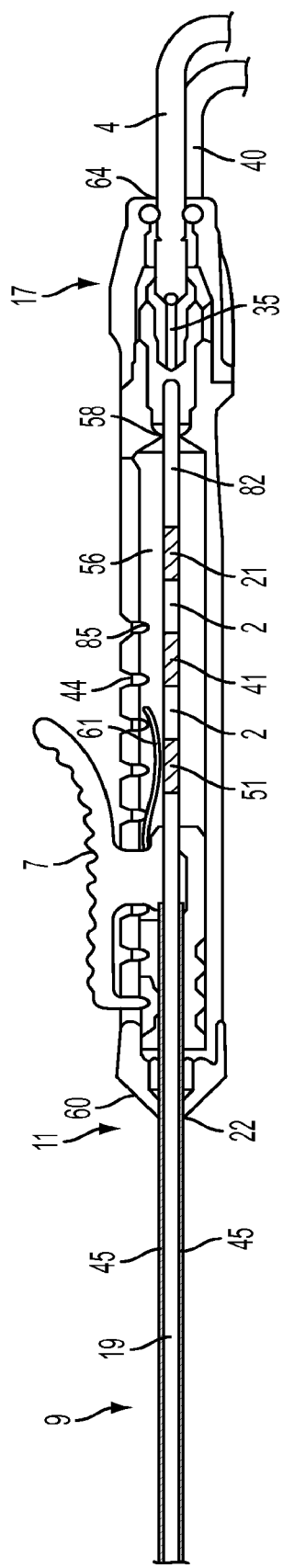
FIG. 5A
FIG. 5B

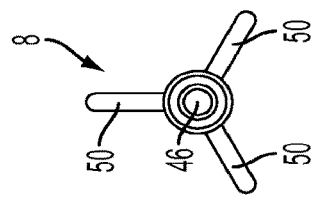
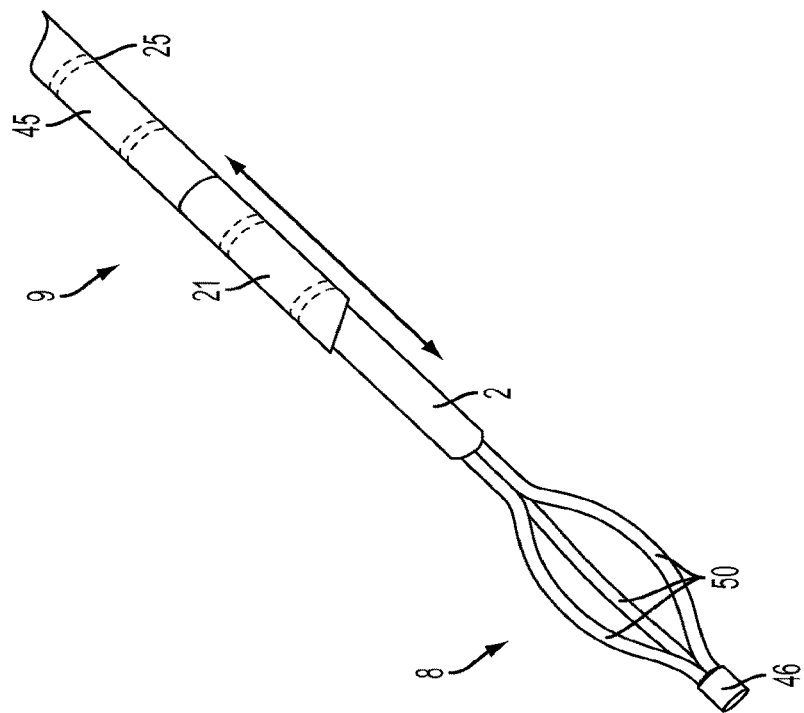
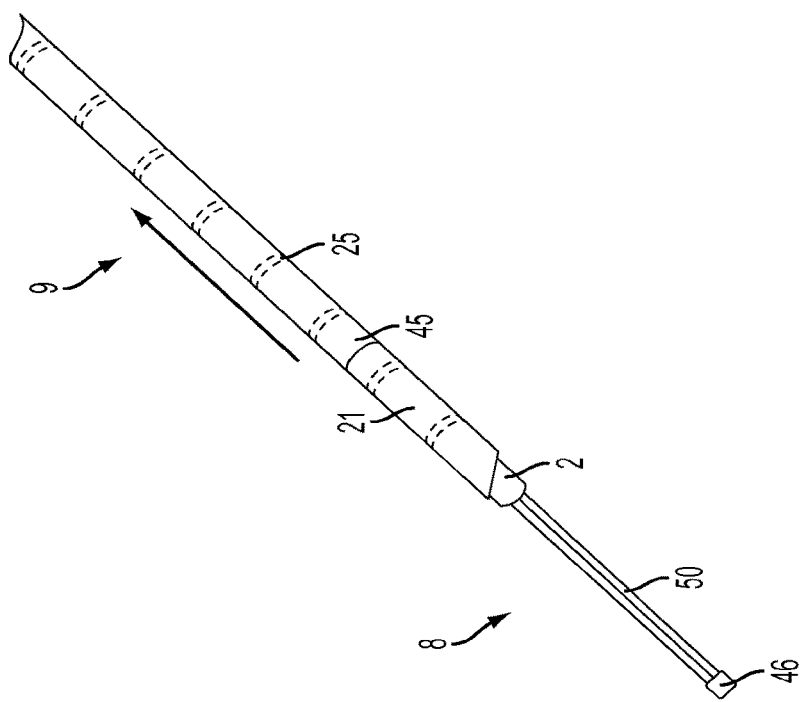

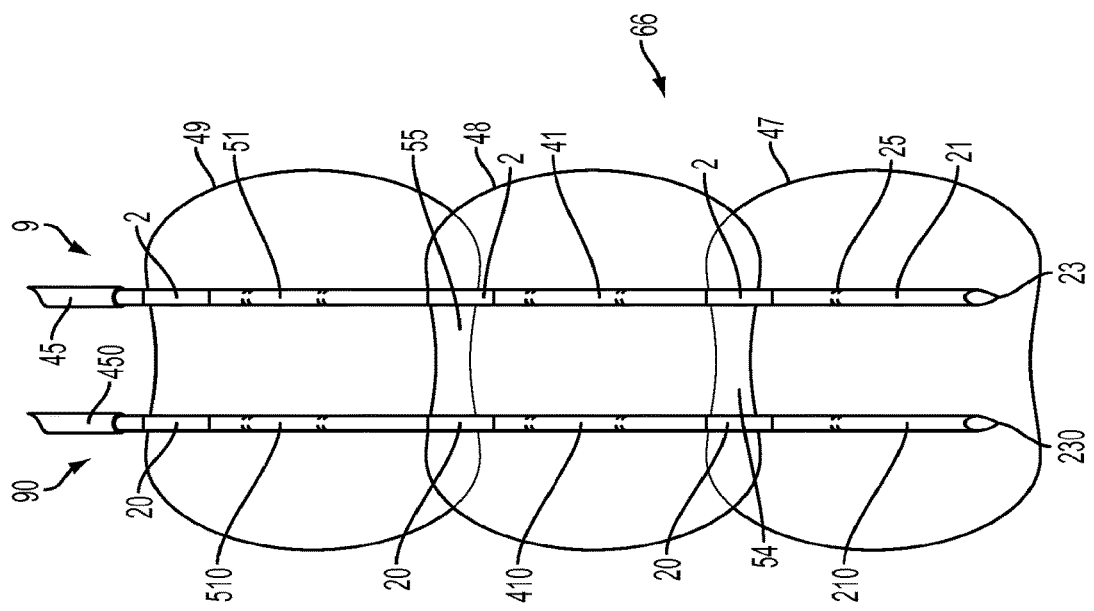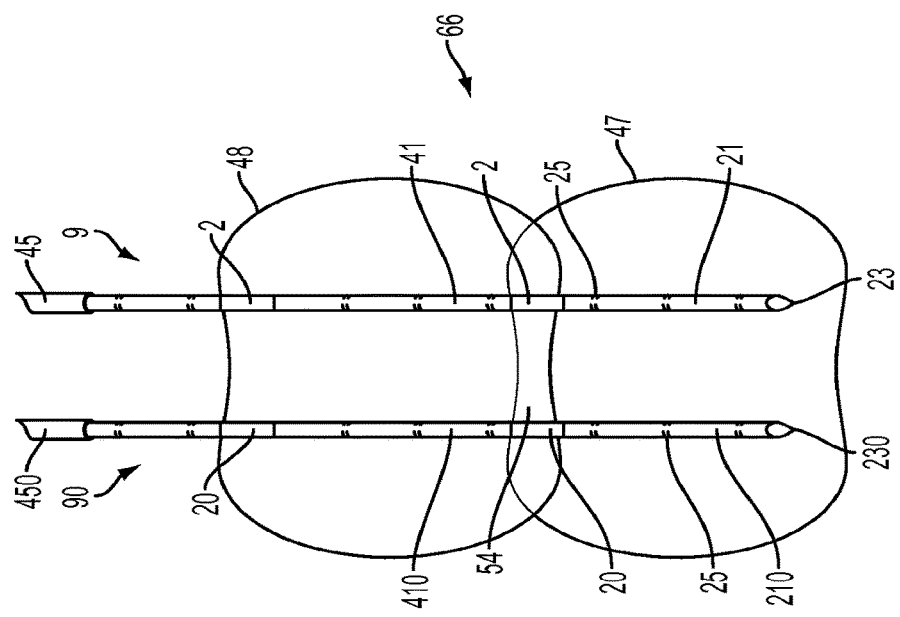

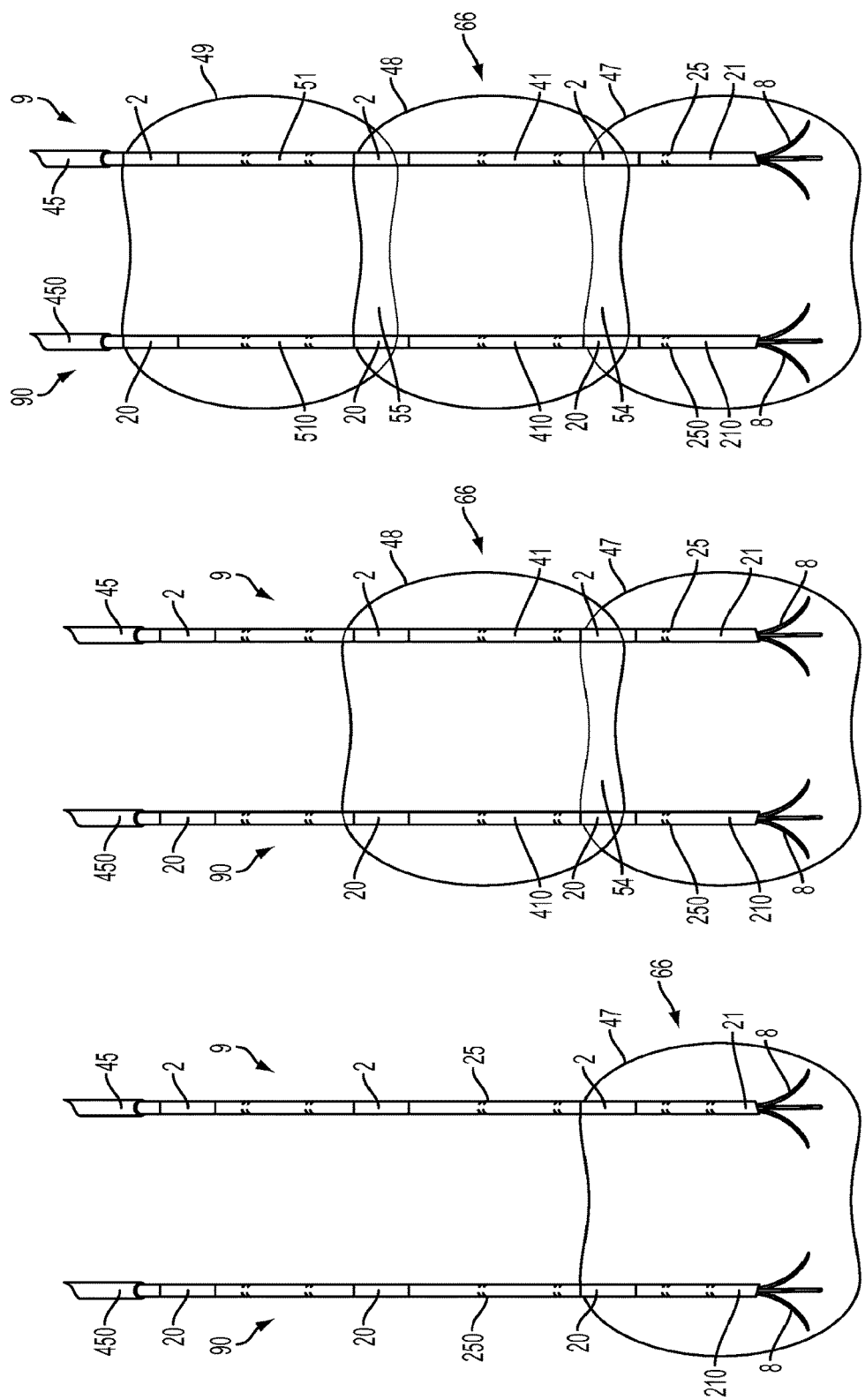

MULTIPLE TREATMENT ZONE ABLATION PROBE

CROSS-REFERENCE TO RELATED APPLICATIONS

This application is a continuation of U.S. patent application Ser. No. 13/630,135, filed Sep. 28, 2012, which is incorporated by reference herein in its entirety.

TECHNICAL FIELD

The present invention relates to an energy delivery probe and method of treatment using the energy delivery probe.

BACKGROUND OF THE INVENTION

Irreversible electroporation (IRE) is a non-thermal, minimally invasive surgical technique to ablate undesirable tissue, for example, tumor tissue. The technique is easy to apply, can be monitored and controlled, is not affected by local blood flow, and does not require the use of adjuvant drugs. The minimally invasive procedure involves placing needle-like electrodes into or around a targeted tissue area to deliver a series of short and intense electric pulses that induce structural changes in the cell membranes that promote cell death.

Another technique for ablating a desired target tissue is radiofrequency ablation (RFA). This procedure involves using an imaging guidance system such as ultrasound (US), computed tomography (CT), or magnetic resonance (MR). During this procedure, a physician places a probe directly into a target tissue area, such as a tumor. Using an energy source, a physician or other practitioner can then deliver a carefully-controlled amount of energy to flow through the electrodes into the tissue which causes the tissue to heat up. The heating is sustained for a predetermined length of time, usually just a few minutes, which kills and destroys the target tissue. RFA procedures can be percutaneously or laparoscopically performed.

Among the problems associated with current IRE procedures is that with current single IRE probe electrode designs, it is common practice for physicians to perform multiple overlapping or stacked ablations. In between each ablation, the physician has to reposition the probes. During this repositioning or pull-back process, however, it is sometimes difficult for physicians to keep all of the probes parallel for ablations that are performed after the first ablation. In addition, it is difficult to know exactly where the first ablation ends and how much overlap there is between successive ablations, which can increase the chances of missing portions of a target tumor tissue between the ablations or may result in unusual or unpredictable ablation shapes.

Another problem that sometimes occurs with current single IRE or RF ablation probes is probe migration. This occurs when an ablation probe moves slightly from the original position where the probe was inserted, either during the placement of additional probes or during an actual ablation procedure. When this occurs, an undertreated area of target tissue can potentially be left behind, or unintended target tissue can be ablated, or alternatively, a vital organ or structure can be damaged by the tip of a needle.

There exists a need in the art for an improved ablation probe and method of using such a probe for improved IRE and RF ablations that will allow a practitioner to more easily predict and control the location and size of IRE and RF ablations and provide the ability to easily maintain the electrodes in a stationary position within tissue before, during, and after an ablation. An electrode probe and method has not yet been proposed that would solve the problems described above, thereby avoiding many of the negative side effects of the current devices described above.

It is a purpose of the invention described herein to provide a dual probe device in which each probe has at least two electrode regions that can be switched between an active energy delivery state and a non-active non-energy delivery state, depending in the desired ablation zone(s), during either IRE or RF ablations.

It is also a purpose of this invention to provide various anchoring means at the distal tip of the ablation probe described herein in order to anchor at least portion of an active portion of the probe(s) relative to a patient's tissue throughout an ablation procedure.

It is also a purpose of this invention to provide an ablation probe that incorporates a means of adjusting the active portion of the electrode axially along the trocar, or the ablation probe may incorporate a plurality of fixed active portions along the trocar in order to allow the user to create multiple ablations along a specific controlled path through a lesion without repositioning the ablation device.

Various other objectives and advantages of the present invention will become apparent to those skilled in the art as more detailed description is set forth below. Without limiting the scope of the invention, a brief summary of some of the claimed embodiments of the invention is set forth below. Additional details of the summarized embodiments of the invention and/or additional embodiments of the invention can be found in the Detailed Description of the Invention.

SUMMARY

A method of treating a patient is presented herein. The method involves identifying a target tissue, providing at least one energy delivery probe having a longitudinal axis, at least a first trocar and a second trocar. In one embodiment, each of the trocars has a proximal portion and a distal portion can optionally have at least one lumen extending along the longitudinal axis. The distal portions of each of the trocars are capable of piercing tissue. Each of the trocars has at least two electrodes that are electrically insulated from each other. Each electrode is independently selectively activatable. The ablation probe also has an insulative sleeve that is positioned in a coaxially surrounding relationship to at least a portion of each of the first trocar and the second trocar and a switching means for independently activating at least one electrode. The method further involves inserting the probe into or near the target tissue, activating at least a first electrode on the first trocar and a first electrode on the second trocar, and delivering energy to the target tissue to ablate the tissue, thereby forming at least one ablation zone. The ablation method can be repeated between various sets of electrodes between the trocars to produce multiple overlapping ablation zones.

Also described herein is a variation of the ablation method described above. The method involves identifying a target tissue, providing at least one energy delivery probe, as described above, which energy delivery probe further includes at least one anchoring means that is capable of being deployed from the distal end of the probe, inserting the probe into or near the target tissue, deploying the at least one anchoring means, activating at least a first electrode on the first trocar and a first electrode on the second trocar, and delivering energy to the target tissue to ablate the tissue, thereby forming at least one ablation zone. The ablation procedure can be repeated multiple times, thereby causing multiple overlapping ablation zones.

A probe device is also presented herein that has a longitudinal axis and at least a first trocar and a second trocar. Each of the trocars comprises a proximal portion and a distal portion and a lumen extending along the longitudinal axis. The distal portions of the trocars are capable of piercing tissue. Each trocar has at least two electrodes that are electrically insulated and separated from each other, and each electrode is independently selectively activatable.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 5A illustrates an enlarged longitudinal sectional view of one embodiment of the handle of the energy delivery probe.

FIG. 5B illustrates an enlarged longitudinal sectional view of another embodiment of the handle of the energy delivery probe.

FIG. 7A illustrates an enlarged perspective view of a portion of the distal end of the probe with an anchoring means extending from the distal end of the energy delivery probe.

FIG. 7B illustrates an enlarged perspective view of a portion of the distal end of the probe with another embodiment of an anchoring means in a deployed state.

FIG. 7C illustrates an end view of the anchoring means of FIGS. 7A and 7B.

FIG. 14A illustrates exemplary overlapping first and second ablation zones that are produced after first and second ablations are completed.

FIG. 14B illustrates exemplary overlapping first, second, and third ablation zones that are produced after first, second, and third ablations are completed.

FIG. 15A illustrates an exemplary single ablation zone that is produced after an anchoring means is deployed and a first ablation is completed.

FIG. 15B illustrates exemplary overlapping first and second ablation zones that are produced after an anchoring means is deployed and a first and second ablation are produced.

FIG. 15C illustrates exemplary overlapping first, second, and third ablation zones that are produced after an anchoring means is deployed and first, second, and third ablations are completed.

DETAILED DESCRIPTION OF THE INVENTION

Figure 1:
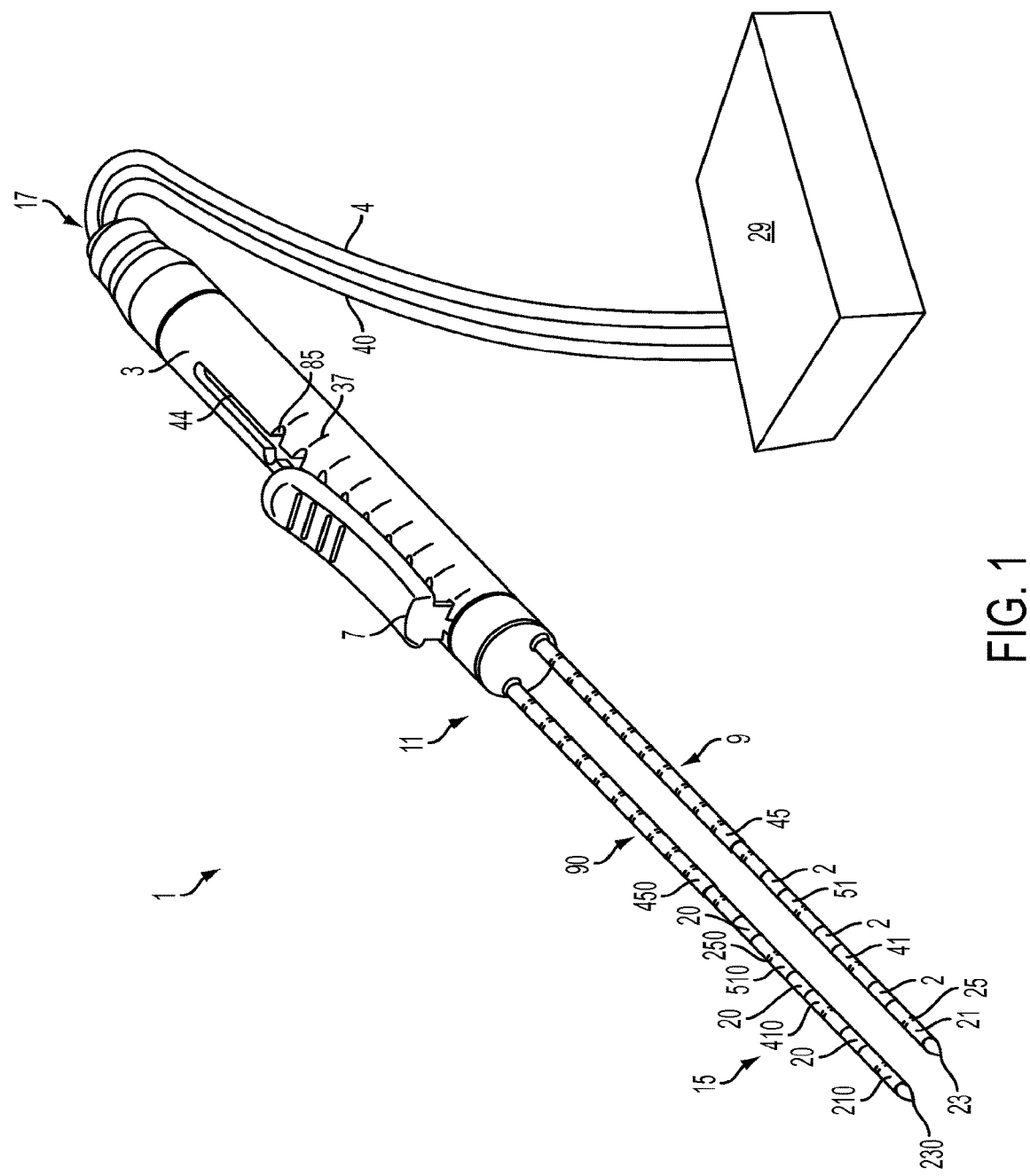
FIG. 1 illustrates a perspective view of a first embodiment of an energy delivery probe device.

The present invention can be understood more readily by reference to the following detailed description and the examples included therein and to the Figures and their previous and following description. The drawings, which are not necessarily to scale, depict selected embodiments and are not intended to limit the scope of the invention. The detailed description illustrates by way of example, not by way of limitation, the principles of the invention.

The skilled artisan will readily appreciate that the devices and methods described herein are merely exemplary and that variations can be made without departing from the spirit and scope of the invention. It is also to be understood that the terminology used herein is for the purpose of describing particular embodiments only and is not intended to be limiting.

Ranges can be expressed herein as from "about" to one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. As used herein, the words "proximal" and "distal" refer to directions away from and closer to, respectively, the insertion tip of the probe in the probe. The terminology includes the words above specifically mentioned, derivatives thereof, and words of similar import.

Other than in the operating examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can be varied as desired. At the very least, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values inclusive of the recited values can be used.

"Formed from" and "formed of" denote open claim language. As such, it is intended that a member "formed from" or "formed of" a list of recited components and/or materials be a member comprising at least these recited components and/or materials, and can further include other non-recited components and/or materials.

Examples provided herein, including those following "such as" and "e.g.," are considered as illustrative only of various aspects and features of the present disclosure and embodiments thereof, without limiting the scope of any of the referenced terms or phrases either within the context or outside the context of such descriptions. Any suitable equivalents, alternatives, and modifications thereof (including materials, substances, constructions, compositions, formulations, means, methods, conditions, etc.) known and/or available to one skilled in the art can be used or carried out in place of or in combination with those disclosed herein, and are considered to fall within the scope of the present disclosure. Throughout the present disclosure in its entirety, any and all of the one, two, or more features and aspects disclosed herein, explicitly or implicitly, following terms "example", "examples", "such as", "e.g.", and the likes thereof may be practiced in any combinations of two, three, or more thereof (including their equivalents, alternatives, and modifications), whenever and wherever appropriate as understood by one of ordinary skill in the art. Some of these examples are themselves sufficient for practice singly (including their equivalents, alternatives, and modifications) without being combined with any other features, as understood by one of ordinary skill in the art. Therefore, specific details disclosed herein are not to be interpreted as limiting, but merely as a basis for the claims and as a representative basis for teaching one skilled in the art to variously employ aspects and features of the present disclosure in virtually any appropriate manner.

As used herein, "substantially", "generally", and other words of degree are relative modifiers intended to indicate permissible variation from the characteristic so modified. It is not intended to be limited to the absolute value or characteristic which it modifies, but rather possessing more of the physical or functional characteristic than its opposite, and preferably, approaching or approximating such a physical or functional characteristic. "Optional" or "optionally" means that the subsequently described element, event or circumstance can or cannot occur, and that the description includes instances where said element, event or circumstance occurs and instances where it does not. The term "ablation" is used herein to refer to either irreversible electroporation (IRE) ablations or radiofrequency ablation (RFA) ablations or both. "IRE ablation device" is used herein to refer to any of the devices described herein that can be used for IRE ablations. "RFA devices" can be used herein to refer to any of the devices described herein that can be used for RF ablations. All dimensions herein are exemplary, and one of ordinary skill in the art will recognize that other dimensions possible.

Referring now in detail to the drawings, in which like reference numerals indicate like parts or elements throughout the several views, in various embodiments, presented herein is an exemplary ablation device that can be used for RF or IRE ablations.

FIG. 1 illustrates one exemplary embodiment of an energy delivery probe 1 for use in treating a patient. The probe can be an RF ablation probe or an IRE ablation probe. The probe 1 has a proximal end 17, a distal end 15 and a longitudinal axis. At least a portion of the proximal end 17 of the probe 1 can be configured to be positioned outside of a human body. At least a portion of the distal end 15 of the probe 1 can be configured to be inserted into at least a portion of a human body, such as, but not limited to, a target tissue.

The probe 1 further comprises an elongate probe body. The elongate body can comprise a trocar 9 having a proximal end, a distal end, and at least one selectively activatable electrode 21, 41, 51. The probe body can be substantially fixed in relation to the trocar 9.

The probe body comprises a handle 3 that can be positioned at the proximal end 17 of the probe 1. The proximal end 17 of the probe and the proximal end of the handle 3 are interchangeably referred to herein. The handle 3 has a distal end 11, an outer surface, and an interior cavity 56. The probe 1 can be operatively coupled at the proximal end 17 of the handle 3 to an energy source 29 by at least one cable 4. A portion of the cable 4 is positioned within at least a portion of the handle 3, such that the at least one cable 4 is adjacent to the proximal end of the probe 1 and extends proximally from the proximal end 17 of the handle 3.

The power source can be, but is not limited to, an RF source, an electrical energy source, or microwave source. In one aspect, the energy source 29 can be a generator. The generator is configured for supplying energy to the probe 1 in a controlled manner. The energy delivery source can be capable of delivering energy that such as, but not limited to, radiofrequency (RF) energy and electrical energy. Such generators can include, but are not limited to, a RITA® 1500X RF generator (AngioDynamics, Inc., Latham, N.Y.) or a NanoKnife® generator (AngioDynamics, Inc., Latham, N.Y.).

The handle 3 has at least one moveable slide member 7 comprising at least one slot 44. The slot 44 is defined within the outer surface of the handle 3 and extends along the longitudinal axis of the probe. The slot 44 further comprises a plurality of grooves 85 that are positioned at a substantially right angle to the longitudinal axis of the slot 44. The handle 3 can be made of any suitable material, such as, but not limited to, ABS plastic or other similar plastics, such as PEEK.

The at least one slide member 7 is slidably disposed on the handle 3. In one aspect, the slide member 7 can be a finger-actuatable slide member 7. At least a portion of the slide member 7 is slidably received within slot 44. The slide member 7 can be manually and axially slidably actuated in a proximal or a distal direction along the longitudinal axis of the probe 1 such that at least a portion of the slide member 7 can be slidably received and locked into place in a single groove 85. Each groove 85 corresponds with an index marking 37. Each marking 37 corresponds with an electrode deployment length and can be used to indicate to a user the required depth of electrode deployment from trocar 9 needed for 2, 3, and 4 cm diameter tissue ablations, for example. At least a portion of the slide member 7 can be operatively coupled to a portion of at least one insulative sleeve 45, described below.

The trocar 9 has a proximal end, at least a portion of which can be positioned within the cavity of and operatively coupled the handle 3. The trocar 9 has a distal end 15. The distal end 15 of the trocar 9 and the distal end of the probe 1 are interchangeably used herein. The at least one trocar 9 and the handle 3 extend along the longitudinal axis of the probe 1. In one exemplary embodiment, the trocars 9, 90 can be spaced apart from about 1.5 cm to about 2.5 cm. The trocars can be of the same length or different lengths. Trocars of different lengths can enable a user to deploy the first trocar 9 to a first depth and a second trocar 90 to a second depth that is different from the first depth. In one exemplary embodiment, the trocars 9, 90 can be deployed to identical depths. The trocars 9, 90 extend distally from the handle 3 to a distal tip 23, 230. The distal tip 23, 230 can be sharp such that it is capable of piercing tissue. In one embodiment, at least a portion of the trocars 9, 90 can be rigid for IRE probes, but flexible or semi-flexible for RF probes. The rigid body and sharp tip 23, 230 of the trocar 9, 90 can be useful for penetrating target tissues, especially large, hard tumors.

The trocars 9 can have at least one lumen 19 (FIGS. 5A-5C) that extends along the longitudinal axis of the probe 1. If the probe 1 is an RF probe, the trocar 9 can be comprised of stainless steel or Inconel. If the probe 1 is an IRE probe, the trocar 9 can be comprised of a non-conductive material such as, but not limited to, polyimide or PEEK (polyether ether ketone). In one exemplary embodiment, the trocar 9 can be from about 13 gauge to about 15 gauge (1.828 mm to 1.449 mm) in size, depending on the desired treatment or a patient's anatomy. The trocar 9 can have a uniform diameter throughout its longitudinal length. The working length of the trocar 9 can be between about 10 cm and about 25 cm. The working length of the trocar is defined from a point just distal of the distal end of the handle 3 to the distal tip 23 of the trocar, depending on the size of the target tissue to be ablated and a patient's anatomy.

The trocars 9, 90 can comprise at least one index marker, such as, but not limited to, at least one depth marking 25, 250 positioned along at least a portion of the outer surface of the trocar 9. The depth markers 25, 250 can be fixed in place and equi-distantly positioned from one another. In one exemplary embodiment, the markers 25, 250 can be spaced apart by about 1 cm. The depth markings 25 can be used to aid a practitioner in gauging the depth of deployment of the distal end of the ablation probe and for determining a desired ablation depth. Each of the trocars 9, 90 can have at least one active electrode region or activatable electrodes 21/210, 41/410, 51/510.

Additionally, an electrically insulative sleeve 45, 450 can be coaxially positioned in a surrounding relationship around at least a portion of at least one of the trocars 9, 90. The insulative sleeve 45, 450 can extend from the proximal end of the trocar 9 to within about 0.25 to about 0.5 inches from the distal tip 23, 230 of the electrode. In one embodiment, insulation sleeve 45, 450 can comprise a polyamide material. The insulation sleeve 45, 450 can be stationary, as illustrated in FIG. 1, thus causing the electrode or voltage delivery regions of each activatable electrode 21/210, 41/410, 51/510 to be fixed or stationary and non-adjustable. Each electrode is non-insulated and has an energy delivery surface. In this embodiment in which the insulative sleeve is stationary, the trocar can be flexible.

Figure 2:
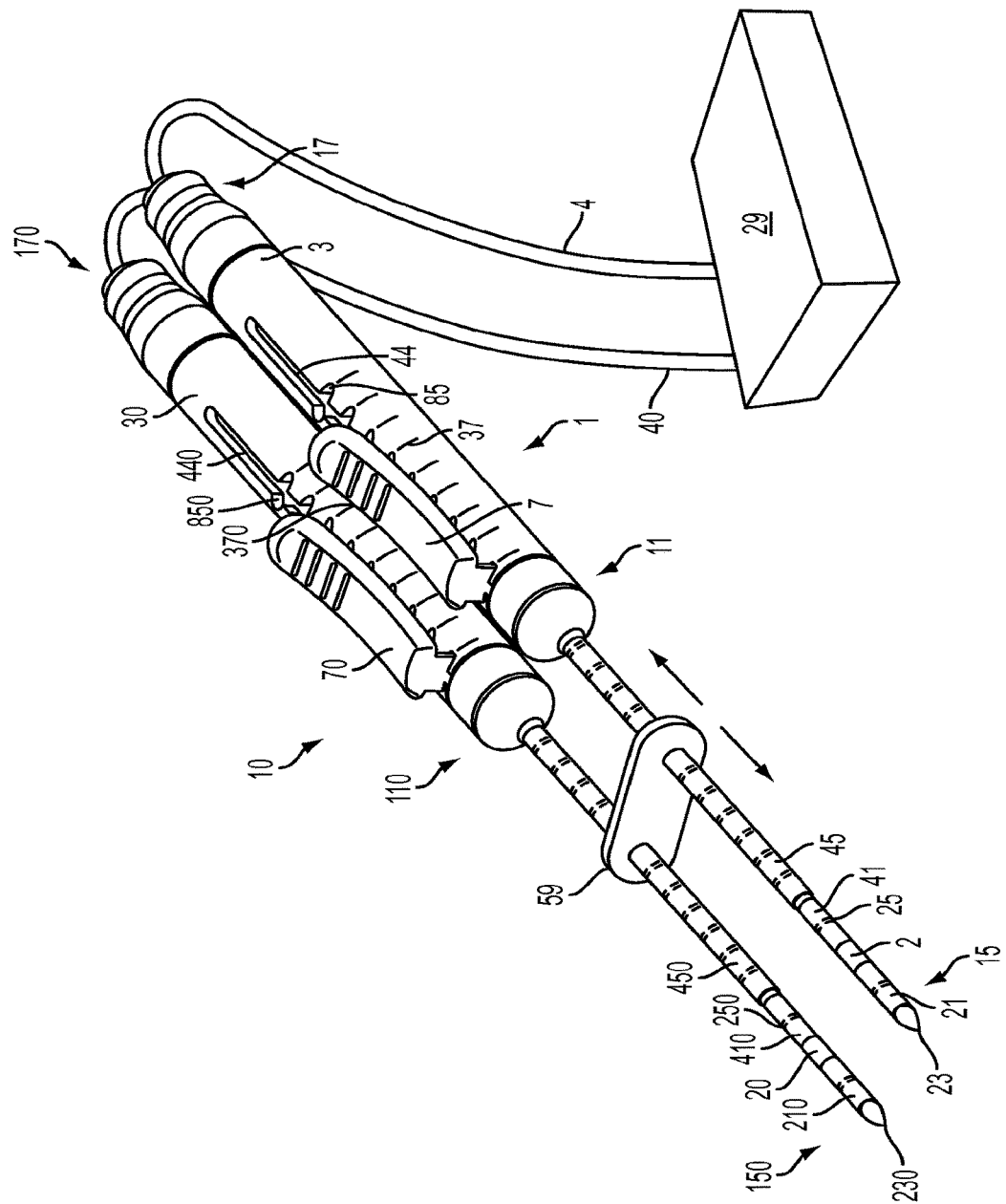
FIG. 2 illustrates a perspective view of a second embodiment of an energy delivery probe device.

In other exemplary embodiments, the insulative sleeve 45, 450 can be axially adjustable, as illustrated in FIGS. 2 and 7A, 7B. This allows a user to adjust or create an energy delivery surface of each of the electrodes, thereby adjusting the resulting ablation zones and the amount of overlap between ablation zones. The insulative sleeve can be mechanically coupled to the slide member or mechanical actuator on the handle member 3. In this embodiment, the trocar 9, 90 can be rigid or semi-rigid. The insulative sleeve 45, 450 can be proximally positioned and/or retracted to expose at least a portion of an energy delivery surface of at least one electrode 21/210, 41/410, 51/510. The exposed electrode(s) can provide at least one energy delivery surface along the surface of the trocar 9. One of ordinary skill in the art will recognize that the insulation sleeve 45, 450 can be initially positioned and/or adjusted along the length of the trocar 9, 90 to any desired position. The adjustable insulative sleeve 45 allows a practitioner to adjust the active electrode section(s) so that the ablation size may be altered, if desired. All or some portion of the insulation sleeve(s) 45 may be adjustably positioned so that the length of an energy delivery surface along the trocar 9 can be varied. As described below, the two or more electrodes 211210, 41/410, 51/510 disposed along the length of the trocar can be electrically insulated from each other by at least one electrically insulating region 2, 20. The thickness of the insulative sleeve 45, 450 can vary, depending on whether the probe is an IRE probe or an RF probe. The insulation thickness may be varied because the operating voltage and currents of IRE and RF devices can be significantly different.

FIG. 2 illustrates a second embodiment of the probe 1. In this embodiment, the probe 1 can comprise two identical bipolar probes 1, 10, each having a trocar 9, 90, respectively. Alternatively, the probes can be monopolar. The probes 1, 10 can be positioned substantially parallel relative to one another. Each of the trocars 9, 90 can be spaced apart at a desired distance from each other such that the probes 1, 10, including the trocars 9, 90, remain parallel to one another at all times before, during, and after ablation. The trocars 9, 90 can be spaced at varying distances from each other depending on whether the probes 1, 10 are RF probes or IRE probes. In one exemplary embodiment, the trocars 9, 90 can be spaced about 1.5 cm-2.5 cm apart from each other. The bipolar probes 1, 10 described herein allow a physician to produce more controlled ablation zones, compared to current commercially available single RF or IRE ablation devices.

As described in U.S. patent application Ser. No. 13/028,431, filed Feb. 16, 2011, incorporated herein in its entirety ("Dual Bracketed Energy Delivery Probe and Method of Use"), a locking spacer 59 can be used to position and maintain the position of trocars 9, 90 such that they remain parallel to each other before, during, and after insertion and ablation treatment using the probes 1, 10. In one aspect, the locking spacer 59 can be a separate component that is capable of being axially slidably mounted onto at least a portion of the outer surface of the trocars 9, 90 for selectively positioning and retaining the pair of trocars 9, 90, and the probes 1, 10. The spacer 59 can be comprised of an ABS plastic material or a similar material. The spacer 59 can have any desired shape or size, such as, but not limited to, square or rectangular. The spacer 59 can have rounded edges. In one aspect, the spacer 59 can be transparent so that the markers 25 on the trocar 9 can remain visible to a practitioner.

Although not illustrated in detail, in one aspect, the spacer 59 can be between about 3 cm and 5 cm across the width of the trocars and between about 1 and 3 cm in thickness along the longitudinal length of the trocars. The spacer 59 can have a body with an outer surface and at least two bores: a first bore and a second bore. Each bore has an inner surface, and each bore is capable of receiving a portion of an outer surface of the first trocar 9 and the second trocar 90. The first and second bores can extend through the body of the spacer 59 such that they are in communication with the exterior of the spacer 59. The position of the bores within the spacer 59 can be adjusted to match a desired spacing between the trocars 9, 90. The bores can be capable of receiving at least a portion of the outer surface of each of trocars 9, 90. Each of the bores of the spacer 59 can be equal to or slightly smaller in diameter than the outer diameter of the insulative sleeves 45, 450 on the trocars 9, 90 in order to provide a sufficient interference fit between the outer surface of the insulative sleeve 45, 450 and the inner surface of the bores. Once the spacer 59 has been positioned along the trocars 9, 90, the interference fit between the outer surface of the insulative sleeve 45 and the inner surface of the bores can prevent the spacer 59 from sliding out of a desired position during insertion and use. Although not illustrated, in one alternative embodiment, the spacer 59 can further comprise a locking mechanism.

The spacer 59 can be slideably moveable or adjustable in either a proximal or a distal direction along the longitudinal length of the trocars 9, 90. In one exemplary embodiment, the spacer 59 can be configured to be received into small grooves (not shown) that can be positioned along the longitudinal length of the outer surface of the insulative sleeves 45, 450. The spacer 59 can be provided in a kit that comprises at least the probes 1, 10, cables 4, 40, and optionally an energy source 29. In one aspect, more than one spacer 59 can be included in the kit. Different sized spacers having variously spaced bores could be included in the kit, depending on the desired ablation treatments.

As described above and illustrated in FIG. 3, each of the trocars 9, 90 can have two or more electrodes 21/210, 41/410, 51/510, each having a voltage delivery region and positioned along the outer surface of each of the trocars. Each of the electrodes can be adapted to receive electrical treatment energy from energy source 29. During use, each voltage delivery region of electrodes 21/210, 41/410, 51/510 can be activated from an inactive state to an active state to actively deliver energy to a target tissue. Energy can be delivered to the target tissue from energy source 29 through the voltage delivery regions or energy delivery surfaces of the electrodes to the target tissue. In one aspect, the energy delivery probe 1 described herein can be configured to operate as a bipolar probe device. Such bipolar probes are described in U.S. patent application Ser. No. 12/437,843, filed May 8, 2009 ("Electroporation Device and Method"), which application is incorporated herein by reference in its entirety.

The two or more electrodes 21/210, 41/410, 51/510 disposed along the length of the trocar can be electrically insulated from each other by at least one electrically insulating region 2, 20. The at least one electrically insulating region(s) 2, 20 can separate the at least two activatable electrodes 21/210, 41/410, 51/510 in a manner sufficient to prevent electrical shorting as well as to prevent arcing between the activatable electrodes 21/210, 41/410, 51/510. In one exemplary embodiment, the electrically insulating regions 2, 20 can have a length of about 1 cm, while the electrodes 21/210, 41/410, 51/510 can have a length of about 2 cm. In one aspect, the insulating regions 2, 20 can be fixed and non-adjustable in dimensions.

Figure 3:
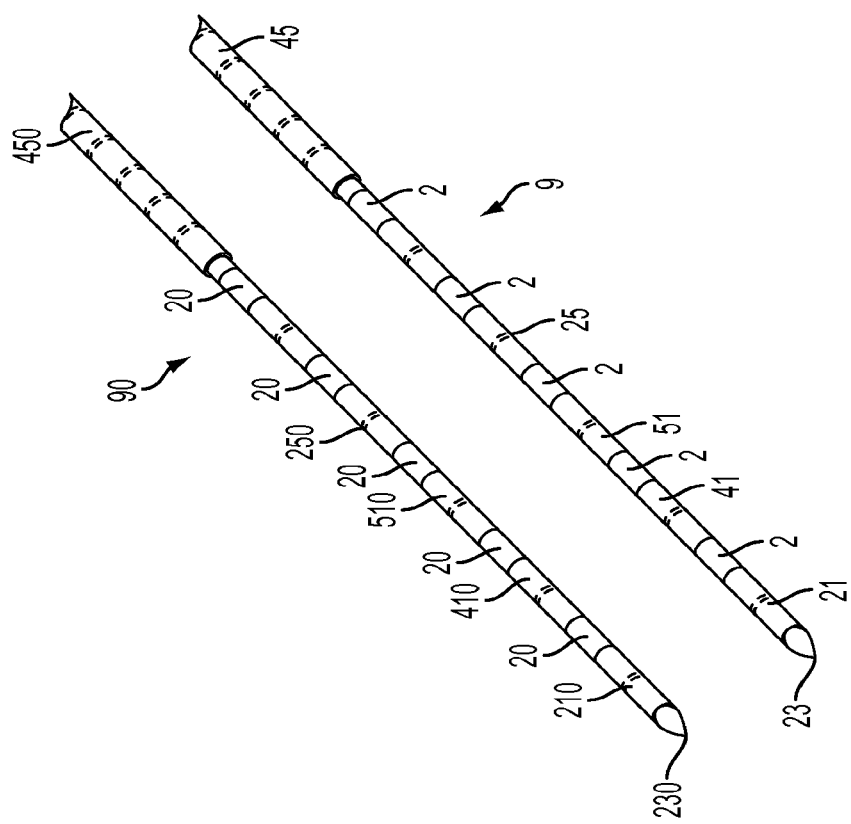
FIG. 3 illustrates an enlarged perspective view of the distal end of the probes of FIG. 2.

As illustrated in FIG. 3, the activatable electrode 21/210 can be positioned at a distal position on trocar 9, 90 such that when the trocars 9, 90 are inserted in a parallel position within target tissue, the activatable electrodes 21, 210 are positioned about 1.5 cm to 3 cm apart from each other. When positioned in a parallel position, together, the activatable electrodes 21, 210 form a first set of electrodes. A second set of electrodes, 41, 410 can be positioned on trocars 9, 90, respectively, proximally of the first set of electrodes. A third set of electrodes 51, 510 can be positioned along the trocar 9, 90 proximally of the first and second set of electrodes 41, 410. Although the device illustrated herein comprises three sets of electrodes, the ablation device can also comprise any suitable number of sets of electrodes, depending on the length of the trocar 9, 90, in order to effectively ablate a target tissue.

The collective size of the energy delivery surfaces of each of the first, second, and third sets of electrodes can be sufficient to create a volumetric ablation zone between any two of the electrodes of each set of electrodes when sufficient energy is delivered from the energy source to the ablation device.

Unless a portion of each of the electrodes is covered by insulation, then the entire length of each electrode is capable of functioning as an energy delivery surface which can deliver energy to a selected tissue mass. The length and size of each energy delivery surface can be variable. In one exemplary embodiment, the energy delivery surface of each electrode can be about 2 cm. In one exemplary embodiment, such as illustrated in FIGS. 1 through 3, the insulative sleeve 45, 450 can be stationary. In this embodiment, the active electrode regions are stationary and cannot be adjusted. In other exemplary embodiments, such as those illustrated in FIGS. 7A through 7C, the insulative sleeves 45, 450 can be adjustable, thereby allowing the length of the activatable electrodes 21/210, 41/410, 51/510 to be adjusted. The active working lengths or energy delivery surfaces of the electrodes can be adjustable by adjusting the position of the insulative sleeve covering the electrodes. Creation of different ablation geometries can be dependent on the length of energy ablation delivery surfaces, the number of electrodes, the size of the delivery surfaces of the electrodes, and the amount of power delivered to the electrodes.

Although not illustrated, in one aspect, any of the energy delivery devices described herein can optionally include at least one cooling mechanism. Such cooling mechanism can comprise the infusion of one or more liquids through the lumen 19 of the trocar 9. The trocar lumen 19 may be coupled to an infusion medium source and deliver an infusion medium to the selected tissue site. A cooling element can be coupled to at least one of the electrodes. The cooling element can be a structure positioned in at least one of the electrodes and can include at least one channel configured to receive a cooling medium. The cooling medium can be recirculated through the channel. RF probes described herein can also optionally include temperature feedback circuitry.

Figure 4A:
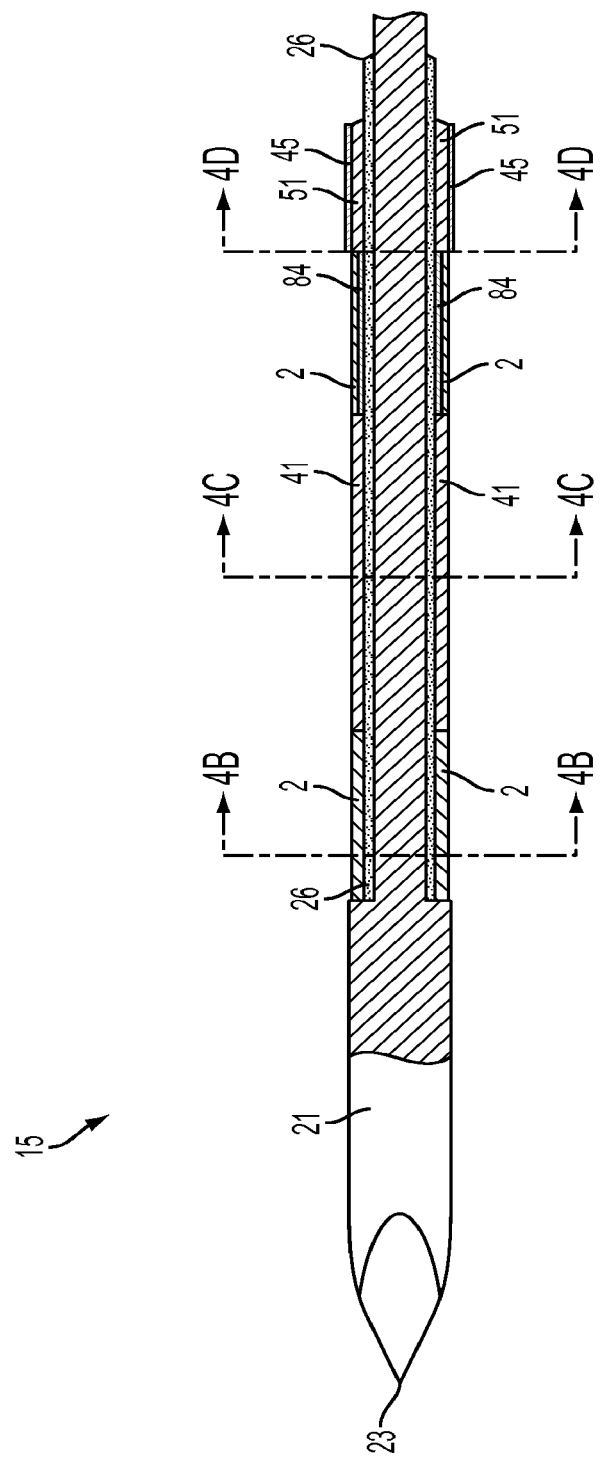
FIG. 4A illustrates a longitudinal cross-sectional view of the distal end of one of the probes of the energy delivery device of FIG. 1.
Figure 4D:
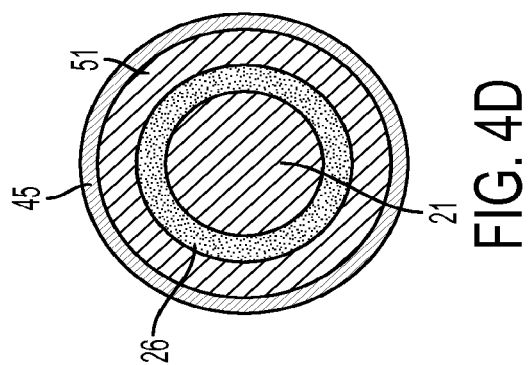
FIG. 4D illustrates a cross-sectional view along lines D-D of the energy delivery probe.
Figure 4C:
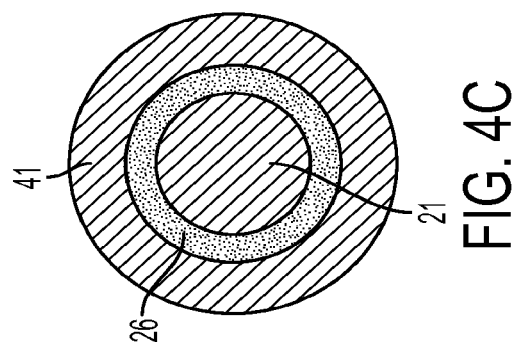
FIG. 4C illustrates a cross-sectional view along lines C-C of the energy delivery probe.
Figure 4B:
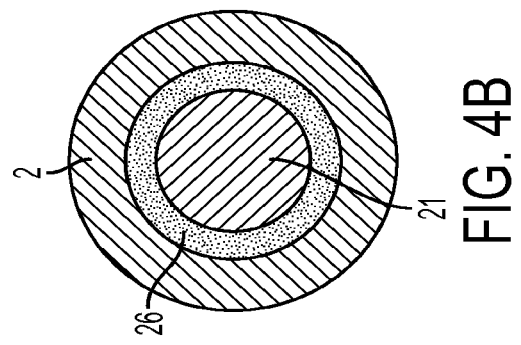
FIG. 4B illustrates a cross-sectional view along lines B-B of the energy delivery probe.

FIG. 4A is a longitudinal sectional view of the distal end of the trocar 9, 90. FIGS. 4B through 4E illustrate various cross-sectional views of the distal end of the trocar 9, 90. The activatable electrodes 21/210, 41/410 or voltage delivery members can be tubular structures coaxially disposed about electrically insulating member 26, having an inner diameter equal to or greater than the outer diameter of electrically insulating member 26. Activatable electrode 21 can be placed in a distally adjacent position to the insulating region 2. Activatable electrode 21 can include a distal portion for voltage delivery, and a proximal portion that can be electrically conducting for electrically coupling the activatable electrode 21 to an energy source 29. The electrode 21 can have a uniform outer diameter along its length. The uniform outer diameter can be substantially the same as the outermost diameters shown in FIGS. 4B-4D, so that the body portion of probe 10 can be substantially uniform in diameter along its length. The orientation and width of the electrically conducting (i.e., active electrode portions) and alternating insulating portions can be arranged so as to provide the probe with a substantially similar and constant diameter throughout its length. Alternatively, the insulating regions 2, 20 can be adjusted in width to provide a variable diameter trocar 9, 90, depending on the diameters of the activatable electrodes 21/210, 41/410 and the insulating regions 2, 20 in relation to each other. The thickness of electrically insulating regions 2, 20 can, in certain embodiments, be about 0.05 inches or less, and in additional embodiments can be 0.03 inches or less. Electrically insulating regions 2, 20 can include a plurality of indexing methods, including depth markings that can be detectable to an operator.

Insulative regions 2, 20 can be comprised of electrically non-conductive materials. Suitable electrically non-conductive materials can have a dielectric strength of 10 MV/m or greater, such as 15 MV/m or greater, or 20 MV/m or greater. Electrically non-conductive materials for insulating regions 2, 20 can include thermosets and thermoplastics, such as polyether ether ketone, polyphenylene sulfide, fluoropolymers, and polyamide-imides.

Electrically insulating regions 2, 20 physically separate and electrically insulate electrode 21/210 from other electrodes 41/410, 51/510 of probe 10. The electrically insulating members 2, 20 can have a distal cylindrical portion that is greater in outer diameter and wall thickness than a proximal cylindrical portion. A central lumen passing through the distal and proximal portions of the electrically insulating member can have a substantially uniform diameter that is equal to or greater than the outer diameter of electrode 21. Non-limiting methods of making an electrically insulating piece can include extrusion (including co-extrusion), molding (including co-injection molding), and others known to one skilled in the art.

The proximal and distal portions of the electrodes 21/210, 41/410, 51/510 can have the same or different compositions, and can independently be comprised of one or more electrically conductive materials, including one or more metals and alloys thereof, such as various grades of stainless steel. Electrode 21/210 can have one or more lumens there through and one or more openings positioned at the distal ends of the active electrode 21/210 as well as on the side of portions of the electrode 21/210 for delivery of substances, including, but not limited to, infusion media, solutions or suspensions containing one or more therapeutic agent as well as diagnostic agents, hydrogels, and colloidal suspensions containing nanoparticles as well as microparticles. In certain embodiments the substances can be delivered to increase the conductivity of the tissue and in others are delivered to increase the efficiency of ablation. In other embodiments the substances are released to alter the conductivity of tissue.

Electrically insulating members 2, 20 can be coaxially disposed about at least a portion of at least one voltage delivery member. Electrically insulating members 2, 20 can be coextensive distally with at least a portion of at least one voltage delivery member, and can extend into handle 3. Electrically insulating members 2, 20 can include one or more insulative regions 2, 84 of the same or different electrically non-conductive materials. Electrically insulating members 2, 20 can electrically insulate at least a portion of at least one voltage delivery member to prevent electrical shorting and arcing thereof, which can adversely affect treatment efficiency as well as efficacy. Use of multiple layers as well as coatings to form electrically insulating members 2, 20 can help to reduce or eliminate the occurrence of pin holes or damages therein during the manufacturing process. When assembling probes 1, 10, electrically insulating members 2, 20 can be applied onto the trocar 9, 90 by methods such as, but not limited to, sliding on and shrink-wrapping one or more tubular structures (including sleeves as well as tubing) of thermoplastics, forming one or more surface coatings, such as vapor deposition, spraying, dipping, as well as molding.

Optionally, one or more of electrodes 21/210, 41/410, 51/510 can be rendered more echogenic than other regions, including the electrically insulating regions 2, 20. Certain embodiments include non-limiting methods for echogenicity enhancement including particle blasting, echogenic coating, perforating, chemical etching, and laser etching. In certain embodiments, microabrasive blasting is applied to voltage delivery regions to achieve a depth of 70 microns.

FIG. 5A illustrates one exemplary embodiment of a handle 3 of the probe body. One of ordinary skill in the art will recognize that other configurations can be used. The handle 3 comprises an outer surface, a proximal end 17, a distal end 11 and an interior or cavity 56. The distal portion 11 of the handle can comprise an opening 22 defined therein a distal face 60 of the handle 3 such that it is sized to allow an outer surface of the trocar 9, 90 extend through the opening 22. The opening 22 faces substantially in a distal direction toward the tissue piercing tip 23, 230 of the probe 1. As illustrated in FIG. 5A, in embodiments where the insulative sleeve 45 is non-moveable, the proximal end of the trocar 9, along with the insulative sleeve 45, which coaxially surrounds the outer surface of the trocar 9 will be secured within the handle 3 to a portion of the interior 56 of the handle 3.

As illustrated in FIG. 5A, and described further herein, in one exemplary embodiment, a deployment means such as, but not limited to, a tension wire member 28 can be coupled to at least a portion of the slide member 7 at the proximal end of the device and can extend along the longitudinal axis within the lumen 19 of the trocar 9 to a distal end of the trocar 9, where the tension wire member 28 can be operatively coupled to an anchoring mechanism 8 (shown in FIGS. 6B through 11) that is deployable from the distal end of the trocars 9, 90.

As illustrated in FIG. 5B, in yet another embodiment, the handle 3 can comprise at least one switching means that can be configured to independently selectively activate at least one electrode. In one aspect, the switching means is coupled to at least one of the electrodes 21/210, 41/410, 51/510. The switching means allows a user to switch any of the electrodes or electrodes 21/210, 41/410, 51/510 between an active or "on" mode and an inactive or "off" mode, thereby allowing a user to control the location of each ablation. In one exemplary embodiment, the switching means can comprise at least one wire member 61 that can be configured to make electrical contact with at least one of the one or more electrodes 51/510, 41/410, 21/210 as the slide member 7 is moved along the outer surface of the handle 3. When the wire member 61 is moved or slides across each electrode 51/510, 41/410, 21/210, the wire member 61 can contact at least one of the proximal electrodes 51/510, 41/410, 21/210. As each of the proximal electrodes is activated, the distal portion of each of the corresponding electrodes 21/210, 41/410, 51/510, in turn, is activated or energized as the wire member 61 makes contact with each of the proximal electrodes. Thus, each electrode can be independently activated, while the remaining electrodes remain inactive. When two probes 1, 10 are being used, a wire member 61, 610 (not shown) for probes 1, 10, respectively, that is capable of contacting each of the electrodes 21, 210 can simultaneously activate electrodes 21, 210 when wire members 61, 610 simultaneously make electrical contact with the electrodes 21, 210, thereby allowing the delivery of energy to a target tissue. By switching between the various active energy delivery modes, a user can perform overlapping ablations without adjusting the position of the ablation device. The use of the switching means allows a user to adjust the area of the tissue treated, adjust the rate of tissue treatment, and adjust the amount of energy delivered to the tissue in order to prevent thermal damage to non-target tissue including coagulation of blood vessels such as the hepatic vein. This mechanism also helps to generate a more uniform ablation profile.

Figure 5C:
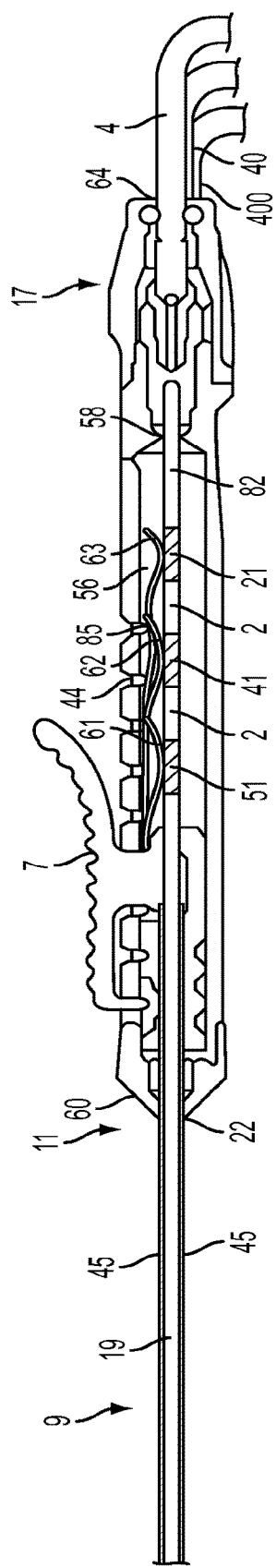
FIG. 5C illustrates an enlarged longitudinal sectional view of another embodiment of the handle of the energy delivery probe.

One of ordinary skill in the art will recognize that various embodiments of the handles illustrated in FIGS. 5A through 5C could be used alone or in combination, depending on the desired features. For example, in one aspect, the handle 3 may comprise at least one tension wire member 28 that can extend the length of the lumen and can be operatively coupled to at least one anchoring means at the distal end of the device, described herein, in addition to at least one wire member 61 that can be operatively coupled to at least one electrode 21, 41, 51.

The trocars 9, 90 can extend proximally into cavity 56 of the handle 3 and can terminate in a distal-facing recess of plug 58. Plug 58 can be fixedly coupled to handle 3 to cap off the interior cavity 56 of the handle 3. As such, a portion of energy delivery probe 1 can be fixedly coupled between at least opening 22 and plug 58 within handle 3. Adhesives or other non-limiting bonding techniques can be used to render probe 1 immovable relative to handle 3. Although opening 22 has a substantially circular shape, one of ordinary skill in the art will recognize that the opening 22 can have other shapes as well, including, but not limited to, elliptical or crescent shaped.

A proximal opening 64 can be defined in the outer surface at the proximal end of the handle 3 such that it is configured for receiving one or more cables 4, 40 from cavity 56. In the embodiments described herein, the ablation device can comprise two cables 4, 40 because at least two probes 1, 10 will be used to ablate tissue. Each of cables 4, 40 can be connected to a probe 1, 10. The one or more cables 4, 40 can be electrically coupled to proximal portion 82 of the trocar 9, thus also to any one of the electrodes 21, 41, 51, through at least one lead wire 35. Non-limiting examples of coupling methods include, but are not limited to, soldering, lead wire wounding, electrically conductor lugs, and combinations thereof.

In one aspect, cavity 56 can be at least partially filled with a flowable material, including but not limited to a liquid, semi-liquid, as well as a gel, and a hardening material, such as, but not limited to, at least one of a cross-linkable, polymerizable, or otherwise curable material, that is electrically insulating, such as epoxy, to secure and immobilize the various components within the cavity 56 of the handle 3, as well as provide electrical insulation among the various components and between the components and a device operator. The components within the handle 3, including cables 4, 40, and lead wire 35, in addition to other components, are immobilized relative to handle 3. The handle design is configured to prevent ingression of fluids into handle 3. As illustrated in FIG. 5C, in yet another embodiment, each electrode 21, 41, 51 can be in electrical contact with a separate wire members 61, 62, 63, respectively. Thus, each of the electrodes can be in separate electrical contact with three separate wire members 61, 62, and 63.

Figure 6A:
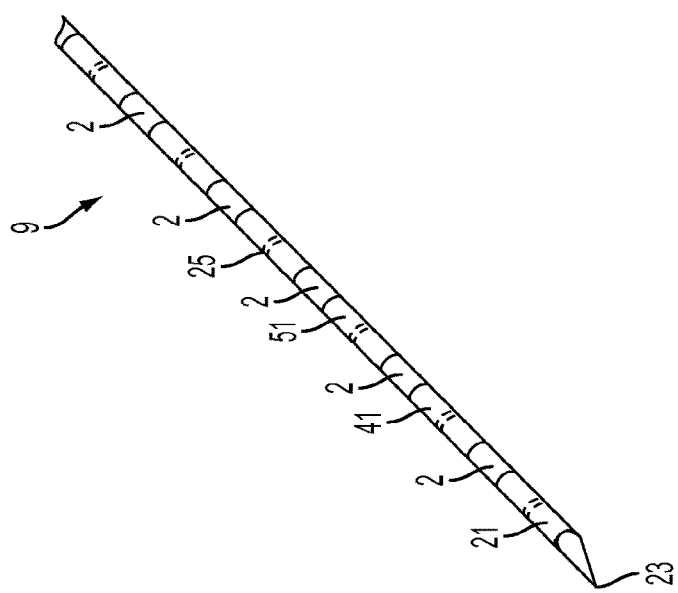
FIG. 6A illustrates an enlarged perspective view of a portion of the distal end of the trocar with an anchoring means retracted inside of the energy delivery probe.
Figure 6B:
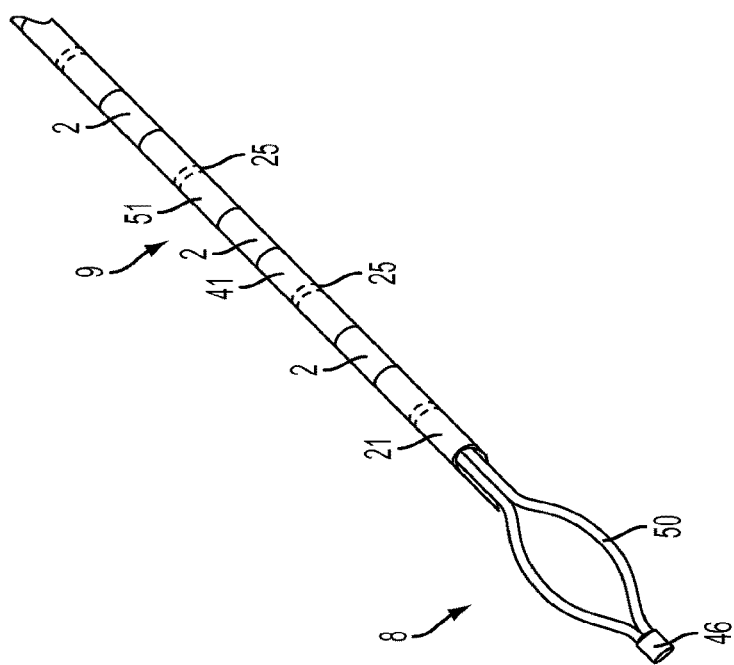
FIG. 6B illustrates an enlarged perspective view of a portion of the distal end of the trocar with an anchoring means deployed from the distal end of the energy delivery probe.
Figure 6C:
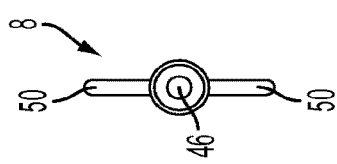
FIG. 6C illustrates an end view of the distal end of the trocar of FIGS. 6A and 6B.

FIGS. 6A through 11 illustrate various anchoring mechanisms 8 that are deployable from the distal end of the ablation probe. In one aspect, the anchoring means 8 can incorporate a means for collecting a biopsy sample. As illustrated in FIGS. 6A through 6C, the ablation probe can comprise a stationary insulative sleeve 45. As illustrated in FIG. 6B, the trocar 9, 90 acts as a sleeve from which the anchoring means can be deployed. The anchoring means 8 can be a distally adjustable loop anchoring structure that can help restrain the ablation probe and anchor the ablation probe in place within the tissue after the probe is inserted into the tissue and before an ablation procedure is performed. The distally adjustable loop anchoring means 8 can comprise oppositely disposed arcuate sections that are joined on both ends. In one aspect, the anchoring means 8 can comprise at least a first arcuate portion and a second arcuate portion, which portions are symmetric with respect to each other. In one aspect, the anchoring means 8 can comprise at least one wire 50. In one aspect, the anchoring means 8 can comprise more than one type of wire member 50, which wires can be symmetric with respect to each other. Each of the first arcuate portion and the second arcuate portions can be joined together by soldering, press-fitting, and the like at a distal-most tip in a secure manner and positioned within tip cover 46. Each of the arcuate wire members 50 can have smooth edges so that the anchoring means is non-traumatic to a patient's tissue after it is implanted. In one aspect, the anchoring means 8 can be biased such that it is radially expandable from a collapsed position to an expanded position from the distal tip of the probe 1. In one aspect, the wire members 50 can be comprised of a shape memory material, such as, but not limited to, Ni Ti, or another shape-memory material.

FIGS. 7A through 7C illustrate another embodiment of the anchoring means 8. In this embodiment, the ablation probe 1 can comprise an adjustable sleeve which can comprise an active electrode 21 and an insulative sleeve 45. In one aspect, the active electrode portion 21 is positioned at the distal end of the sleeve, and the insulative portion 45 is positioned proximally of the active electrode portion 21. The sleeve coaxially surrounds insulative region 2. The sleeve enables a user to adjust the positioning of the active electrode 21 portion and to control the retraction and deployment of the anchoring means 8. In this embodiment, the anchoring means 8 can comprise a plurality of wire members 50. A portion of such member 50 can be arcuate in the deployed position. As described above, the anchoring means 8 can be operatively connected to at least one tension control or wire member 28, illustrated in FIG. 5A. The tension control wire member 28 can extend longitudinally along at least one lumen 19 of the trocar 9 and can be proximally pulled by a user in order to deploy the anchoring means 8 from the distal end of the trocar 9 into the tissue. The tension control wire member 28 can be used for applying an adjustable amount of tension, to force, or to relax, or change the shape of the arcuate sections of the anchoring means 8. In one aspect, the tension control member 28 can be a wire or a tube that can be operatively connected to the slide member 7, as illustrated in FIG. 5A. The anchoring means 8 can be a self-expanding member, or alternatively, the anchoring means can be manually expanded or manipulated by use of the tension wire member 28.

As illustrated in FIGS. 7A and 7B, the anchoring means can comprise two or three wire members that are compressed within a sub-tube that can be retracted into the distal end of the ablation probe. In one aspect, the wire members can be flat or round and may have a blunt tip. The tension control member 28 may be deployed by proximally pulling back the slide member 7, thereby moving the anchoring member 8 distally and deploying the electrodes from the distal edge of the trocar. Once the anchor is exposed, the center tension control wire member 28 can be further tightened or pulled proximally toward the user, causing at least a portion of the plurality of wire members to radially expand outwardly, thereby creating a more expanded anchor member shape.

As described above, the tension control wire member 28 can be positioned within a portion of the handle 3 and can extend through at least one lumen 19 of one of the trocars. The proximal end of the tension member 28 can be operatively coupled to the slide member 7 that is manually slideable thereon the handle 3, and the distal end of the tension member 28 can be operatively coupled to the anchoring member 8. The anchoring member 8 can be deployed from the distal end of the trocar 9 by sliding the actuating/slide member proximally along the trocar. The wires can be deployed after the center tension control wire member 28 is pulled toward the proximal end of the device. When the center wire member 50 is pulled in a proximal direction, the remaining wires expand radially outwardly. When tension is removed from the center tension wire member, the outer wires can return to a relaxed position.

In one aspect, as illustrated in FIG. 7A, in the undeployed state the arcuate wire members 50 of the anchoring means 8 can extend along the longitudinal axis of the ablation device. As illustrated in FIG. 7B, in one aspect, the anchoring means 8 can be deployed by retracting the moveable sleeve 69 while keeping the anchoring means 8 stationary, thereby causing the anchoring means 8 to expand from the distal end of the trocar 9. The moveable sleeve 69 can comprise at least one activatable electrode portion 21 and an insulative sleeve 45 portion. Thus, the anchoring means 8 can be deployable and expandable from the distal end of the trocar 9. The probe can comprise more than one anchoring means 8 that can be deployable from the distal end of the probe 1. The anchoring means 8 can comprise at least three wire members 50. In one aspect, each of the wire members 50 can be positioned such that they each lie in a different plane from each of the other two wire members 50, as illustrated in FIG. 7C, such that the wires form a triangular shape.

Figure 9:
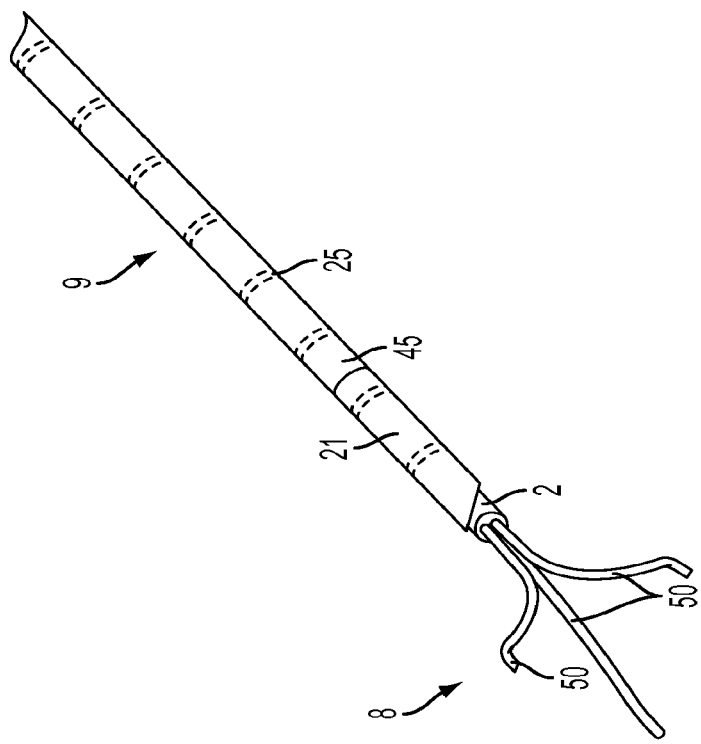
FIG. 9 illustrates an enlarged perspective view of a portion of the distal end of the probe with another embodiment of an anchoring means.
Figure 8:
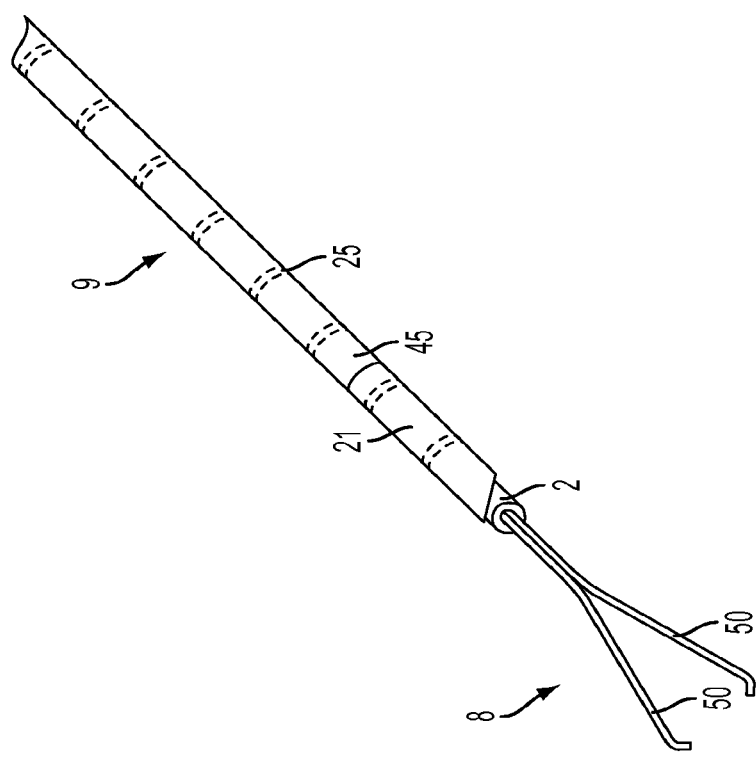
FIG. 8 illustrates an enlarged perspective view of a portion of the distal end of the probe with another embodiment of an anchoring means.

FIGS. 8 and 9 illustrate other embodiments of the anchoring means 8 that can be used with the ablation device described herein. As illustrated in FIG. 8, the anchoring means 8 can comprise two wire members 50 constructed of a flat or round wire or tube, each with a hooked tip. Each of the wire members 50 can be deployed by adjusting the position of the trocar 9 in a proximal direction. Alternatively, the anchoring means 8 can be retracted by sliding the trocar 9 distally over the anchoring means 8. FIG. 9 illustrates yet another embodiment of the anchoring means 8. In this embodiment, the anchoring means 8 comprises three wire members 50. The anchoring means 8 can comprise a single wire member 50 extending longitudinally from the center of the trocar 9, along the longitudinal axis of the trocar and the center wire 50 can be surrounded by at least two laterally extending wire members 50 that can be positioned on either side of the single longitudinally extending wire member 50. Each of the two laterally extending wire members 50 can have a hook formed at the distal tip of each of the laterally extending wire members 50.

Figure 11:
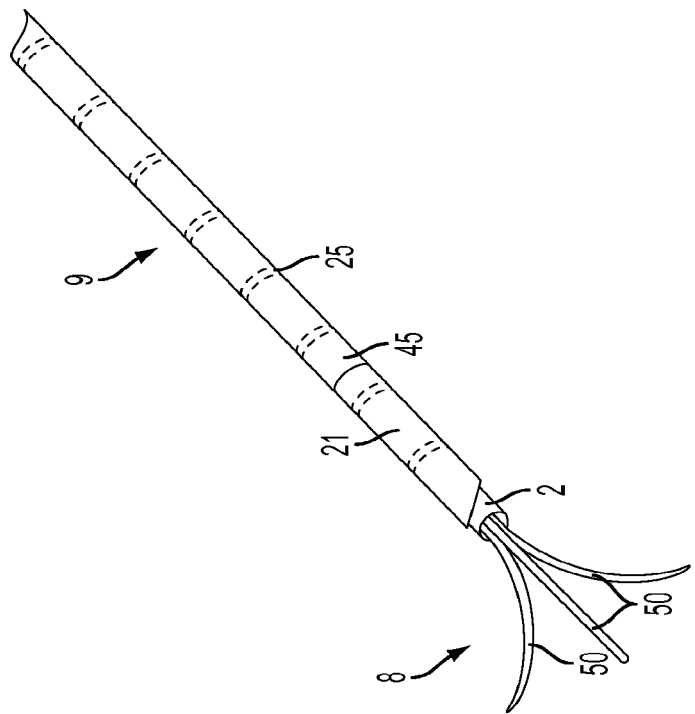
FIG. 11 illustrates an enlarged perspective view of a portion of the distal end of the probe with another embodiment of an anchoring means.
Figure 10:
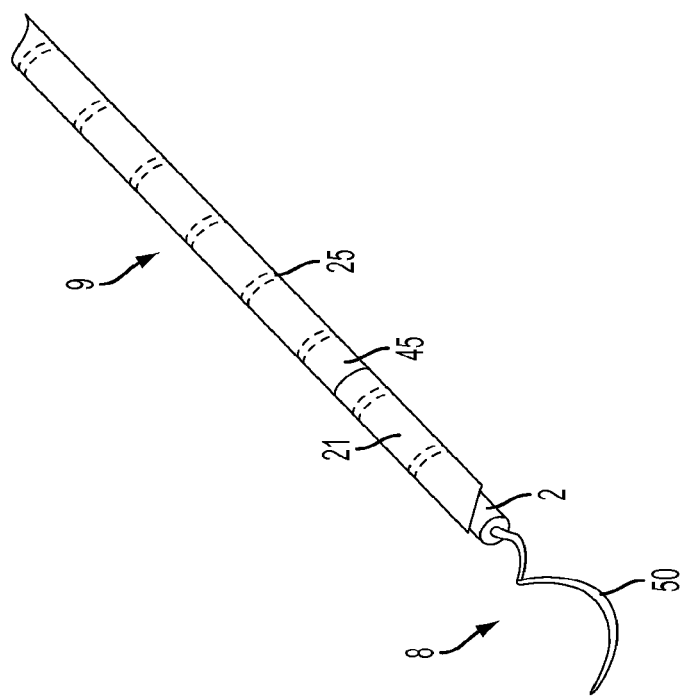
FIG. 10 illustrates an enlarged perspective view of a portion of the distal end of the probe with another embodiment of an anchoring means.

FIGS. 10 and 11 illustrate two additional embodiments of anchoring means 8. In one embodiment FIG. 10 illustrates a single wire member 50. In one aspect, the wire member can have at least a first arcuate section and a second arcuate section that can form an anchor. The first arcuate section can be smaller than the second arcuate section. This anchoring member 8 can be used to anchor the ablation probe in relation to the tissue by rotating the trocar 9. The anchoring means can be removed by rotating and pulling the anchor back into the trocar.

FIG. 11 illustrates another embodiment of the anchoring means 8. In this embodiment, the anchoring means 8 can comprise at least one wire member 50 extending longitudinally from the center of the trocar, and similar to the embodiment in FIG. 10, each wire member 50 can laterally extend away from the longitudinal axis such that the side electrodes are deployed in a laterally outwardly extending direction from the middle longitudinal wire member 50.

Figure 12:
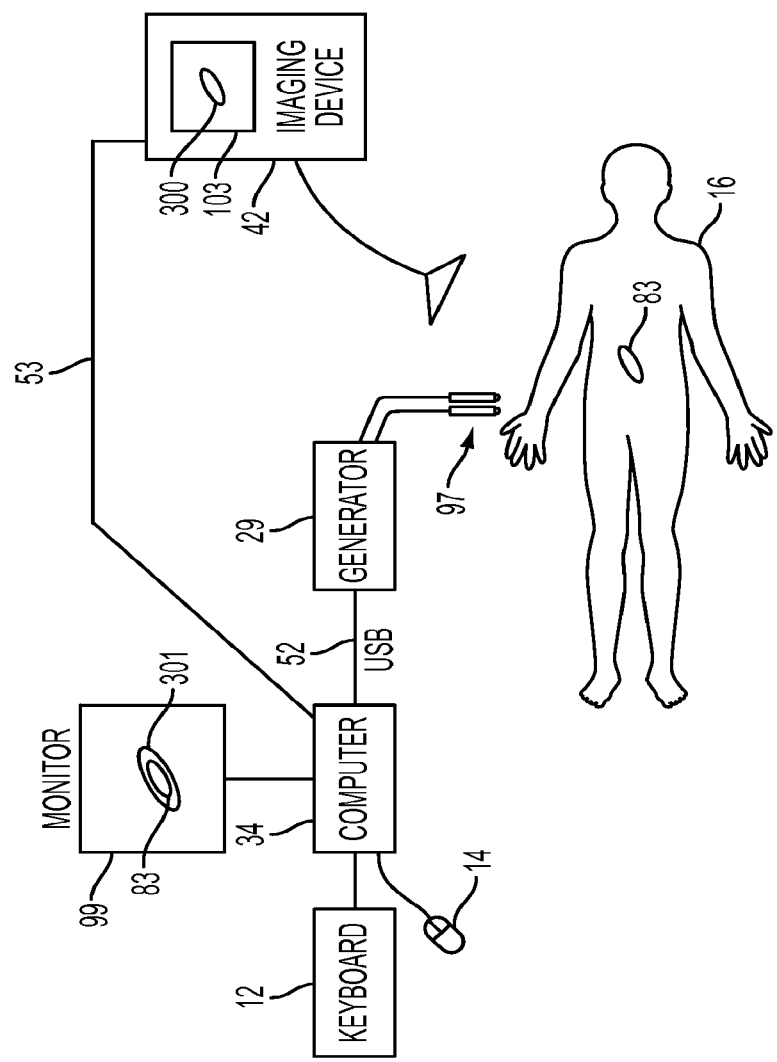
FIG. 12 illustrates a system for use with the energy delivery device described herein.

Referring now to FIGS. 12 through 15C, a method of using the ablation device for IRE or RF ablations to treat a target tissue region is described and illustrated herein. In one aspect, the energy delivery probes 1, 10 described herein can be used with an electrical treatment planning software, such as, but not limited to, that provided by AngioDynamics, Inc. (with the NanoKnife® irreversible electroporation system), described in U.S. patent application Ser. No. 12/751,845, filed Mar. 31, 2010 and Ser. No. 12/751,854, filed Mar. 31, 2010, respectively, which applications are incorporated by reference herein in their entireties. Exemplary components that can be used with the method of the present invention are illustrated in FIG. 12. As described above, one or more probes 1, 10 can deliver therapeutic energy and are powered by a voltage pulse generator, described above, that generates high voltage pulses as therapeutic energy such as pulses capable of irreversibly electroporating the target tissue 83. Although two receptacles 97 for electrodes are illustrated, the voltage pulse generator 29 system can include up to six separate receptacles for receiving up to six individual energy delivery members which can be adapted to be plugged into a respective receptacle. The receptacles can each be labeled with a number in consecutive order. In other embodiments, the voltage pulse generator 29 can have any number of receptacles for receiving more or less than six probes. As described above, each probe 1 can include at least two activatable electrode regions separated by an insulating portion.

The generator or energy source 29 can be connected to a treatment control computer 34 having input devices such as keyboard 12 and a pointing device 14, and an output device such as a display device 99 or monitor for viewing an image of a target treatment area 300 such as a target tissue 83 or target tissue 83 surrounded by a safety margin 301. The computer 34 is attached to a USB 52, which is attached to the generator 29. The computer 34 is also connected to an imaging device 42 via a cable 53. The therapeutic energy delivery device 1 is used to treat a target tissue 83 inside a patient 16. An imaging device 42 includes a monitor 103 for viewing the target tissue 83 inside the patient 16 in real time. Examples of imaging devices 42 include ultrasonic, CT, MRI and fluoroscopic devices as are known in the art. The treatment system can also include computer software, such as treatment control module (not shown), which assists a user to plan for, execute, and review the results of a medical treatment procedure. The treatment control module can display the anticipated ablation zone(s) based on the position of the probes and the treatment parameters and whether the treatment was successful.

The energy delivery probe device 1 can be configured such that the probe 1 can be placed within or adjacent to the target tissue 83, enabling safe usage in situations where the tissue targeted for ablation is adjacent to critical as well as vital non-targeted structures, such as, but not limited to, the urethra or neurovascular bundles. Thus, the disclosed pulsed electric field ablation, when carried out under certain parameters and operating conditions, can selectively spare, including without damaging, destroying or denaturing, certain tissues and structures present within the ablation volume. Non-limiting tissues that can be selectably spared by the pulsed electric field ablation include nervous, vascular, duct, as well as collagen-rich tissues.

Therapeutic energy delivery devices disclosed herein can be designed for tissue destruction in general, such as resection, excision, coagulation, disruption, denaturation, and ablation, and are applicable in a variety of surgical procedures, including but not limited to open surgeries, minimally invasive surgeries (e.g., laparoscopic surgeries, endoscopic surgeries, surgeries through natural body orifices), thermal ablation surgeries, non-thermal surgeries, such as, but not limited to irreversible electroporation (IRE) and radiofrequency (RF), as well as other procedures known to one of ordinary skill in the art.

Figure 13:
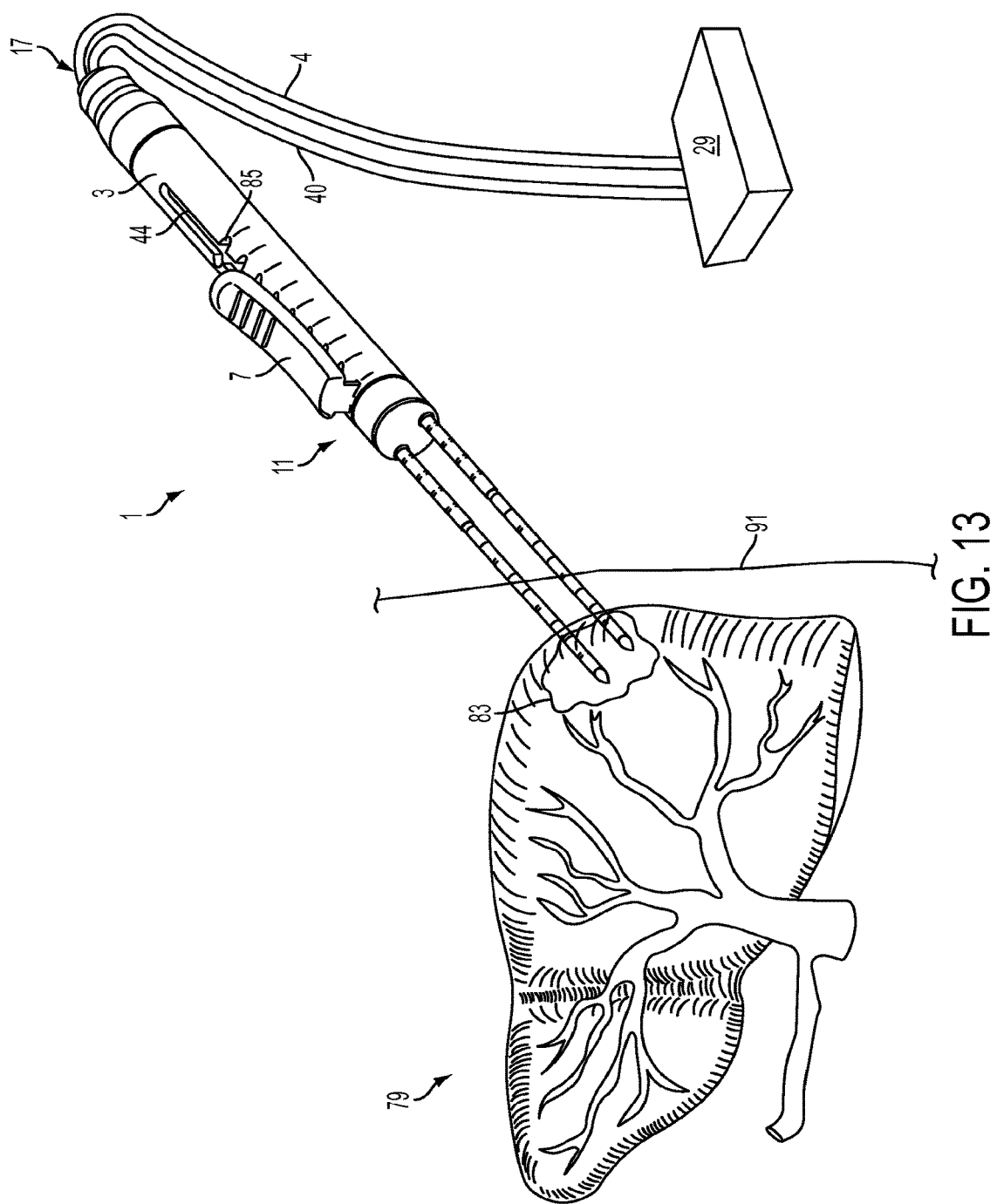
FIG. 13 illustrates a method of using the energy delivery probe described herein to ablate a target tissue.

The method described herein involves identifying a target tissue 83 in a patient 16, as illustrated in FIG. 13. Liver tissue 79 is illustrated in FIG. 13. However, non-limiting examples of tissue masses to which the devices of the present application are applicable include benign tissue masses such as benign prostate hyperplasia (BPH) and uterine fibroids, as well as benign or malignant masses such as cancers and tumors of various tissue types, including, but not limited to, prostate, uterine, lung, liver, kidney, brain, head/neck, bone, stomach, colon, breast, spleen, uterus, vascular, adipose, lymph, ovarian, eye, ear, bladder, skin, and pancreas, or any other desired mammalian target tissue area of a patient's body. The energy delivery probe 1 can be suitable for treatment of conditions for various tissues, volumes, sizes and locations, including small to medium sized tissue volumes, and tissue volumes that are in close proximity to other non-targeted structures, such as, but not limited to, neuronal structures, vascular structures, duct structures, and collagen-rich structures.

An incision in a patient's skin can be created, and one or more probes 1, 10 can be inserted into or near a target tissue 83. The insertion of the one or more probes 1, 10 can be percutaneous, laparoscopic, endoscopic, as well as through natural orifices, including insertions related to orifice translumenal endoscopic surgery. An ablation device can be provided, such as that described above, having at least a first trocar 9 and a second trocar 90 that are spaced in a parallel position relative to each other. In one exemplary aspect, the method can further comprise positioning the first trocar 9 on the first side of the target tissue and the second trocar 90 on the second side of the target tissue. The first and second trocars 9, 90 are inserted into the target tissue 83 such that the first trocar 9 and the second trocar 90 remain substantially parallel during insertion, treatment, and withdrawal of the probe 1, as illustrated in FIG. 13. If using two separate probes, as illustrated in FIG. 2, to help ensure that the trocars 9, 90 remain substantially parallel to each other during insertion and removal, a spacer 59 can be used, as described herein. The electrodes on the first trocar can be substantially parallel to each of the electrodes on the second trocar. Alternatively, at least one of the electrodes on the first trocar can be staggered in position compared to at least one of the electrodes on the second trocar.

The method described herein further involves delivering energy from an energy source 29 through any desired combination of at least two activatable electrodes 21/210; 41/410; and 51/510 of the trocars 9, 90 to a target tissue 83 in order to ablate the target tissue, thereby forming a first ablation zone 47, as illustrated in FIG. 14A. In another aspect, the chosen electrode pairs can be combined in any other combination, such as, but not limited to, 21/410, 210/41, and the like, to produce various ablation sizes. In one aspect, the energy can be independently delivered to each electrode. Alternatively, in another aspect, energy can simultaneously or sequentially be delivered to any combination of electrodes 21/210, 41/410, and 51/510. In one aspect, the ablation zone 47 can be about 1 cm in depth and about 3 cm in width. The ablation zone 47 can be defined as the radiologically identifiable region in which an ablation effect was directly induced. In one aspect, the active electrodes 21/210 can be substantially completely surrounded by the resulting ablation zone 47. In any of the methods described herein, the energy delivered to the target tissue 83 can be radiofrequency energy. Alternatively, the energy delivered can be electrical energy in the form of electrical pulses that can be sufficient to cause non-thermal irreversible electroporation of the target tissue 83 but insufficient to cause thermal damage to the target tissue 83 or tissue surrounding the target tissue.

After a first ablation is completed and a first ablation zone 47 is produced, described above, the method can further involve independently or simultaneously activating a second set of electrodes 41/410 that are positioned on the trocars 9, 90 by delivering electrical energy to the electrodes 41/410 to produce a second ablation zone 48 that can be about 1 cm in depth and about 3 cm in width. As illustrated in FIGS. 14A and 14B, in one aspect, the second ablation zone can be substantially the same size as the first ablation zone 47. Alternatively, the ablation zone size can be altered by changing the amount of energy delivered to the electrodes or by adjusting the energy delivery surface area of the electrodes by other means, such as by adjusting the position of an insulative sleeve 45, as described below. The first ablation zone 47 and the second ablation zone 48 form a first overlapping ablation zone 54 that can be substantially concentrated in depth and width around the insulative regions 2, 20. In one exemplary aspect, the overlapping ablation zone 54 can be about 1 cm in depth and about 3 cm in width. After the second ablation procedure, energy can be delivered to a third set of electrodes 51, 510 to create a third ablation zone 49. In one aspect, the third ablation zone 49 can overlap with the second ablation zone 48, thereby forming a second overlapping ablation zone 55. The sum of the ablation zones 47, 48 produces a total ablation zone 66. The ablation procedure can be repeated as many times as necessary with any set of electrodes along the longitudinal length of the trocars 9, 90 in order to produce a final ablation zone 66. The resulting shapes of the ablation zones described and depicted herein are merely exemplary. One of ordinary skill in the art will recognize that many other types and sizes of ablation zones could be produced.

The method of use of any of the probe assemblies described herein presents a substantial advantage over conventional IRE and RF ablation methods. This probe design and method is advantageous because it allows for overlapping ablations without requiring the removal and reinsertion of the ablation probe(s) or the need for pull-back of the probe(s) between ablations before re-treatment when a lesion is larger than the current a particular needle device can treat, thereby avoiding trauma to the patient and decreasing the chance of mis-positioning of the probe. Thus, this ablation device can incorporate several separate treatment sections along the length of the trocar 9, 90. This ablation procedure can be repeated multiple times in various positions along the trocars 9, 90 to achieve a desired ablation zone(s). This method is also beneficial because by eliminating the need to adjust the position of the device, the chance of re-seeding a tumor track is also decreased.

In embodiments that comprise a moveable insulative sleeve 45, such as illustrated in FIGS. 2 and 3, after energy is delivered to the first set of electrodes 21, 210, then one or both of the insulative sleeves 45, 450 can be adjusted along the length of the trocars 9, 90 to a desired position in order to expose one or more additional sets of electrodes. In one exemplary embodiment, before each ablation procedure, the insulative sleeve 45 can be advanced or retracted along the longitudinal length of the trocar 9, 90 to reveal either a partial energy delivery surface of each electrode of a set of electrodes or a complete energy delivery surface of each electrode of a set of electrodes. For example, after energy is delivered to a first set of electrodes 21, 210 to produce a first ablation zone 47, the insulative sleeve 45 can be adjusted, and energy can then be delivered to a second set of electrodes 41, 410, thereby creating a second ablation zone 48. The insulative sleeve 45 can be adjusted again by proximally moving the insulative sleeve 45 to reveal at least a portion of the third set of electrodes 51, 510. Electrical energy can then be delivered to each electrode of the third set of electrodes, thereby creating a third ablation zone 49, which can overlap with the second ablation zone 48 to form an overlapping ablation zone 55. In one aspect, the overlapping ablation zone 55 can be substantially the same size as the overlapping ablation zone 54. In one aspect, the sum of the different ablation zones 47, 48, 49 can produce a total ablation zone 66. In one aspect, any variety of different positions may be utilized to create different ablation geometries for selected tissue masses of different geometries and sizes.

During the methods described above, energy can be applied from the energy source or generator 29 to the electrodes or any of the sets of electrodes in various patterns. Particularly, electrical pulses of various voltages can be applied to the electrode sets described above to the target tissue 83. In one aspect, energy can be applied between a first set of electrodes 21, 210. In another aspect, energy can be successively applied between a second set of electrodes 41, 410. Finally, energy can be successively delivered between a third set of electrodes 41, 410. Each of these ablations produces a similarly size ablation zone. Additional ablations can be performed between any two corresponding electrode pairs of trocars 9, 90. Software can be used to predict ablation zones using various probe configurations. For example, outlining a predicted ablation zone can be obtained using the finite element method ("FEM") COMSOL Multiphysics Modeling and Simulation software (Palo Alto, Calif.).

In one exemplary embodiment, 90 electric pulses of a 70 microseconds (μsec) pulse length can be delivered per pair of electrodes 21/210, 41/410, and 51/510 at a voltage gradient of 1250 V/cm to the target tissue. Other suitable pulse parameters may be used such as, but not limited to, between 50 and 100 of between 50 and 100 microseconds (μsec) pulse length at a voltage gradient of between about 500 V/cm and about 3000 V/cm. In one aspect, the pulse parameters can be 70 pulses (7 sets of 10 pulses each) at 100 microseconds, with delays of 3.5 seconds between each set of 10 pulses. Voltage gradient (electric field) is a function of the distance between electrodes and electrode geometry, which will vary depending on the size of the tissue sample, tissue properties, and other factors. The parameters such as amplitude of voltage pulses, duration of each pulse, total number of voltage pulses, and duration between consecutive pulses can be altered, depending on the desired ablation.

As illustrated in FIGS. 15A through 15C, the ablation methods described herein can further involve deploying an anchoring mechanism 8 from the distal end(s) of the ablation probes 1, 10 before or after ablation of a target tissue 83. In one aspect, the anchoring means 8 can be fully retracted within a lumen 19 of the ablation probe trocar before and during insertion of the probes 1, 10 into tissue. After the trocars 9, 90 are inserted into a target tissue 83, the anchoring means 8 can be deployed from the distal end of each of the probes 1, 10 into the tissue to secure the probes 1, 10 in relation to the target tissue 83.

Although one type of anchoring means 8 is illustrated in FIGS. 15A through 15C, any suitable type of anchoring means, such as those means illustrated in FIGS. 6B through 11 can be deployed into the target tissue 83. Depending upon the type of anchoring means used, the method may involve further adjusting a tension wire member 28 to further deploy and/or adjust the position of the anchoring means 8. As described herein, the tension wire member 28 may be pulled proximally to deploy wire members of an anchoring means 8. In one exemplary aspect, the anchoring means 8 can be deployed within the tissue such that after the ablation zone(s) are produced, the anchoring means 8 are completely surrounded by the ablation zone(s). After the ablation procedure is completed, the method can further involve retracting the anchoring means 8 into the lumen 19 of the trocar 9 and removing the ablation probes 1, 10 from the target tissue. The advantage of deploying the anchoring means 8 in the tissue is that it helps to restrain the active electrode or voltage delivery portion of the trocar throughout an IRE or RF procedure. Deploying the anchoring means 8 before an ablation procedure also helps to secure the distal ends of the probes 1, 10 within the tissue and helps to prevent probe migration, particularly axial probe migration, within the tissue. This helps to ensure accurate and predictable ablation zones.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". The words "including" and "having," as used herein including the claims, shall have the same meaning as the word "comprising." Those familiar with the art can recognize other equivalents to the specific embodiments described herein, which equivalents are also intended to be encompassed by the claims.

Therapeutic energy delivery devices disclosed herein are designed for tissue destruction in general, such as resection, excision, coagulation, disruption, denaturation, and ablation, and are applicable in a variety of surgical procedures, including, but not limited to, open surgeries, minimally invasive surgeries (e.g., laparoscopic surgeries, endoscopic surgeries, surgeries through natural body orifices), thermal ablation surgeries, non-thermal surgeries, as well as other procedures known to one of ordinary skill in the art. The devices may be designed as disposables or for repeated uses.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g., each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions can be provided by alternative embodiments without departing from the scope of the appended claims. In this regard, for example, different combinations of elements and/or functions than those explicitly described above are also contemplated as can be set forth in some of the appended claims.

This completes the description of the selected embodiments of the invention. Those skilled in the art can recognize other equivalents to the specific embodiments described herein which equivalents are intended to be encompassed by the claims attached hereto.

The invention claimed is:

1. A method of treating tissue in a patient, the method comprising:
    identifying a target tissue;
    inserting at least one energy delivery probe into or near the target tissue, the energy delivery probe comprising at least a first electrode and a second electrode, wherein each electrode is independently selectively activatable;
    an insulator coaxially surrounding the probe, the insulator positioned between the first electrode and the second electrode;
    infusing a fluid through the probe;
    activating the first electrode to deliver an electrical energy to the second electrode;
    delivering energy between the first electrode and the second electrode;
    switching the activation of the electrodes such that the second electrode is activated to deliver the electrical energy to the first electrode;
    delivering electrical energy between the second electrode and the first electrode; and
    forming an ablation zone.

2. The method of claim 1, wherein the at least one energy delivery probe is bipolar.

3. The method of claim 1, wherein infusing a fluid through the probe comprises infusing a cooling fluid.

4. The method of claim 3, wherein the cooling fluid is delivered through a lumen in the at least one energy delivery probe.

5. The method of claim 1, wherein delivering energy further comprises a pulse parameter comprising a first set of five individual pulses, followed by a first delay of up to 2 seconds, followed by a second set of five pulses, followed by a second delay of at least 3.5 seconds.

6. The method of claim 5, wherein the pulse parameter further comprises a third set of five individual pulses, followed by a third delay of up to 2 seconds, followed by a fourth set of five pulses, followed by a fourth delay of at least 3.5 seconds.

7. The method of claim 1, wherein the at least one energy delivery probe is not repositioned during the delivery of energy.

8. A system for treating tissue, the system comprising:
    at least one energy delivery probe into or near the target tissue, the energy delivery probe comprising at least a first electrode and a second electrode, wherein each electrode is independently selectively activatable;
    a switching means, capable of being configured to independently selectively activate at least one of the first electrode and second electrode;
    a generator adapted to deliver energy to the at least one energy delivery probe;
    at least one cooling mechanism to deliver a cooling fluid to the at least one energy delivery probe;
    an insulator coaxially surrounding the probe, the insulator positioned between the first electrode and the second electrode; and
    the switching means activating the first electrode to deliver an electrical energy to the second electrode, delivering energy between the first electrode and the second electrode, the switching means alternating the electrodes by activating the second electrode to deliver the electrical energy to the first electrode, and delivering electrical energy between the second electrode and the first electrode.

9. The system of claim 8, wherein the at least one energy delivery probe is bipolar.

10. The system of claim 8, wherein the cooling fluid is delivered to the at least one energy delivery probe through a lumen in the at least one probe.

11. The system of claim 8, wherein delivering energy further comprises a pulse parameter comprising a first set of five individual pulses, followed by a first delay of up to 2 seconds, followed by a second set of five pulses, followed by a second delay of at least 3.5 seconds.

12. The system of claim 8, wherein the pulse parameter further comprises a third set of five individual pulses, followed by a third delay of up to 2 seconds, followed by a fourth set of five pulses, followed by a fourth delay of at least 3.5 seconds.

13. The system of claim 8, wherein the at least one energy delivery probe is not repositioned during the delivery of energy.

* * * * *